(12) United States Patent
Nomura et al.

(10) Patent No.: US 7,935,674 B2
(45) Date of Patent: May 3, 2011

(54) INDOLE DERIVATIVES

(75) Inventors: Sumihiro Nomura, Osaka (JP); Yasuo Yamamoto, Osaka (JP)

(73) Assignee: Mitsubishi Tanabe Pharma Corporation, Osaka-Shi (JP)

( * ) Notice: Subject to any disclaimer, the term of this patent is extended or adjusted under 35 U.S.C. 154(b) by 0 days.

(21) Appl. No.: 12/487,264

(22) Filed: Jun. 18, 2009

(65) Prior Publication Data

US 2009/0258921 A1    Oct. 15, 2009

Related U.S. Application Data

(63) Continuation of application No. 11/795,804, filed as application No. PCT/JP2006/301921 on Jan. 31, 2006, now abandoned.

(60) Provisional application No. 60/726,653, filed on Oct. 17, 2005.

(30) Foreign Application Priority Data

Jan. 31, 2005  (JP) ................................ 2005-023728

(51) Int. Cl.
A01N 43/04 (2006.01)
A61K 31/70 (2006.01)
C07H 19/00 (2006.01)
C07H 5/06 (2006.01)

(52) U.S. Cl. .......... 514/43; 514/42; 536/22.1; 536/27.1; 536/29.1

(58) Field of Classification Search .................. None
See application file for complete search history.

(56) References Cited

U.S. PATENT DOCUMENTS

| | | | |
|---|---|---|---|
| 5,424,406 A | 6/1995 | Tsujihara et al. |
| 5,731,292 A | 3/1998 | Tsujihara et al. |
| 5,830,873 A | 11/1998 | Tsujihara et al. |
| 6,414,126 B1 | 7/2002 | Ellsworth et al. |
| 6,515,117 B2 | 2/2003 | Ellsworth et al. |
| 6,562,791 B1 | 5/2003 | Maurya et al. |
| 2001/0041674 A1 | 11/2001 | Tomiyama et al. |
| 2002/0052326 A1 | 5/2002 | Washburn |
| 2002/0111315 A1 | 8/2002 | Washburn et al. |
| 2003/0064935 A1 | 4/2003 | Gougoutas |
| 2003/0087843 A1 | 5/2003 | Washburn |
| 2003/0114390 A1 | 6/2003 | Washburn et al. |
| 2004/0053855 A1 | 3/2004 | Fujikura et al. |
| 2004/0063646 A1 | 4/2004 | Fujikura et al. |
| 2004/0110936 A1 | 6/2004 | Ohsumi et al. |
| 2004/0116357 A1 | 6/2004 | Fushimi et al. |
| 2004/0132669 A1 | 7/2004 | Nishimura et al. |
| 2004/0138143 A1 | 7/2004 | Glombik et al. |
| 2004/0259819 A1 | 12/2004 | Frick et al. |
| 2005/0014704 A1 | 1/2005 | Frick et al. |
| 2005/0032711 A1 | 2/2005 | Patel et al. |
| 2005/0032712 A1 | 2/2005 | Urbanski |
| 2005/0037980 A1 | 2/2005 | Rybczynski et al. |
| 2005/0037981 A1 | 2/2005 | Beavers et al. |
| 2005/0233988 A1* | 10/2005 | Nomura et al. .................. 514/43 |
| 2006/0217323 A1 | 9/2006 | Patel et al. |
| 2006/0229260 A1 | 10/2006 | Rybczynski et al. |
| 2006/0234954 A1 | 10/2006 | Urbanski |
| 2006/0293251 A1 | 12/2006 | Urbanski et al. |
| 2007/0060545 A1 | 3/2007 | Nomura et al. |

FOREIGN PATENT DOCUMENTS

| | | |
|---|---|---|
| CA | 2494177 A1 | 2/2004 |
| EP | 1528066 A1 | 5/2005 |
| JP | 2001-288178 A | 10/2001 |
| JP | 2003-12686 A | 1/2003 |
| WO | WO-01/27128 A1 | 4/2001 |
| WO | WO-01/68660 A1 | 9/2001 |
| WO | WO-01/74834 A1 | 10/2001 |
| WO | WO-01/74835 A1 | 10/2001 |
| WO | WO-02/053573 A1 | 7/2002 |
| WO | WO-02/068439 A1 | 9/2002 |
| WO | WO-02/083066 A2 | 10/2002 |
| WO | WO-02/088157 A1 | 11/2002 |
| WO | WO-03/011880 A1 | 2/2003 |
| WO | WO-03/020737 A1 | 3/2003 |
| WO | WO-03/099836 A1 | 12/2003 |
| WO | WO-2004/007517 A1 | 1/2004 |

(Continued)

OTHER PUBLICATIONS

Office Action issued Dec. 19, 2008, in parent U.S. Appl. No. 11/795,804 (abandoned).
R.H.Unger et al., *Diabetologia*, vol. 28, (1985), pp. 119-121.
Luciano Rossetti M.D. et al., *Diabetes Care*, vol. 13, No. 6, (Jun. 1990), pp. 610-630.

(Continued)

*Primary Examiner* — Traviss C McIntosh, III
(74) *Attorney, Agent, or Firm* — Birch, Stewart, Kolasch & Birch, LLP

(57) ABSTRACT

Novel indole derivatives of formula (I) or a pharmaceutically acceptable salt thereof:

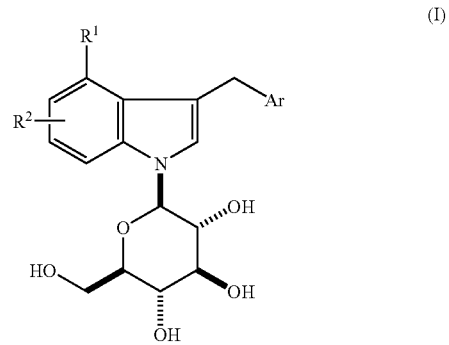

(I)

wherein $R^1$ is halogen, or alkyl, $R^2$ is hydrogen, or halogen, Ar is phenyl, or thienyl, which may be substituted with halogen, alkyl, alkoxy, alkylthio, etc.

19 Claims, No Drawings

FOREIGN PATENT DOCUMENTS

| WO | WO-2004/013118 A1 | 2/2004 |
|----|-------------------|--------|
| WO | WO-2004/014931 A1 | 2/2004 |
| WO | WO-2004/019958 A1 | 3/2004 |
| WO | WO-2004/052902 A1 | 6/2004 |
| WO | WO-2004/052903 A1 | 6/2004 |
| WO | WO-2004/080990 A1 | 9/2004 |
| WO | WO-2006/035796 A1 | 4/2006 |

OTHER PUBLICATIONS

Luciano Rossetti et al., *J. Clin. Invest.*, vol. 79, (May 1987), pp. 1510-1515.

Luciano Rossetti et al., *J. Clin. Invest.*, vol. 80, (Oct. 1987), pp. 1037-1044.

Barbara B. Kahn et al., *J. Clin. Invest.*, vol. 87, (Feb. 1991), pp. 561-570.

Kenji Tsujihara et al., *J. Med. Chem.*, vol. 42, (1999), pp. 5311-5324.

Kenji Arakawa et al., *British Journal of Pharmacology*, vol. 132, (2001), pp. 578-586.

Hongu et al., Chem. Pharm. Bull., vol. 46, No. 1, pp. 22-33, (1998).

Roshan Ahmad et al., *Nucleosides, Nucleotides & Nucleic Acids*, vol. 20, No. 9, (2001), pp. 1671-1682.

Khosrow Zamani et al., *Journal of the Chinese Chemical Society*, vol. 49, (2002), pp. 1041-1044.

Galal T. Maatooq et al., Phytochemistry, vol. 44, No. 1, (Jan. 1997), pp. 187-190.

\* cited by examiner

INDOLE DERIVATIVES

This application is a Continuation of application Ser. No. 11/795,804 filed on Jul. 23, 2007 now abandoned, and for which priority is claimed under 35 U.S.C. §120. Application Ser. No. 11/795,804 is the U.S. National Phase of PCT/JP2006/301921, filed Jan. 31, 2006. This application also claims priority of Application No. 2005-023728 filed in Japan on Jan. 31, 2005 under 35 U.S.C. §119(a), to U.S. Provisional Application No. 60/726,653, filed Oct. 17, 2005, under 35 U.S.C. §119(e), and to U.S. application Ser. No. 10/045,446, filed Jan. 31, 2005, under 35 U.S.C. §120; the entire contents of all are hereby incorporated by reference.

TECHNICAL FIELD

The present invention relates to novel indole derivatives possessing activity as inhibitors of sodium-dependent glucose transporters (SGLT) found in the intestine or kidney.

BACKGROUND ART

Diet therapy and exercise therapy are essential in the treatment of diabetes mellitus. When these therapies do not sufficiently control conditions of patients, insulin or anti-diabetic agents are used. At the present, biguanides, sulfonylureas, insulin-sensitizing agents and α-glucosidase inhibitors are used for anti-diabetic agents. However, these anti-diabetic agents have various side effects. For example, biguanides cause lactic acidosis, sulfonylureas cause significant hypoglycemia, insulin-sensitizing agents cause edema and heart failure, and α-glucosidase inhibitors cause abdominal bloating and diarrhea. Under these circumstances, new anti-diabetic drugs that eliminate these side effects are anticipated.

Recently, it has been reported that hyperglycemia participates in the onset and progression of diabetes mellitus. This theory is called glucose toxicity theory. Namely, chronic hyperglycemia leads to decrease of insulin secretion and insulin sensitivity, the plasma glucose level is elevated, and as a result, diabetes mellitus is self-exacerbated [cf., Diabetologia, vol. 28, p. 119 (1985); Diabetes Care, vol. 13, p. 610 (1990), etc.]. Based on this theory, it is expected that normalization of plasma glucose level interrupts the aforementioned self-exacerbating cycle and the prevention or treatment of diabetes mellitus can be achieved.

It is considered that one method for the treatment of hyperglycemia is to excrete an excess amount of glucose directly into urine so that the blood glucose concentration can be normalized. For example, by inhibiting sodium-dependent glucose transporters being present at the proximal convoluted tubule of kidney, the re-absorption of glucose at the kidney is inhibited whereby the excretion of glucose into urine can be promoted and the blood glucose level can be decreased. In fact, it is confirmed that by continuous subcutaneous administration of an SGLT inhibitor, phlorizin, to diabetic animal models, the blood glucose level thereof can be normalized, and that by keeping the blood glucose level normal for a long time, the insulin secretion and insulin resistance can be improved [cf., Journal of Clinical Investigation, vol. 79, p. 1510 (1987); ibid., vol. 80, p. 1037 (1987); ibid., vol. 87, p. 561 (1991), etc.].

In addition, by treating diabetic animal models with an SGLT inhibitor for a long time, insulin secretion response and insulin sensitivity of the animal models are improved without incurring any adverse affects on the kidney or imbalance in blood levels of electrolytes, and as a result, the onset and progress of diabetic nephropathy and diabetic neuropathy are prevented [cf., Journal of Medicinal Chemistry, vol. 42, p. 5311 (1999); British Journal of Pharmacology, vol. 132, p. 578 (2001), etc.].

In view of the above, SGLT inhibitors are expected to improve insulin secretion and insulin resistance by decreasing the blood glucose level in diabetic patients and to prevent the onset and progress of diabetes mellitus and diabetic complications.

WO 01/27128 discloses aryl C-glycosides having the following structure:

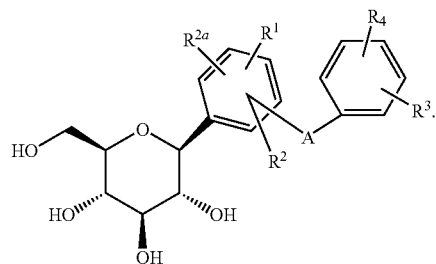

The compounds are disclosed as SGLT inhibitors and are useful in the prevention or treatment of diabetes and related disease.

DISCLOSURE OF INVENTION

The present invention relates to novel indole derivatives of formula (I), or a pharmaceutically acceptable salt thereof:

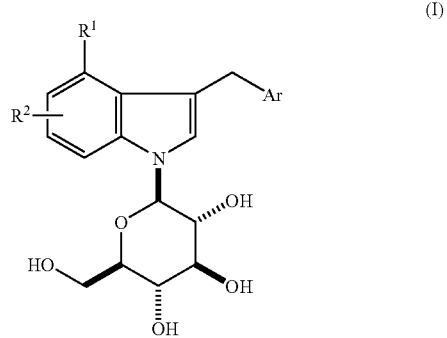

wherein $R^1$ is halogen, or alkyl,
$R^2$ hydrogen, or halogen, and
Ar is one of the following groups:

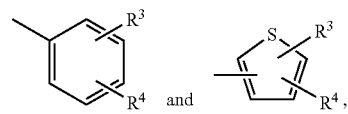

in which $R^3$ and $R^4$ are independently hydrogen, halogen, alkyl, cycloalkyl, haloalkyl, alkoxy, haloalkoxy, alkylthio, hydroxy, phenyl, halophenyl, cyanophenyl, pyridyl, halopyridyl, thienyl, or halothienyl, or $R^3$ and $R^4$ together with carbon atoms to which they are attached form a fused benzene, furan or dihydrofuran ring.

The compounds of formula (I) possess activity as inhibitors of SGLT found in the intestine and kidney of mammals, and are useful in the treatment or prevention of diabetes mellitus and diabetic complications such as diabetic retinopathy, diabetic neuropathy, diabetic nephropathy, and delayed wound healing, and related diseases.

BEST MODE FOR CARRYING OUT THE INVENTION

The term "halogen" or "halo" means chlorine, bromine, fluorine and iodine, and chlorine and fluorine are preferable.

The term "alkyl" means a straight or branched saturated monovalent hydrocarbon chain having 1 to 6 carbon atoms. Examples thereof are methyl, ethyl, propyl, isopropyl, butyl, t-butyl, isobutyl, and various branched chain isomers thereof. Preferably, it means a straight or branched carbon chain having 1 to 4 carbon atoms. Most preferably, it means a straight carbon chain having one or two carbon atoms.

The term "alkoxy" includes the above alkyl group linked to an oxygen atom.

The term "alkylthio" includes the above alkyl group linked to a sulfur atom.

The term "alkanoyl" includes the above alkyl group linked to a carbonyl group.

Further, the terms "haloalkyl", "haloalkoxy", "halophenyl", "halopyridyl" and "halothienyl" respectively refer to an alkyl, alkoxy, phenyl, pyridyl and thienyl group being substituted by one or more halogen atoms, preferably Cl or F. Examples of "haloalkyl", "haloalkoxy", "halophenyl", "halopyridyl" and "halothienyl" include $CHF_2$, $CF_3$, $CHF_2O$, $CF_3O$, $CF_3CH_2$, $CF_3CH_2O$, $FCH_2CH_2O$, $ClCH_2CH_2O$, $FC_6H_4$, $ClC_6H_4$, $BrC_6H_4$, $IC_6H_4$, $FC_5H_3N$, $ClC_5H_3N$, $BrC_5H_3N$, $FC_4H_2S$, $ClC_4H_2S$, and $BrC_4H_2S$.

Similarly, the term "cyanophenyl" refers to a phenyl group being substituted by one or more cyano groups.

The pharmaceutically acceptable salts of the compounds of formula (I) include, for example, a salt with an alkali metal such as lithium, sodium, potassium, etc.; a salt with an alkaline earth metal such as calcium, magnesium, etc.; a salt with zinc or aluminum; a salt with an organic base such as ammonium, choline, diethanolamine, lysine, ethylenediamine, t-butylamine, t-octyl-amine, tris(hydroxymethyl)aminomethane, N-methyl-glucosamine, triethanolamine and dehydroabietylamine; a salt with an inorganic acid such as hydrochloric acid, hydrobromic acid, hydroiodic acid, sulfuric acid, nitric acid, phosphoric acid, etc.; or a salt with an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, benzenesulfonic acid, etc.; or a salt with an acidic amino acid such as aspartic acid, glutamic acid, etc.

The compounds of the present invention may optionally have one or more asymmetric carbon atoms contained in any substituents, and the compounds of formula (I) may exist in the form of enantiomer or diastereomer, or a mixture thereof. The compounds of the present invention include a mixture of stereoisomers, or each pure or substantially pure isomer. In case that the compounds of formula (I) are obtained in the form of a diastereomer or enantiomer, they can be separated by a conventional method well know in the art such as chromatography or fractional crystallization.

In addition, the compounds of formula (I) include an intramolecular salt, hydrate, solvate or polymorphism thereof.

In a preferable embodiment of the present invention, the compounds of the present invention are represented by the following formula:

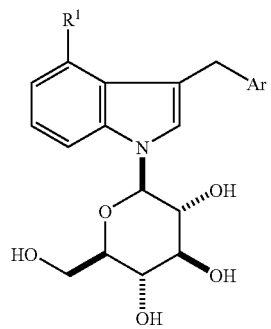

(I-A)

wherein the symbols are the same as defined above. In this embodiment, $R^1$ preferably halogen.

In another preferable embodiment of the present invention, $R^1$ is halogen, $R^2$ is hydrogen, Ar is

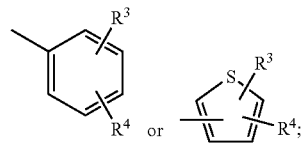

and $R^3$ and $R^4$ are independently hydrogen, halogen, alkyl, haloalkyl, alkoxy, haloalkoxy, alkylthio, phenyl, halophenyl, cyanophenyl, pyridyl or halopyridyl, or $R^3$ and $R^4$ together with carbon atoms to which they are attached form a fused benzene, furan or dihydrofuran ring.

Preferably, $R^3$ and $R^4$ are independently hydrogen, halogen, alkyl, haloalkyl, alkoxy, haloalkoxy, or alkylthio, or $R^3$ and $R^4$ together with carbon atoms to which they are attached form a fused furan or dihydrofuran ring.

More preferably, $R^3$ and $R^4$ are independently hydrogen, halogen, alkyl, haloalkyl, alkoxy, or haloalkoxy, or $R^3$ and $R^4$ together with carbon atoms to which they are attached form a fused furan or dihydrofuran ring.

In another preferable embodiment of the present invention, $R^1$ is fluorine, chlorine, or bromine, and preferably fluorine or chlorine.

In still another preferable embodiment of the present invention, Ar is

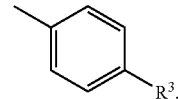

In this embodiment, $R^3$ is preferably halogen, alkyl, alkoxy, haloalkoxy or alkylthio, and $R^1$ is preferably chlorine. More preferably, $R^3$ is halogen, alkyl, or alkoxy. Most preferably, $R^3$ is chlorine, ethyl, or ethoxy.

In an alternative embodiment, $R^3$ is preferably halogen, alkyl, haloalkyl, alkoxy, or haloalkoxy, and $R^1$ is preferably chlorine. More preferably, $R^3$ is chlorine, bromine, iodine, ethyl, difluoromethyl, ethoxy or difluoromethoxy.

In an alternative embodiment, $R^3$ is halogen, haloalkyl, or haloalkoxy.

In an alternative embodiment, preferably $R^1$ is fluorine, and $R^3$ is alkyl, alkoxy, haloalkyl, or haloalkoxy. More preferably $R^3$ is ethyl, ethoxy, or chloroethoxy.

In another preferable embodiment of the present invention, Ar is

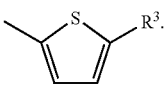

In this embodiment, preferably $R^1$ is halogen, and $R^3$ is halogen, or alkyl. More preferably, $R^1$ is chlorine, and $R^3$ is halogen.

In another preferable embodiment of the present invention, Ar is

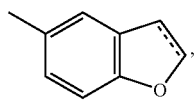

in which ---- represents a single bond or a double bond.

Preferred compounds of the present invention may be selected from the following group:
4-chloro-3-(4-ethylphenylmethyl)-1-(β-D-glucopyranosyl)-indole;
4-chloro-3-(4-ethoxyphenylmethyl)-1-(β-D-glucopyranosyl)-indole;
3-(5-bromothiophen-2-yl-methyl)-4-chloro-1-(β-D-glucopyranosyl)indole;
3-(4-ethylphenylmethyl)-4-fluoro-1-(β-D-glucopyranosyl)-indole; and
a pharmaceutically acceptable salt thereof.

In an alternative embodiment of the invention, preferred compounds may be selected from the following group:
4-chloro-3-(4-chlorophenylmethyl)-1-(β-D-glucopyranosyl)-indole;
3-(4-ethoxyphenylmethyl)-4-fluoro-1-(β-D-glucopyranosyl)-indole;
3-(4-bromophenylmethyl)-4-chloro-1-(β-D-glucopyranosyl)-indole;
3-(benzo[b]furan-5-yl-methyl)-4-chloro-1-(β-D-glucopyranosyl)indole;
4-chloro-3-(4-(difluoromethyl)phenylmethyl)-1-(β-D-gluco-pyranosyl)indole;
4-chloro-3-(4-(difluoromethoxy)phenylmethyl)-1-(β-D-gluco-pyranosyl)indole;
4-chloro-3-(4-iodophenylmethyl)-1-(β-D-glucopyranosyl)-indole;
4-chloro-3-(4-(trifluoromethoxy)phenylmethyl)-1-(β-D-glucopyranosyl)indole; and
a pharmaceutically acceptable salt thereof.

The characteristic of the compounds of the present invention is the introduction of halogen (particularly fluorine, chlorine, or bromine) or alkyl (particularly methyl) at the 4-position of the indole ring. This characteristic is not specifically described in prior publications.

The compounds of the present invention possess activity as inhibitors of sodium-dependent glucose transporter, and show excellent blood glucose lowering effect.

The compounds of the present invention are expected to be useful in the treatment, prevention or delaying the progression or onset of diabetes mellitus (type 1 and type 2 diabetes mellitus, etc.), diabetic complications (such as diabetic retinopathy, diabetic neuropathy, diabetic nephropathy), postprandial hyperglycemia, delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, atherosclerosis, or hypertension.

The compounds of the present invention or a pharmaceutically acceptable salt thereof may be administered either orally or parenterally, and can be used in the form of a suitable pharmaceutical preparation. Suitable pharmaceutical preparations for oral administration include, for example, solid preparations such as tablets, granules, capsules, and powders, or solution preparations, suspension preparations, emulsion preparations, and the like. Suitable pharmaceutical preparations for parenteral administration include, for example, suppositories; injection preparations or intravenous drip preparations, using distilled water for injection, physiological saline solution or aqueous glucose solution; and inhalant preparations.

The pharmaceutical compositions herein will contain, per dosage unit, e.g., tablet, capsule, powder, injection, suppository, teaspoonful and the like, from about 0.01 mg/kg to about 100 mg/kg body weight (preferably from about 0.01 mg/kg to about 50 mg/kg; and, more preferably, from about 0.01 mg/kg to about 30 mg/kg) of the active ingredient, and may be given at a dosage of from about 0.01 mg/kg/day to about 100 mg/kg/day (preferably from about 0.01 mg/kg/day to about 50 mg/kg/day and more preferably from about 0.01 mg/kg/day to about 30 mg/kg/day). The method of treating a disorder described in the present invention may also be carried out using a pharmaceutical composition comprising any of the compounds as defined herein and a pharmaceutical acceptable carrier. The dosage form will contain from about 0.01 mg/kg to about 100 mg/kg (preferably from about 0.01 mg/kg to about 50 mg/kg; and, more preferably, from about 0.01 mg/kg to about 30 mg/kg) of the active ingredient, and may be constituted into any form suitable for the mode of administration selected. The dosages, however, may be varied depending upon administration routes, the requirement of the subjects, the severity of the condition being treated and the compound being employed. The use of either daily administration or post-periodic dosing may be employed.

The compounds of formula (I) may be used, if necessary, in combination with one or more of other anti-diabetic agents, antihyperglycemic agents and/or agents for treatment of other diseases. The present compounds and these other agents may be administered in the same dosage form, or in a separate oral dosage form or by injection.

Examples of the other anti-diabetic agents and anti-hyper glycemic agents include insulin, insulin secretagogues, insulin sensitizers, or other ant-diabetic agents having an action mechanism different from SGLT Inhibition. Specifically, examples of these agents are biguanides, sulfonylureas, α-glucosidase inhibitors, PPARγ agonists (e.g., thiazolidinedione compounds), PPARα/γ dual agonists, PPARpan agonists, dipeptidyl peptidase IV (DPP4) inhibitors, mitiglinide, nateglinide, repaglinide, insulin, glucagon-like peptide-1 (GLP-1) and its receptor agonists, PTP1B inhibitors, glycogen phosphorylase inhibitors, RXR modulators, glucose 6-phosphatase inhibitors, GPR40 agonists/antagonists, GPR119 agonists, GPR120 agonists, glucokinase (GK) activators, and fructose 1,6-bisphosphatase (FBPase) inhibitors.

Examples of the agents for treatment of other diseases include anti-obesity agents, antihypertensive agents, antiplatelet agents, anti-atherosclerotic agents and hypolipidemic agents.

The anti-obesity agents which may be optionally employed in combination with the compound of the present invention include β₃ adrenergic agonists, lipase Inhibitors, serotonin (and dopamine) reuptake inhibitors, thyroid hormone receptor beta drugs, anorectic agents, NPY antagonists, Leptin analogs MC4 agonists and CB1 antagonists.

The anti-platelet agents which may be optionally employed in combination with the compound of the present invention include abciximab, ticlopidine, eptifibatide, dipyridamole, aspirin, anagrelide, tirofiban and clopidogrel.

The anti-hypertensive agents which may be optionally employed in combination with the compound of the present invention include ACE inhibitors, calcium antagonists, alpha-blockers, diuretics, centrally acting agents, angiotensin-II antagonists, beta-blockers and vasopeptidase inhibitors.

The hypolipidemic agents which may be optionally employed in combination with the compound of the present invention include MTP inhibitors, HMG CoA reductase inhibitors, squalene synthetase inhibitors, squalene epoxidase inhibitors, fibric acid derivatives, ACAT inhibitors, lipoxygenase inhibitors, cholesterol absorption inhibitors, ileal Na⁺/bile acid cotransporter inhibitors, upregulators of LDL receptor activity, bile acid sequestrants, nicotinic acid and derivatives thereof, CETP inhibitors, and ABC A1 upregulators.

The compounds of formula (I) may be used in combination with agents for treatment of diabetic complications, if necessary. These agents include, for example, PKC inhibitors and/or ACE inhibitors.

The various agents described above may be employed in the same dosage form with compounds of formula (I) or in different dosage forms, in dosages and regimens as generally known in the art.

The dosage of those agents may vary according to, for example, ages, body weight, conditions of patients, administration routes, and dosage forms.

These pharmaceutical compositions may be orally administered to mammalian species including human beings, apes, and dogs, in the dosage form of, for example, tablet, capsule, granule or powder, or parenterally administered in the form of injection preparation, or intranasally, or in the form of transdermal patch.

The compounds of formula (I) of the present invention or a pharmaceutically acceptable salt thereof, can be prepared by deprotecting compounds of formula (II):

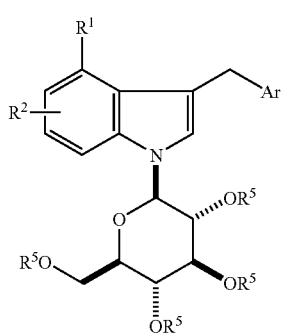

(II)

wherein $R^5$ is a protecting group for a hydroxy group, and the other symbols are the same as defined above, followed by converting the resulting compound into a pharmaceutically acceptable salt, if desired.

The compounds of formula (II) are believed to be novel and form a further aspect of this invention.

In the compounds of formula (II), the protecting group for a hydroxy group can be selected from conventional protecting groups for a hydroxy group, and examples of such protecting group include benzyl, alkanoyl such as acetyl, and alkylsilyl such as trimethylsilyl, triethylsilyl and t-butyldimethylsilyl. Further, the protecting group for a hydroxy group may form acetal or silylacetal together with adjacent hydroxy groups. Examples of such protecting group include an alkylidene group such as isopropylidene and sec-butylidene, a benzylidene group, and a dialkylsilylene group such as di-tert-butylsilylene group. Preferably, $R^5$ is alkanoyl such as acetyl.

The deprotection can be carried out according to kinds of the protecting group to be removed, and conventional methods such as reduction, hydrolysis, acid treatment, and fluoride treatment, can be used for the deprotection.

For example, when a benzyl group is to be removed, the deprotect on can be carried out by (1) catalytic reduction using a palladium catalyst (e.g., palladium-carbon and palladium hydroxide) under hydrogen atmosphere in a suitable inert solvent (e.g., methanol, ethyl alcohol, and ethyl acetate); (2) treatment with an dealkylating agent such as boron tribromide, boron trichloride, boron trichloride.dimethylsulfide complex, or iodotrimethylsilane in an inert solvent (e.g., dichloromethane); or (3) treatment with an alkylthiol such as ethanethiol in the presence of a Lewis acid (e.g., boron trifluoride.diethyl ether complex) in a suitable inert solvent (e.g., dichloromethane).

When a protecting group is removed by hydrolysis, the hydrolysis can be carried out by treating the compounds of formula (II) with a base (e.g., sodium hydroxide, potassium hydroxide, lithium hydroxide, sodium methoxide, and sodium ethoxide) in a suitable inert solvent (e.g., tetrahydrofuran, dioxane, methanol, ethyl alcohol, and water).

Acid treatment can be carried out by treating the compounds of formula (II) with an acid (e.g., hydrochloric acid, p-toluene-sulfonic acid, methanesulfonic acid, and trifluoroacetic acid) in a suitable solvent (e.g., methanol, and ethyl alcohol).

In case of the fluoride treatment, it can be carried out by treating the compounds of formula (II) with a fluoride (e.g., hydrogen fluoride, hydrogen fluoride-pyridine, tetrabutylammonium fluoride, etc.) in a suitable inert solvent (e.g., acetic acid, alcohols (methanol, ethyl alcohol, etc.), acetonitrile, and tetrahydrofuran).

The deprotection reaction can be preferably carried out at lowered, ambient or elevated temperature, for example, from 0° C. to 50° C., more preferably from 0° C. to room temperature.

The compound of the present invention thus obtained may be isolated and purified by a conventional method well known in the organic synthetic chemistry such as recrystallization, column chromatography, thin layer chromatography, and the like.

The compound of formula (II) can be prepared in accordance with steps described in Schemes 1-3.

During any of the processes for preparation of the compounds of the present invention, it may be necessary and/or desirable to protect sensitive or reactive groups on any of the molecules concerned. This may be achieved by means of conventional protecting groups. For a general description of protecting groups and their use, see T. W. Greene et al., "Protecting Groups in Organic Synthesis", John Wiley & Sons, New York, 1999. The protecting groups may be removed at a subsequent step using methods known to those skilled in the art.

Scheme 1:

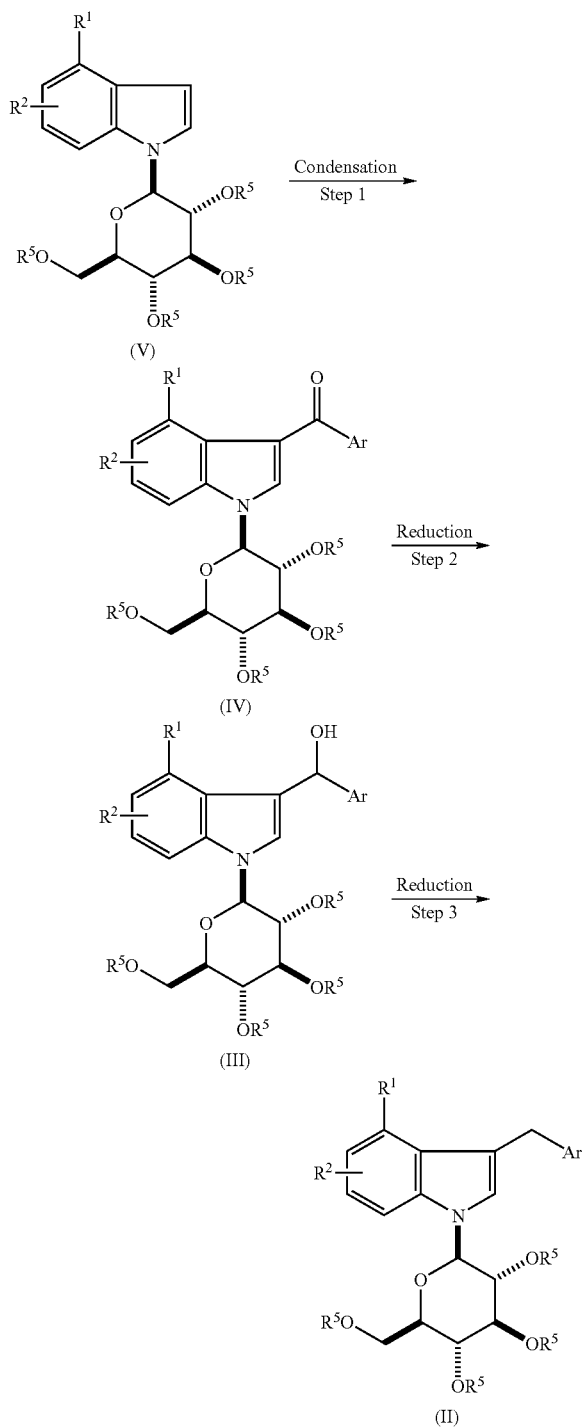

(In the above scheme, the symbols are the same as defined above.)

The compound (II) can be prepared by the following steps:

Step 1:

A compound of formula (IV) can be prepared by condensing a compound of formula (V) with a compound of formula (VI):

Ar—COCl  (VI)

wherein Ar is the same as defined above.

The condensation can be carried out, according to the Friedel-Crafts acylation well known in the art, in a suitable solvent in the presence of a Lewis acid.

Examples of the Lewis acid include aluminum chloride, boron trifluoride.diethyl ether complex, tin(IV) chloride, and titanium tetrachloride.

The solvent can be selected from any one which does not disturb the Friedel-Crafts reaction, and examples of the solvent include halogenoalkanes such as dichloromethane, chloroform, and dichloroethane.

The reaction can be carried out at lowered, ambient or elevated temperature, for example, from −3° C. to 60° C.

Step 2:

A compound of formula (III) can be prepared by reducing the compound of formula (IV).

The reduction can be carried out by treating the compound (IV) with a reducing agent in a suitable solvent.

Examples of the reducing agent include borohydrides (e.g., sodium borohydride with or without cerium(III) chloride heptahydrate, sodium triacetoxyborohydride) and aluminum hydrides (e.g., lithium aluminum hydride, and diisobutyl aluminum hydride).

The solvent can be selected from any one which does not disturb the reaction and examples of the solvent include ethers (e.g., tetrahydrofuran, diethyl ether, dimethoxyethane, and dioxane), alcohols (e.g., methanol, ethyl alcohol and 2-propanol) and a mixture of these solvents.

The reduction reaction can be carried out at lowered, or ambient temperature, for example, from −30° C. to 25° C.

Step 3:

A compound of formula (III) can be prepared by reducing the compound of formula (III).

The reduction of the compound (III) can be carried out by treatment with a silane reagent or a borohydride in the presence of an acid in a suitable solvent or without a solvent.

Examples of the acid include a Lewis acid such as boron trifluoride.diethyl ether complex and titanium tetrachloride, and a strong organic acid such as trifluoroacetic acid, and methanesulfonic acid.

Examples of silane reagents include trialkylsilanes such as triethylsilane, triisopropylsilane.

Examples of borohydrides include sodium borohydride and sodium triacetoxyborohydride.

The solvent can be selected from any one which does not disturb the reaction, and examples of the solvent include acetonitrile, halogenoalkanes (e.g., dichloromethane, chloroform and dichloroethane), and a mixture or these solvents.

The reduction can be carried out at lowered or ambient temperature, for example, from −30° C. to 25° C.

Scheme 2:

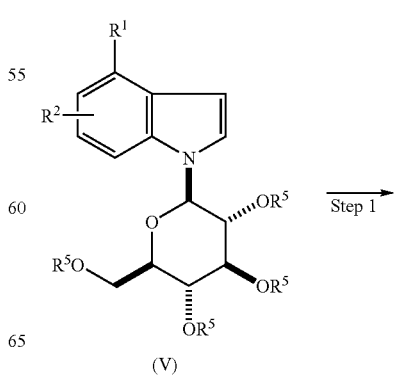

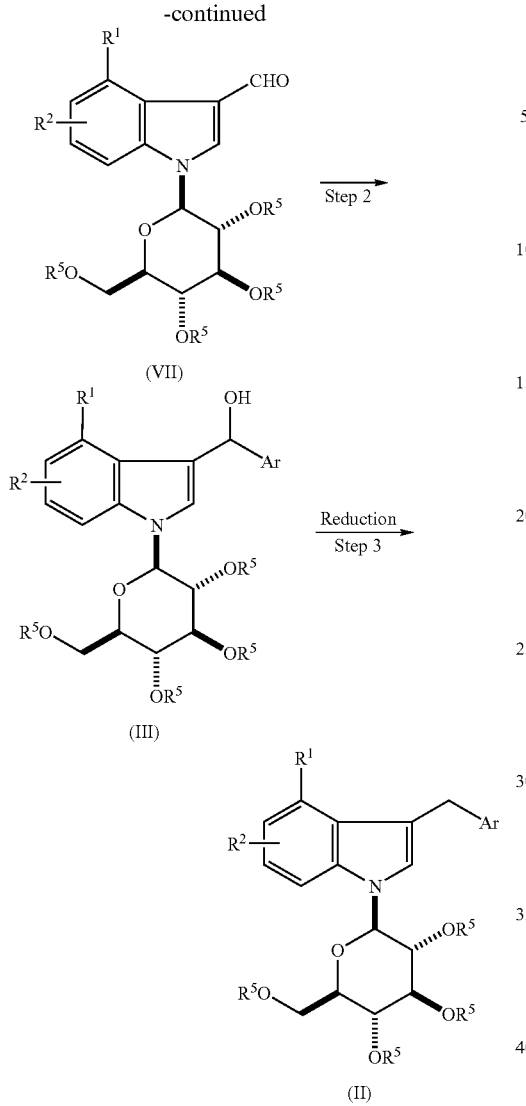

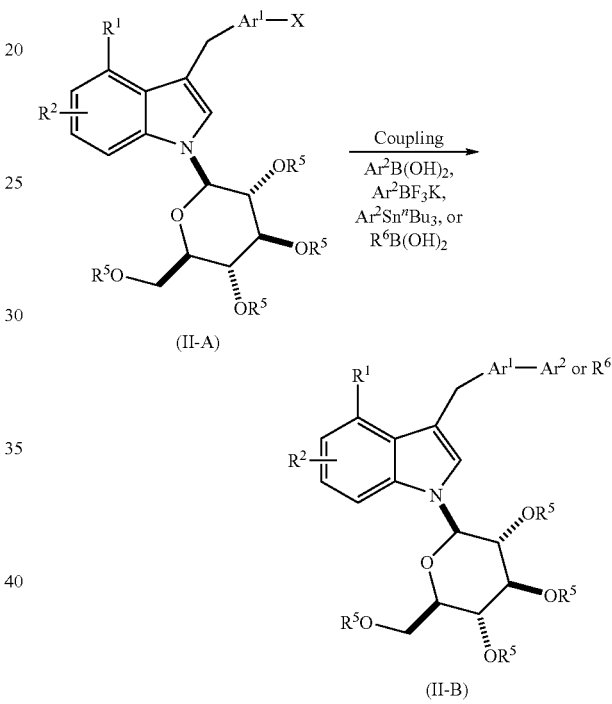

The coupling reaction of the compound (VII) with ArB(OH)₂ can be typically carried out in the presence of a catalyst such as (acetylacetonato)dicarbonylrhodium (I) or hydroxyl-(1,5-cyclooctadiene)rhodium(I) dimer and a ligand such as 1,1'-bis(diphenylphosphino)ferrocene or tri-tert-butyl-phosphine in a suitable solvent being an inert solvent such as tetrahydrofuran, dimethoxyethane and 1,4-dioxane at ambient or elevated temperature, for example, 25° C. to 100° C.

Step 3:

A compound of formula (II) can be prepared by reducing the compound of formula (III).

The reduction can be carried out in accordance with the manner described in Scheme 1, Step 3.

Scheme 3:

(In the above scheme, the symbols are the same as defined above.)

The compound (II) can be prepared according to the following steps:

Step 1:

A compound of formula (VII) can be prepared by formylation of a compound of formula (V) with a Vilsmeier reagent or α,α-dichloromethyl methyl ether/titanium tetrachloride.

The Vilsmeier reagent can be prepared in a conventional manner well known in the art, for example, from dimethylformamide or N-methylformanilide/phosphorus oxychloride, thionyl chloride or oxalyl chloride.

The reaction is typically carried out in a suitable solvent such as dimethylformamide or dichloroethane at ambient or elevated temperature, for example, from 25° C. to 80° C.

Step 2:

A compound of formula (III) can be prepared by coupling the compound of formula (VII) with ArLi, ArMgBr, ArZnBr, Ar(Me)₂LiZn or ArB(OH)₂, where Ar is as defined above.

The coupling reaction of the compound (VII) with ArLi, ArMgBr, ArZnBr or Ar(Me)₂LiZn can be typically carried out in a suitable solvent being an inert organic solvent such as diethyl ether, tetrahydrofuran, or 1,4-dioxane at ambient or lowered temperature, for example, −78° C. to 25° C.

(In the above scheme, Ar¹ is phenyl, or thienyl, X is bromine or iodine, Ar² is phenyl, halophenyl, cyanophenyl, pyridyl, halopyridyl, thienyl or halothienyl, R⁶ is cycloalkyl, ″Bu is n-butyl, and the other symbols are the same as defined above.)

The compound (II-B) can be prepared by coupling a compound of formula (II-A) with Ar²B(OH)₂, Ar²BF₃K, Ar²Sn″Bu₃ or R⁶B(OH)₂, wherein Ar², R⁶ and ″Bu are as defined above.

The coupling reaction can be carried out by a conventional aryl coupling method, e.g., Suzuki coupling method (for reference see: Suzuki et al., *Synth. Commun.* 11:513 (1981); Suzuki, *Pure and Appl. Chem.* 57:1749-1758 (1985); Suzuki et al., *Chem. Rev.* 95:2457-2483 (1995); Shieh et al., *J. Org. Chem.* 57:379-381 (992); Martin et al., *Acta Chemica Scandinavica* 47:221-230 (1993); Wallace et al., *Tetrahedron Lett.* 43:6987-6990 (2002) and Molander et al., *J. Org. Chem.* 68:4302-4314 (2003)) and Stille coupling method (for reference see: Stille, *Angew. Chem. Int. Ed. Engl.* 25:508-524 (1986) and Liebeskind et al., *J. Org. Chem.* 59:5905-5911 (1994)).

The coupling reaction can be carried out in the presence of a Pd catalyst and a base with or without a ligand and an additive in a suitable solvent.

Examples of the Pd catalyst are tetrakis(triphenyl-phosphine)palladium(0), palladium(II) acetate, bis(aceto-nitrile) dichloropalladium(II), dichlorobis(triphenyl-phosphine)palladium(II), [1,1'-bis(diphenylphosphino)-ferrocene] dichloropalladium(II) complex with dichloromethane, tris(dibenzylidene-acetone)dipalladium(0)-chloroform adduct and palladium(II) chloride. Examples of the base include alkali metal carbonates (e.g., potassium carbonate, sodium carbonate and sodium bicarbonate), alkali metal phosphates (e.g., potassium phosphate tribasic, sodium phosphate and sodium hydrogen-phosphate), organic bases (e.g., N,N-diisopropylethylamine) and alkali metal fluorides (e.g., cesium fluoride and potassium fluoride). Examples of the ligand include tricyclohexylphosphine and tri(o-tolyl)phosphine. Examples of the additive include copper(I) iodide.

The solvent can be selected from any one which does not disturb the coupling reaction, and examples of the solvent are aromatic hydrocarbons (e.g., benzene, and toluene), ethers (e.g., tetrahydrofuran, 1,2-dimethoxyethane, and 1,4-dioxane), amides (e.g., dimethylformamide, dimethylacetamide, 1,3-dimethyl-2-imidazolidinone and N-methylpyrrolidone), alcohols (methanol, ethyl alcohol, and 2-propanol), water, and a mixture of these solvents.

The coupling reaction can be carried out at ambient or elevated temperature, for example, from 25° C. to 150° C., preferably from 80° C. to 150° C.

The starting compound of formula (V) can be prepared in accordance with the following scheme:

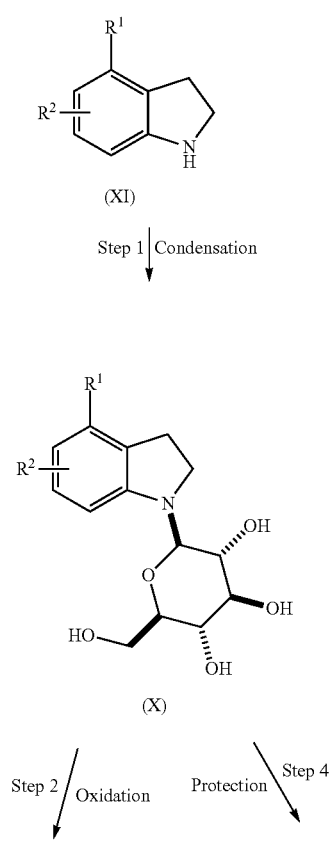

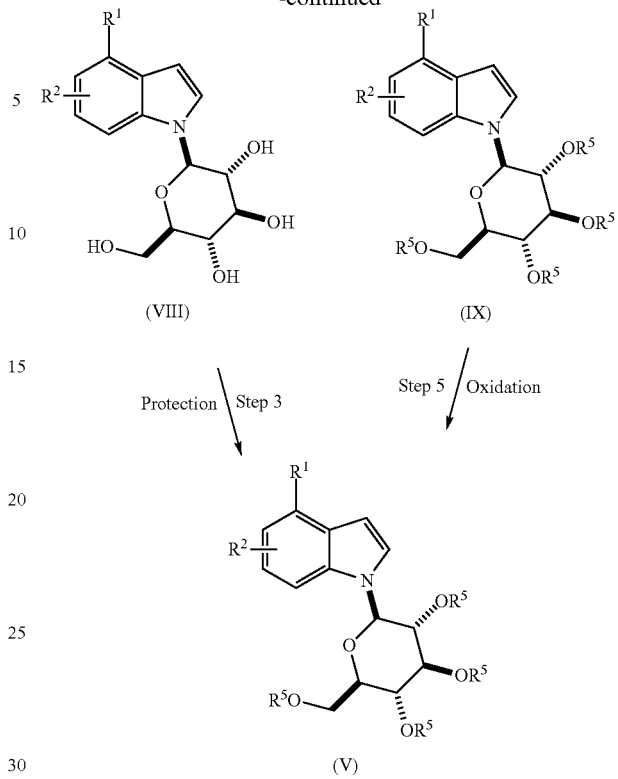

(in the above scheme, the symbols are the same as defined above.)

Step 1:

A compound of formula (X) can be prepared by condensing a compound of formula (XI) with D-glucose. The condensation reaction is typically carried out in a suitable solvent such as acetonitrile, water and alcohols (e.g., methanol, ethyl alcohol and 1-propanol) with or without catalysts such as ammonium chloride and acetic acid at ambient or elevated temperature.

Step 2:

A compound of formula (VIII) can be prepared by oxidation of the compound of formula (X). The oxidation reaction can be typically carried out in the presence of a oxidizing reagent such as palladium on charcoal, tetrachloro-1,4-benzoquinone (chloranil), 2,3-dichloro-5,6-dicyano-1,4-benzoquinone (DDQ) or ethylenebis(salicylimine)cobalt(II) salt in a suitable solvent such as ethers (e.g., diethylether, tetrahydrofuran, and 1,4-dioxane), halogenoalkanes (e.g., dichloromethane, chloroform, and 1,2-dichloroethane), water and a mixture of these solvents at ambient or lowered temperature.

Step 3:

A compound of formula (V) can be prepared by protecting hydroxy groups of the compound of formula (VIII). The protecting group for the hydroxy groups can be selected from those conventionally used as protecting groups for a hydroxy group. Examples of the protecting group for a hydroxy group include alkanoyl group (e.g., acetyl), arylalkyl group (e.g., benzyl, tolyl, and anisyl), alkylsilyl group (e.g., trimethylsilyl, t-butyldimethylsilyl, and triethylsilyl). The protection can be carried out by conventional methods well known to those skilled in the art. For a general description of protecting groups and their use, see T. W. Greene et al., "Protecting Groups in Organic Synthesis", John Wiley & Sons, New York, 1999.

Step 4:
A compound of formula (IX) can be prepared by protecting hydroxy groups of the compound (X) in accordance with Step 3.

Step 5:
A compound of formula (V) can be also prepared by oxidation of the compound (IX) in accordance with Step 2.

The compounds of formula (XI) can be prepared in accordance with the following scheme:

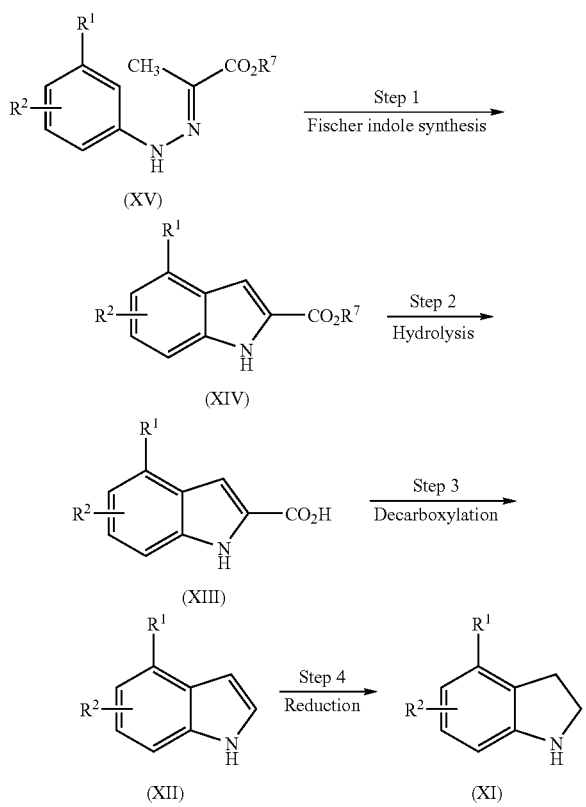

(In the above scheme, $R^7$ is alkyl, and the other symbols are the same as defined above.)

Step 1:
A compound of formula (XIV) can be prepared by cyclizing the compound of formula (XV). The cyclization reaction can be carried out according to Fischer indole synthesis well known in the art (cf.: Chem. Rev., 63, 373, 1963). This reaction is typically carried out in a suitable solvent such as alcohols (e.g. methanol and ethyl alcohol) and hydrocarbons (e.g., toluene, nitrobenzene) or without solvent with an acid such as Lewis acid (e.g., zinc chloride), inorganic acid (e.g., hydrochloric acid and polyphosphoric acid) and organic acid (e.g., acetic acid and trifluoroacetic acid) at elevated temperature.

Step 2:
A compound of formula (XIII) can be prepared by hydrolyzing the compound of formula (XIV). The hydrolysis reaction can be typically carried out in s suitable solvent such as water, alcohols (e.g., methanol and ethyl alcohol) and ethers (e.g., dioxane and tetrahydrofuran) with a base such as alkalimetal hydroxides (e.g., lithium hydroxide, potassium hydroxide and sodium hydroxide) at lowered, ambient or elevated temperature.

Step 3:
A compound of formula (XII) can be prepared by decarboxylation of the compound of formula (XIII). The decarboxylation can be typically carried out in a suitable solvent such as quinoline with a catalyst such as copper at elevated temperature.

Step 4:
A compound of formula (XI) can be prepared by reducing the compound of formula (XII). The reduction reaction can be typically carried out in a suitable solvent such as acetonitrile, halogenoalkanes (e.g., dichloromethane and dichloroethane) and ethers (e.g., diethyl ether and tetrahydrofuran) with a reducing agent such as triethylsilane, zinc borohydride in the presence of an acid include a Lewis acid such as trifluoroacetic acid, boron trifluoride.diethyl ether complex at ambient or elevated temperature.

A compound of formula (XV) can be prepared by condensing a compound of formula (XVI):

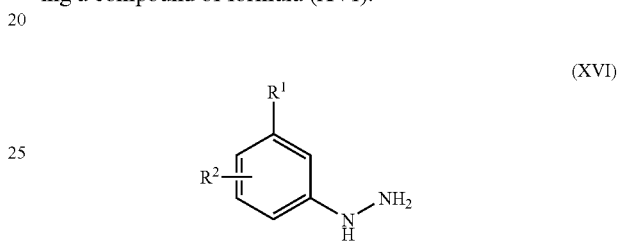

wherein the symbols are the same as defined above, with $CH_3COCO_2R^7$ wherein $R^7$ is as defined above. The condensation reaction can be typically carried out in a suitable solvent such as acetonitrile, water and alcohols (e.g., methanol, ethyl alcohol and 1-propanol) with or without a base (e.g., sodium acetate and potassium acetate), an acid (e.g., hydrochloric acid and acetic acid) at ambient or elevated temperature.

Alternatively, the compound of formula (XV) can be prepared by (1) reacting a compound of formula (XVII):

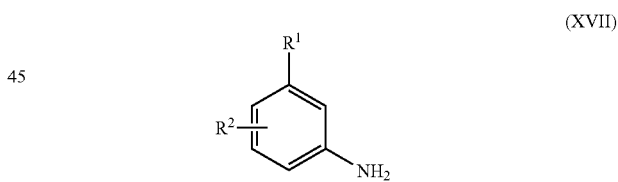

wherein the symbols are as defined above, with sodium nitrite in the presence of an acid such as hydrochloric acid in a suitable solvent such as water and alcohols (e.g., methanol and ethyl alcohol) at ambient or lowered temperature, to give a corresponding aryldiazonium salt, and (2) condensing the aryldiazonium salt with $CH_3COCH(CH_3)CO_2R^7$ wherein $R^7$ is as defined above, in the presence of a base such as sodium acetate, potassium hydroxide in a suitable solvent such as water and alcohols (e.g., methanol and ethyl alcohol) at lowered or ambient temperature.

The other starting compounds are commercially available or may be easily prepared by conventional methods well known to those skilled in the art.

Hereinafter, the present invention will be illustrated by Examples and Reference Examples, but the present invention should not be construed to be limited thereto.

EXAMPLES

Example 1

4-Chloro-3-(4-ethylphenylmethyl)-1-(β-D-glucopyranosyl)-indole (1) A mixture of 4-chloroindoline (2.88 g) and D-glucose (3.38 g) in ethyl alcohol (150 ml)-H$_2$O (10 ml) was refluxed under argon atmosphere overnight. The solvent was evaporated under reduced pressure and the residue was purified by silica gel column chromatography (chloroform:methanol=100:0-88:12) to give 4-chloro-1-(β-D-glucopyranosyl) indoline (3.35 g) as colorless foam. APCI-Mass m/Z 316/318 (M+H). $^1$H-NMR (DMSO-d6) δ 2.87-3.02 (m, 2H), 3.07-3.12 (m, 1H), 3.20-3.32 (m, 2H), 3.38-3.47 (m, 2H), 3.51-3.60 (m, 2H), 3.68-3.73 (m, 1H), 4.34-4.37 (m, 1H), 4.63 (d, J=8.3 Hz, 1H), 4.93 (d, J=5.1 Hz, 1H), 5.03 (d, J=4.0 Hz, 1H), 5.06 (d, J=4.5 Hz, 1H), 6.53 (d, J=8.0 Hz, 1H), 6.60 (d, J=8.0 Hz, 1H), 6.99 (t, J=7.9 Hz, 1H).

(2) The above compound (3.3 g) was dissolved in 1,4-dioxane (150 ml), and thereto was added 2,3-dichloro-5,6-dicyano-1,4-benzoquinone (2.85 g). The mixture was stirred at room temperature for 12 hours. To the reaction mixture was added a saturated aqueous sodium hydrogen carbonate solution (300 ml), the mixture was extracted with ethyl acetate 3 times. The combined organic layer was washed with a saturated aqueous sodium hydrogen carbonate solution and dried over magnesium sulfate. The insoluble materials were filtered off, and the filtrate was evaporated under reduced pressure. The residue was purified by silica gel column chromatography (chloroform:methanol=100:0-86:14) to give 4-chloro-1-(β-D-glucopyranosyl)indole (2.01 g) as pale brown crystals. APCI-Mass m/Z 314/316 (M+H). $^1$H-NMR (DMSO-d6) δ 3.24-3.50 (m, 4H), 3.68-3.74 (m, 2H), 4.54 (t, J=5.5 Hz, 1H), 5.11 (d, J=5.3 Hz, 1H), 5.20 (d, J=4.8 Hz, 1H), 5.28 (d, J=5.8 Hz, 1H), 5.44 (d, J=9.2 Hz, 1H), 6.51 (d, J=3.4 Hz, 1H), 7.11-7.16 (m, 2H), 7.57-7.58 (m, 2H).

(3) The above compound (2.01 g) was suspended in dichloromethane (100 ml), and thereto were added successively acetic anhydride (4.24 ml), N,N-diisopropylethylamine (7.8 ml) and 4-(dimethylamino)pyridine (78 mg). After being stirred at room temperature for 30 minutes, the mixture was washed successively with an aqueous citric acid solution, water and a saturated aqueous sodium hydrogen carbonate solution. The organic layer was dried over magnesium sulfate. The insoluble materials were filtered off, and the filtrate was evaporated under reduced pressure. The residue was purified by crystallization from diethyl ether-hexane to give 4-chloro-1-(2,3,4,6-tetra-O-acetyl-β-D-glucopyranosyl)-indole (2.94 g) as colorless crystals. APCI-Mass m/Z 499/501 (M+NH$_4$). $^1$H-NMR (DMSO-d6) δ 1.65 (s, 3H), 1.97 (s, 3H), 1.99 (s, 3H), 2.04 (s, 3H), 4.08-4.16 (m, 2H), 4.28-4.32 (m, 1H), 5.26 (t, J=9.8 Hz, 1H), 5.53 (t, J=9.5 Hz, 1H), 5.62 (t, J=9.3 Hz, 1H), 6.23 (d, J=9.2 Hz, 1H), 6.56 (d, J=3.4 Hz, 1H), 7.16 (d, J=8.2 Hz, 1H), 7.21 (t, J=7.9 Hz, 1H), 7.16 (d, J=3.5 Hz, 1H), 7.67 (d, J=8.2 Hz, 1H).

(4) To a stirred solution of the above compound (800 mg) and 4-ethylbenzoyl chloride (0.317 ml) in dichloromethane (30 ml) was added aluminum chloride (1.11 g) at 0° C. After being stirred at same temperature for 1 hour, the resultant mixture was poured into ice-water, and extracted with chloroform. The organic layer was washed with water and a saturated aqueous sodium hydrogen carbonate solution, and dried over magnesium sulfate. The insoluble materials were filtered off, and the filtrate was evaporated under reduced pressure. The residue was purified by silica gel column chromatography (hexane:ethyl acetate=90:10-55:45) to give 4-chloro-1-(2,3,4,6-tetra-O-acetyl-β-D-glucopyranosyl)-indol-3-yl 4-ethylphenyl ketone (970 mg) as colorless foam. APCI-Mass m/Z 614/616 (M+H). $^1$H-NMR (DMSO-d6) δ 1.24 (t, J=7.5 Hz, 3H), 1.70 (s, 3H), 1.97 (s, 3H), 1.98 (s, 3H), 2.04 (s, 3H), 2.72 (q, J=7.7 Hz, 2H), 4.10 (d, J=4.2 Hz, 2H), 4.27-4.31 (m, 1H), 5.29 (t, J=9.8 Hz, 1H), 5.53 (t, J=9.6 Hz, 1H), 5.73 (t, J=9.3 Hz, 1H), 6.33 (d, J=9.0 Hz, 1H), 7.27 (d, J=7.5 Hz, 1H), 7.36 (d, J=8.5 Hz, 1H), 7.39 (d, J=8.2 Hz, 2H), 7.76 (d, J=8.1 Hz, 2H), 7.79 (d, J=8.5 Hz, 1H), 8.11 (s, 1H).

(5) The above compound (960 mg) was dissolved in tetrahydrofuran (12 ml)-ethyl alcohol (6 ml), thereto was added sodium borohydride (592 mg). After being stirred at room temperature for 1.5 hours, the reaction mixture was poured into a cold 0.5 N aqueous hydrochloric acid solution (60 ml) and extracted with ethyl acetate twice. The combined organic layer was washed with a saturated aqueous sodium hydrogen carbonate solution, and dried over magnesium sulfate. The insoluble materials were filtered off, and the filtrate was evaporated under reduced pressure to give crude 4-chloro-1-(2,3,4,6-tetra-O-acetyl-β-D-gluco-pyranosyl)indol-3-yl 4-ethylphenyl methanol, which was used in the subsequent step without further purification.

(6) To a solution of the above compound in acetonitrile (10 ml)-dichloromethane (20 ml) were added triethylsilane (1.25 ml) and boron trifluoride.diethyl ether complex (0.99 ml) at 0° C. under argon atmosphere. After being stirred at same temperature for 15 minutes, thereto was added a saturated aqueous sodium hydrogen carbonate solution, and the organic solvent was evaporated under reduced pressure. The residue was extracted with ethyl acetate twice, and the combined organic layer was dried over magnesium sulfate. The insoluble materials were filtered off, and the filtrate was evaporated under reduced pressure to give crude 4-chloro-3-(4-ethylphenylmethyl)-1-(2,3,4,6-tetra-O-acetyl-β-D-glucopyranosyl)indole, which was partially deacetylated. This crude compound was dissolved in chloroform (30 ml), and thereto were added successively acetic anhydride (0.673 ml), triethylamine (0.871 ml) and 4-(dimethylamino)pyridine (a catalytic amount). After being stirred at room temperature for 30 minutes, the reaction mixture was washed successively an aqueous citric acid solution, brine and a saturated aqueous sodium hydrogen carbonate solution, and dried over magnesium sulfate. The insoluble materials were filtered off, and the filtrate was evaporated under reduced pressure. The residue was purified by silica gel column chromatography (hexane:ethyl acetate=85:15-60:40) to give 4-chloro-3-(4-ethylphenylmethyl)-1-(2,3,4,6-tetra-O-acetyl-β-D-glucopyranosyl) indole (514 mg) as colorless crystals. APCI-Mass m/Z 617/619 (M+NH$_4$). $^1$H-NMR (DMSO-d6) δ 1.15 (t, J=7.6 Hz, 3H), 1.65 (s, 3H), 1.96 (s, 3H), 1.99 (s, 3H), 2.04 (s, 3H), 2.55 (q, J=7.7 Hz, 2H), 4.08-4.15 (m, 2H), 4.19 (d, J=3.1 Hz, 2H), 4.26-4.30 (m, 1H), 5.24 (t, J=9.6 Hz, 1H), 5.50 (t, J=9.4 Hz, 1H), 5.55 (t, J=9.2 Hz, 1H), 6.17 (d, J=8.8 Hz, 1H), 7.04-7.10 (m, 5H), 7.16 (t, J=7.9 Hz, 1H), 7.27 (s, 1H), 7.64 (d, J=8.3 Hz, 1H).

(7) The above compound (510 mg) was dissolved in tetrahydrofuran (10 ml)-methanol (5 ml), and thereto was added sodium methoxide (28% methanol solution, 3 drops). After being stirred al room temperature for 30 minutes, the solvent was evaporated under reduced pressure. The residue was purified by silica gel column chromatography (chloroform:methanol=100:0-90:10) to give the titled compound, 4-chloro-3-(4-ethylphenylmethyl)-1-(β-D-glucopyranosyl) indole (337 mg) as colorless foam. APCI-Mass m/Z 432/434 (M+H). $^1$H-NMR (DMSO-d6) δ 1.15 (t, J=7.5 Hz, 3H), 2.55 (q, J=7.7 Hz, 2H), 3.21-3.47 (m, 4H), 3.62-3.70 (m, 2H), 4.23

(s, 2H), 4.53 (t, J=5.5 Hz, 1H), 5.09 (d, J=5.3 Hz, 1H), 5.16 (d, J=5.0 Hz, 1H), 5.20 (d, J=5.9 Hz, 1H), 5.40 (d, J=9.0 Hz, 1H), 7.02 (d, J=7.5 Hz, 1H), 7.08-7.15 (m, 5H), 7.24 (s, 1H), 7.53 (d, J=8.2 Hz, 1H).

Example 2

3-(4-Ethylphenylmethyl)-4-fluoro-1-(β-D-glucopyranosyl)-indole (1) A mixture of 4-fluoroindoline (185 mg) and D-glucose (267 mg) in $H_2O$ (0.74 ml)-ethyl alcohol (9 ml) was refluxed under argon atmosphere for 24 hours. The solvent was evaporated under reduced pressure to give crude 4-fluoro-1-(β-D-glucopyranosyl)indoline, which was used in the subsequent step without further purification.

(2) The above compound was suspended in chloroform (8 ml), and thereto were added successively pyridine (0.873 ml), acetic anhydride (1.02 ml) and 4-(dimethylamino)pyridine (a catalytic amount). After being stirred at room temperature for 21 hour, the reaction solvent was evaporated under reduced pressure. The residue was dissolved in ethyl acetate, and the solution was washed with a 10% aqueous copper(II) sulfate solution twice and a saturated aqueous sodium hydrogen carbonate solution, and dried over magnesium sulfate. The insoluble materials were filtered off, and the filtrate was evaporated under reduced pressure. The residue was purified by silica gel column chromatography (hexane:ethyl acetate=90:10-60:40) to give 4-fluoro-1-(2,3,4,6-tetra-O-acetyl-β-D-glucopyranosyl)indoline (365 mg) as colorless amorphous. APCI-Mass m/Z 468 (M+H). $^1$H-NMR (DMSO-d6) δ 1.93 (s, 3H), 1.96 (s, 3H), 1.97 (s, 3H), 2.00 (s, 3H), 2.83 (ddd, J=15.5, 10.5, 10.3 Hz, 1H), 2.99-3.05 (m, 1H), 3.49-3.57 (m, 2H), 3.95-3.99 (m, 1H), 4.07-4.11 (m, 2H), 4.95 (t, J=9.5 Hz, 1H), 5.15 (t, J=9.4 Hz, 1H), 5.42 (t, J=9.6 Hz, 1H), 5.49 (d, J=9.3 Hz, 1H), 6.48 (t, J=8.6 Hz, 1H), 6.60 (d, J=8.0 Hz, 1H), 7.05-7.10 (m, 1H).

(3) The above compound (348 mg) was dissolved in 1,4-dioxane (14 ml), and thereto was added 2,3-dichloro-5,6-dicyano-1,4-benzoquinone (306 mg). After being stirred at room temperature for 33 hours, thereto was added a saturated aqueous sodium hydrogen carbonate solution (20 ml), and the organic solvent was evaporated under reduced pressure. The residue was extracted with ethyl acetate twice, and the combined organic layer was washed with brine, dried over magnesium sulfate and treated with activated carbon. The insoluble materials were filtered off, and the filtrate was evaporated under reduced pressure. The residue was purified by silica gel column chromatography (hexane:ethyl acetate=90:10-60:40) and recrystallization from ethyl alcohol to give 4-fluoro-1-(2,3,4,6-tetra-O-acetyl-β-D-glucopyranosyl)indole (313 mg, as colorless crystals. mp 132-135° C. APCI-Mass m/Z 483 (M+$NH_4$). $^1$H-NMR (DMSO-d6) δ 1.64 (s, 3H), 1.97 (s, 3H), 1.99 (s, 3H), 2.04 (s, 3H), 4.10 (ABX, J=12.4, 2.7 Hz, 1H), 4.14 (ABX, J=12.4, 5.2 Hz, 1H), 4.31 (ddd, J=10.0, 5.2, 2.7 Hz, 1H), 5.25 (t, J=9.7 Hz, 1H), 5.53 (t, J=9.5 Hz, 1H), 5.61 (t, J=9.3 Hz, 1H), 6.22 (d, J=9.0 Hz, 1H), 6.58 (d, J=3.4 Hz, 1H), 6.88 (dd, J=10.8, 7.9 Hz, 1H), 7.19 (td, J=8.1, 5.3 Hz, 1H), 7.51 (d, J=8.5 Hz, 1H), 7.53 (d, J=3.4 Hz, 1H).

(4) To a stirred solution of the above compound (301 mg) and 4-ethylbenzoyl chloride (0.124 ml) in dichloromethane (12 ml) was added aluminum chloride (431 mg) at 0° C. After being stirred at same temperature for 1 hour, the resultant mixture was poured into ice-water (15 ml), and extracted with chloroform twice. The combined organic layer was washed with water and a saturated aqueous sodium hydrogen carbonate solution (15 ml), and dried over magnesium sulfate. The insoluble materials were filtered off, and the filtrate was evaporated under reduced pressure. The residue was purified by silica gel column chromatography (hexane ethyl acetate=90:10-55:45) to give 4-ethylphenyl 4-fluoro-1-(2,3,4,6-tetra-O-acetyl-β-D-glucopyranosyl)indol-3-yl ketone (378 mg) as colorless foam. APCI-Mass m/Z 598 $^1$H-NMR (DMSO-d6) δ 1.25 (t, J=7.5 Hz, 3H), 1.69 (s, 3H), 1.97 (s, 3H), 1.98 (s, 3H), 2.04 (s, 3H), 2.73 (q, J=7.5 HZ, 2H), 4.07-4.12 (m, 2H), 4.27-4.30 (m, 1H), 5.31 (t, J=9.8 Hz, 1H), 5.53 (t, J=9.6 Hz, 1H), 5.77 (t, J=9.3 Hz, 1H), 6.34 (d, J=9.0 Hz, 1H), 7.03 (dd, J=10.8, 8.0 Hz, 1H), 7.38 (td, J=8.2, 5.1 Hz, 1H), 7.41 (d, J=7.9 Hz, 2H), 7.63 (d, J=8.3 Hz, 1H), 7.77 (d, J=8.2 Hz, 2H), 8.16 (s, 1H).

(5) To a stirred solution of the above compound (375 mg) in ethyl alcohol (4 ml)-tetrahydrofuran (8 ml) were added cerium(III) chloride heptahydrate (701 mg) and sodium borohydride (71.2 mg) at 0° C. After being stirred at the same temperature for 1 hour, thereto was added a 0.5 N aqueous hydrochloric acid solution, and the mixture was extracted with ethyl acetate twice. The combined organic layer was washed with a saturated aqueous sodium hydrogen carbonate solution and dried over magnesium sulfate. The insoluble materials were filtered off, and the filtrate was evaporated under reduced pressure to give crude 4-ethylphenyl 4-fluoro-1-(2,3,4,6-tetra-O-acetyl-β-D-glucopyranosyl)-indol-3-yl methanol, which was used in the subsequent step without further purification.

(6) To a stirred solution of the above compound in acetonitrile (8 ml)-dichloromethane (4 ml) were added triethylsilane (0.501 ml) and boron trifluoride.diethyl ether complex (0.398 ml) at −10° C. under argon atmosphere. After being stirred at same temperature for 10 minutes, thereto was added a saturated aqueous sodium hydrogen carbonate solution, and the organic solvent was evaporated under reduced pressure. The residue was extracted with ethyl acetate twice, and the combined organic layer was dried over magnesium sulfate. The insoluble materials were filtered off, and the filtrate was evaporated under reduced pressure to give crude 3-(4-ethylphenylmethyl)-4-fluoro-1-(2,3,4,6-tetra-O-acetyl-β-D-glucopyranosyl)indole, which was partially deacetylated. This crude compound was dissolved in chloroform (11 ml), and thereto were added successively pyridine (0.152 ml), acetic anhydride (0.178 ml) and 4-(dimethylamino)pyridine (7.7 mg). After being stirred at room temperature for 1 hour, the solvent was evaporated under reduced pressure. The residue was dissolved in ethyl acetate (40 ml), and the mixture was washed with a 10% aqueous copper(II) sulfate solution twice and a saturated aqueous sodium hydrogen carbonate solution, and dried over magnesium sulfate. The insoluble materials were filtered off, and the filtrate was evaporated under reduced pressure. The residual solid was triturated with ethyl alcohol under heating to give 3-(4-ethyl-phenylmethyl)-4-fluoro-1-(2,3,4,6-tetra-O-acetyl-β-D-glucopyranosyl)indole (335 mg) as colorless crystals. mp 188-189° C. APCI-Mass m/Z 601 (M+$NH_4$). $^1$H-NMR (DMSO-d6) δ 1.14 (t, J=7.6 Hz, 3H), 1.63 (s, 3H), 1.96 (s, 3H), 1.99 (s, 3H), 2.04 (s, 3H), 2.54 (q, J=7.5 Hz, 2H), 4.02 (s, 2H), 4.09 (ABX, J=12.4, 2.4 Hz, 1H), 4.13 (ABX, J=12.4, 5.4 Hz, 1H), 4.29 (ddd, J=9.9, 5.2, 2.7 Hz, 1H), 5.23 (t, J=9.6 Hz, 1H), 5.49-5.56 (m, 2H), 6.15 (d, J=8.5 Hz, 1H), 6.17 (dd, J=10.9, 7.9 Hz, 1H), 7.09 (s, 4H), 7.14 (td, J=8.0, 5.3 Hz, 1H), 7.24 (s, 1H), 7.46 (d, J=8.2 Hz, 1H).

(7) The above compound (321 mg) was dissolved in methanol (3 ml)-tetrahydrofuran (6 ml), thereto was added sodium methoxide (28% methanol solution, 1 drop). After being stirred at room temperature for 3 hours, the reaction solvent was evaporated under reduced pressure. The residue was purified by silica gel column chromatography (chloroform:methanol=100:0-90:10) to give the titled compound, 3-(4-ethylphenylmethyl)-4-fluoro-1-(β-D-glucopyranosyl)indole (226 mg) as colorless foam. APCI-Mass m/Z 433 (M+NH$_4$). $^1$H-NMR (DMSO-d6) δ 1.14 (t, J=7.6 Hz, 3H), 2.54 (q, J=7.6 Hz, 2H), 3.21-3.27 (m, 1H), 3.35-3.48 (m, 3H), 3.62-3.70 (m, 2H), 4.04 (s, 2H), 4.54 (t, J=5.6 Hz, 1H), 5.10 (d, J=5.3 Hz, 1H), 5.18 (d, J=4.9 Hz, 1H), 5.21 (d, J=5.9 Hz, 1H), 5.37 (d, J=9.2 Hz, 1H), 6.74 (dd, J=11.3, 7.6 Hz, 1H), 7.03-7.08 (m, 1H), 7.09 (d, J=8.2 Hz, 2H), 7.17 (d, J=8.1 Hz, 2H), 7.22 (s, 1H), 7.35 (d, J=8.4 Hz, 1H).

Example 3

4-Chloro-3-(4-ethoxyphenylmethyl)-1-(β-D-glucopyranosyl)-indole (1) 4-Chloro-1-(2,3,4,6-tetra-O-acetyl-β-D-glucopyranosyl)-indole obtained in Example 1-(3) and 4-ethoxybenzoyl chloride were treated in a manner similar to Example 2-(4) to give 4-chloro-1-(2,3,4,6-tetra-O-acetyl-β-D-glucopyranosyl)-indol-3-yl 4-ethoxyphenyl ketone as a colorless powder. APCI-Mass m/Z 630/632 (M+H). $^1$H-NMR (DMSO-d6) δ 1.37 (t, J=7.0 Hz, 3H), 1.69 (s, 3H), 1.98 (s, 6H), 2.04 (s, 3H), 4.11-4.12 (m, 2H), 4.14 (q, J=7.3 Hz, 2H), 4.28-4.32 (m, 1H), 5.29 (t, J=9.7 HZ, 1H), 5.54 (t, J=9.5 Hz, 1H), 5.71 (t, J=9.2 Hz, 1H), 6.32 (d, J=9.0 Hz, 1H), 7.04 (d, J=8.8 Hz, 2H), 7.25 (d, J=7.5 Hz, 1H), 7.35 (t, J=8.0 Hz, 1H), 7.79 (d, 1H), 7.99 (d, J=8.8 Hz, 2H), 8.07 (s, 1H).

(2) The above 4-chloro-1-(2,3,4,6-tetra-O-acetyl-β-D-gluco-pyranosyl)-indol-3-yl 4-ethoxyphenyl ketone (500 mg) was treated in a manner similar to Example 2-(5) to give crude 4-chloro-1-(2,3,4,6-tetra-O-acetyl-β-D-glucopyranosyl)indol-3-yl 4-ethoxyphenyl methanol, which was used in the subsequent step without further purification.

(3) To a stirred solution of the above compound in acetonitrile (10 ml)-dichloromethane (5 ml) were added triethylsilane (0.634 ml) and boron trifluoride.diethyl ether complex (0.503 ml) at −10° C. under argon atmosphere. After being stirred at same temperature for 40 minutes, thereto was added a saturated aqueous sodium hydrogen carbonate solution (20 ml), and the organic solvent was evaporated under reduced pressure. The residue was extracted with ethyl acetate (30 ml) twice, and the combined organic layer was dried over magnesium sulfate. The insoluble materials were filtered off, and the filtrate was evaporated under reduced pressure. The residual crystal was recrystallized from ethyl alcohol (8 ml) to give 4-chloro-3-(4-ethoxyphenylmethyl)-1-(2,3,4,6-tetra-O-acetyl-β-D-glucopyranosyl)indole (430 mg) as colorless needles. mp 166-169° C. APCI-Mass m/Z 633/635 (M+NH$_4$). $^1$H-NMR (DMSO-d6) δ 1.30 (t, J=7.0 Hz, 3H), 1.65 (s, 3H), 1.96 (s, 3H), 1.99 (s, 3H), 2.04 (s, 3H), 3.96 (q, J=6.9 Hz, 2H), 4.09 (A part of ABX, J=12.4, 2.6 Hz, 1H), 4.13 (B part of ABX, J=12.5, 5.3 Hz, 1H), 4.14 and 4.16 (ABq, J=16.0 Hz, 2H), 4.28 (ddd, J=9.9, 5.3 and 2.8, 1H), 5.23 (t, J=9.6 Hz, 1H), 5.50 (t, J=9.2 Hz, 1H), 5.54 (t, J=9.0 Hz, 1H), 6.16 (d, J=8.7 Hz, 1H), 6.80 (d, J=8.5 Hz, 2H), 7.04-7.06 (m, 3H), 7.16 (t, J=7.9 Hz, 1H), 7.22 (s, 1H), 7.64 (d, J=8.2 Hz, 1H).

(4) The above 4-chloro-3-(4-ethoxyphenylmethyl)-1-(2,3,4,6-tetra-O-acetyl-β-D-glucopyranosyl)indole was treated in a manner similar to Example 2-(7) to give the titled compound, 4-chloro-3-(4-ethoxyphenylmethyl)-1-(β-D-glucopyranosyl)-indole as a colorless powder. APCI-Mass m/Z 465/467 (M+NH$_4$). $^1$H-NMR (DMSO-d6) δ 1.30 (t, J=6.9 Hz, 3H), 3.23 (td, J=8.9, 5.5 Hz, 1H), 3.39 (td, J=8.8, 5.1 Hz, 1H), 3.43-3.41 (m, 2H), 3.61-3.69 (m, 2H), 3.97 (q, J=6.9 Hz, 2H), 4.19 (s, 2H), 4.53 (t, J=5.5 Hz, 1H), 5.09 (d, J=5.3 Hz, 1H), 5.15 (d, J=5.0 Hz, 1H), 5.20 (d, J=5.8 Hz, 1H), 5.39 (d, J=9.0 Hz, 1H), 6.82 (d, J=8.7 Hz, 2H), 7.02 (d, J=7.5 Hz, 1H), 7.09 (t, J=8.0 Hz, 1H), 7.12 (d, J=8.5 Hz, 2H), 7.20 (s, 1H), 7.53 (d, J=8.3 Hz, 1H).

Example 4

4-Chloro-3-(4-(methylthio)phenylmethyl)-1-(β-D-gluco-pyranosyl)indole

4-Chloro-1-(2,3,4,6-tetra-O-acetyl-β-D-glucopyranosyl)indole obtained in Example 1-(3) and 4-(methylthio)benzoyl chloride were treated in a manner similar to Example 3 to give the titled compound as a colorless powder. APCI-Mass m/Z 450/452 (M+H). $^1$H-NMR (DMSO-d6) δ 2.43 (s, 3H), 3.24 (td, J=9.0, 5.6 Hz, 1H), 3.39 (td, J=8.7, 5.2 Hz, 1H), 3.43-3.48 (m, 2H), 3.62-3.69 (m, 2H), 4.23 (s, 2H), 4.53 (t, J=5.4 Hz, 1H), 5.09 (d, J=5.1 Hz, 1H), 5.16 (d, J=5.0 Hz, 1H), 5.21 (d, J=5.6 Hz, 1H), 5.40 (d, J=9.1 Hz, 1H), 7.02 (d, J=7.5 Hz, 1H), 7.10 (t, J=7.9 Hz, 1H), 7.17 (s, 4H), 7.27 (s, 1H), 7.54 (d, J=8.2 Hz, 1H).

Example 5

4-Chloro-3-(4-methoxyphenylmethyl)-1-(β-D-glucopyranosyl)-indole

4-Chloro-1-(2,3,4,6-tetra-O-acetyl-β-D-glucopyranosyl) indole obtained in Example 1-(3) and 4-methoxybenzoyl chloride were treated in a manner similar to Example 3 to give the titled compound as a colorless powder. APCI-Mass m/Z 434/436 (M+H). $^1$H-NMR (DMSO-d6) δ 3.20-3.27 (m, 1H), 3.36-3.48 (m, 3H), 3.60-3.71 (m, 2H), 3.71 (s, 3H), 4.20 (s, 2H), 4.53 (t, J=5.6 Hz, 1H), 5.10 (d, J=5.1 Hz, 1H), 5.16 (d, J=5.0 Hz, 1H), 5.21 (d, J=5.6 Hz, 1H), 5.40 (d, J=9.0 Hz, 1H), 6.84 (d, J=8.7 Hz, 2H), 7.03 (d, J=7.6 Hz, 1H), 7.09 (t, J=7.9 Hz, 1H), 7.15 (d, J=8.7 Hz, 2H), 7.20 (s, 1H), 7.54 (d, J=8.2 Hz, 1H).

Example 6

4-Chloro-3-(4-chlorophenylmethyl)-1-(β-D-glucopyranosyl)-indole (1) 4-Chloro-1-(2,3,4,6-tetra-O-acetyl-β-D-glucopyranosyl)-indole obtained in Example 1-(3) and 4-chlorobenzoyl chloride were treated in a manner similar to Example 2-(4) to give 4-chloro-1-(2,3,4,6-tetra-O-acetyl-β-D-glucopyranosyl)-indol-3-yl 4-chlorophenyl ketone as a colorless powder. APCI-Mass m/Z 620/622 (M+H). $^1$H-NMR (DMSO-d6) δ 1.69 (s, 3H), 1.97 (s, 3H), 1.98 (s, 3H), 2.04 (s, 3H), 4.11 (br-d, J=4.2 Hz, 2H), 4.30 (m, 1H), 5.28 (t, J=9.8 Hz, 1H), 5.53 (t, J=9.6 Hz, 1H), 5.73 (t, J=9.4 Hz, 1H), 6.34 (d, J=9.2 Hz, 1H), 7.29 (d, J=7.7 Hz, 1H), 7.38 (t, J=8.0 Hz, 1H), 7.62 (d, J=8.5 Hz, 2H), 7.80 (d, J=8.5 Hz, 1H), 7.82 (d, J=8.5 Hz, 2H), 8.18 (s, 1H).

(2) The above 4-chloro-1-(2,3,4,6-tetra-O-acetyl-β-D-gluco-pyranosyl)indol-3-yl 4-chlorophenyl ketone was treated in a manner similar to Example 2-(5) to give crude 4-chloro-1-(2,3,4,6-tetra-O-acetyl-β-D-glucopyranosyl)indol-3-yl 4-chlorophenyl methanol, which was used in the subsequent step without further purification.

(3) The above compound was treated in a manner similar to Example 3-(3) to give 4-chloro-3-(4-chlorophenylmethyl)-1-(2,3,4,6-tetra-O-acetyl-β-D-glucopyranosyl)indole as colorless crystals. mp 214-216° C. APCI-Mass m/Z 623/625 (M+NH$_4$). $^1$H-NMR (DMSO-d6) δ 1.65 (s, 3H), 1.96 (s, 3H), 1.99 (s, 3H), 2.04 (s, 3H), 4.10 (dd, J=12.5, 2.6 Hz, 1H), 4.14 (dd, J=12.5, 5.3 Hz, 1H), 4.20 (d, J=15.9 Hz, 1H), 4.26 (d, J=16.5 Hz, 1H), 4.28 (m, 1H), 5.24 (t, J=9.4 Hz, 1H), 5.56 (t, J=9.2 Hz, 1H), 6.18 (d, J=8.7 Hz, 1H), 7.06 (d, J=7.5 Hz, 1H), 7.16 (d, J=8.5 Hz, 2H), 7.17 (t, J=8.0 Hz, 1H), 7.31 (d, J=8.5 Hz, 2H), 7.33 (s, 1H), 7.65 (d, J=8.3 Hz, 1H).

(4) The above 4-chloro-3-(4-chlorophenylmethyl)-1-(2,3,4,6-tetra-O-acetyl-β-D-glucopyranosyl) indole was treated in a manner similar to Example 2-(7) to give the titled compound, 4-chloro-3-(4-chlorophenylmethyl)-1-(β-D-glucopyranosyl)-indole as a colorless powder. APCI-Mass m/Z 438/440 (M+H). $^1$H-NMR (DMSO-d6) δ 3.25 (m, 1H), 3.35-3.49 (m, 3H), 3.63-3.72 (m, 2H), 4.26 (s, 2H), 4.53 (t, J=5.5 Hz, 1H), 5.10 (d, J=5.3 Hz, 1H), 5.17 (d, J=4.8 Hz, 1H), 5.22 (d, J=5.8 Hz, 1H), 5.40 (d, J=9.2 Hz, 1H), 7.02 (d, J=7.5 Hz, 1H), 7.10 (t, J=7.9 Hz, 1H), 7.23 (d, J=8.3 Hz, 2H), 7.32 (d, J=8.3 Hz, 2H), 7.33 (s, 1H), 7.55 (d, J=8.2 Hz, 1H).

Example 7

3-(5-Bromo-2-thienylmethyl)-4-chloro-1-(β-D-glucopyranosyl)-indole (1) 4-Chloro-1-(2,3,4,6-tetra-O-acetyl-β-D-glucopyranosyl)-indole obtained in Example 1-(3) and 5-bromothiophene-2-carbonyl chloride were treated in a manner similar to Example 2-(4) to give 4-chloro-1-(2,3,4,6-tetra-O-acetyl-β-D-glucopyranosyl)-indol-3-yl 5-bromo-2-thienyl ketone as a yellow powder. APCI-Mass m/Z 670/672 (M+H). $^1$H-NMR (DMSO-d6) δ 1.67 (s, 3H), 1.97 (s, 3H), 1.99 (s, 3H), 2.05 (s, 3H), 4.11 (d, J=4.0 Hz, 2H), 4.30 (ddd, J=9.8, 4.2 and 3.9 Hz, 1H), 5.30 (t, J=9.8 Hz, 1H), 5.55 (t, J=9.6 Hz, 1H), 5.81 (t, J=9.3 Hz, 1H), 6.36 (d, J=9.0 Hz, 1H), 7.30 (d, J=7.5 Hz, 1H), 7.39 (t, J=8.0 Hz, 1H), 7.47 (d, J=3.9 Hz, 1H), 7.53 (d, J=4.0 Hz, 1H), 7.78 (d, J=8.3 Hz, 1H), 8.46 (s, 1H).

(2) The above 4-chloro-1-(2,3,4,6-tetra-O-acetyl-β-D-gluco-pyranosyl)indol-3-yl 5-bromo-2-thienyl ketone was treated in a manner similar to Example 2-(5) to give crude 4-chloro-1-(2,3,4,6-tetra-O-acetyl-β-D-glucopyranosyl)indol-3-yl 5-bromo-2-thienyl methanol, which was used in the subsequent step without further purification.

(3) The above compound was treated in a manner similar to Example 3-(3) to give 3-(5-bromo-2-thienylmethyl)-4-chloro-1-(2,3,4,6-tetra-O-acetyl-β-D-glucopyranosyl)indole as pale yellow crystals. mp 185-187° C. APCI-Mass m/Z 673/675 (M+NH$_4$). $^1$H-NMR (DMSO-d6) δ 1.66 (s, 3H), 1.96 (s, 3H), 1.99 (s, 3H), 2.09 (s, 3H), 4.10 (A part of ABX, J=12.4, 2.5 Hz, 1H), 4.14 (B part of ABX, J=12.4, 5.3 Hz, 1H), 4.29 (ddd, J=9.9, 5.3 and 2.7 Hz, 1H), 4.33 and 4.39 (ABq, J=16.5 Hz, 2H), 5.25 (t, J=9.6 Hz, 1H), 5.51 (t, J=9.4 Hz, 1H), 5.57 (t, J=9.2 Hz, 1H), 6.20 (d, J=8.8 Hz, 1H), 6.63 (d, J=3.7 Hz, 1H), 7.01 (d, J=3.7 Hz, 1H), 7.09 (d, J=7.5 Hz, 1H), 7.19 (d, J=8.0 Hz, 1H), 7.47 (s, 1H), 7.67 (d, J=8.3 Hz, 1H).

(4) The above 3-(5-bromo-2-thienylmethyl)-4-chloro-1-(2,3,4,6-tetra-O-acetyl-β-D-glucopyranosyl)indole was treated in a manner similar to Example 2-(7) to give the titled compound, 3-(5-bromo-2-thienylmethyl)-4-chloro-1-(β-D-gluco-pyranosyl)indole as a pale yellow powder. APCI-Mass m/Z 505/507 (M+NH$_4$). $^1$H-NMR (DMSO-d6) δ 3.26 (td, J=9.1, 5.7 Hz, 1H), 3.40 (td, J=8.8 Hz, 1H), 3.45-3.49 (m, 2H), 3.64-3.70 (m, 2H), 4.39 (s, 2H), 4.54 (t, J=5.5 Hz, 1H), 5.11 (d, J=5.3 Hz, 1H), 5.18 (d, J=5.0 Hz, 1H), 5.22 (d, J=5.8 Hz, 1H), 5.42 (d, J=9.0 Hz, 1H), 6.08 (d, J=3.7 Hz, 1H), 7.01 (d, J=3.7 Hz, 1H), 7.06 (d, J=9.0 Hz, 1H), 7.12 (t, J=7.9 Hz, 1H), 7.46 (s, 1H), 7.56 (d, J=8.0 Hz, 1H).

Example 8

3-(4-Ethoxyphenylmethyl)-4-fluoro-1-(β-D-glucopyranosyl)-indole (1) 4-Fluoro-1-(2,3,4,6-tetra-O-acetyl-β-D-glucopyranosyl)-indole obtained in Example 2-(3) and 4-ethoxybenzoyl chloride were treated in a manner similar to Example 2-(4) to give 4-ethoxyphenyl 4-fluoro-1-(2,3,4,6-tetra-O-acetyl-β-D-gluco-pyranosyl)indol-3-yl ketone as a colorless powder. APCI-Mass m/Z 614 (M+H). $^1$H-NMR (DMSO-d6) δ 1.38 (t, J=6.9 Hz, 3H), 1.68 (s, 3H), 1.97 (s, 3H), 1.98 (s, 3H), 2.04 (s, 3H), 4.11 (d, J=4.0 Hz, 2H), 4.16 (q, J=7.0 Hz, 2H), 4.28-4.31 (m, 1H), 5.30 (t, J=9.8 Hz, 1H), 5.54 (t, J=9.6 Hz, 1H), 5.76 (t, J=9.3 Hz, 1H), 6.34 (d, J=9.0 Hz, 1H), 7.01 (dd, J=10.6, 8.0 Hz, 1H), 7.07 (d, J=8.7 Hz, 2H), 7.36 (td, J=8.1, 4.9 Hz, 1H), 7.62 (d, J=8.3 Hz, 1H), 7.83 (d, J=8.8 Hz, 2H), 8.14 (s, 1H).

(2) The above 4-ethoxyphenyl 4-fluoro-1-(2,3,4,6-tetra-O-acetyl-β-D-glucopyranosyl)indol-3-yl ketone was treated in a manner similar to Example 2-(5) to give crude 4-ethoxyphenyl 4-fluoro-1-(2,3,4,6-tetra-O-acetyl-β-D-glucopyranosyl)-indol-3-yl methanol, which was used in the subsequent step without further purification.

(3) The above compound was treated in a manner similar to Example 3-(3) to give 3-(4-ethoxyphenylmethyl)-4-fluoro-1-(2,3,4,6-tetra-O-acetyl-β-D-glucopyranosyl)indole as colorless needles. mp 146-148° C. APCI-Mass m/Z 617 (M+NH$_4$). $^1$H-NMR (DMSO-d6) δ 1.29 (t, J=7.0 Hz, 3H), 1.64 (s, 3H), 1.96 (s, 3H), 1.99 (s, 3H), 2.04 (s, 3H), 3.96 (q, J=7.1 Hz, 2H), 3.98 (s, 2H), 4.09 (ABX, J=12.4, 2.6 Hz, 1H), 4.13 (ABX, J=12.4, 5.4 Hz, 1H), 4.28 (ddd, J=9.9, 5.2, 2.7 Hz, 1H), 5.22 (t, J=9.5 Hz, 1H), 5.48-5.56 (m, 2H), 6.14 (d, J=8.5 Hz, 1H), 6.77 (dd, J=10.8, 7.7 Hz, 1H), 6.80 (d, J=8.5 Hz, 2H), 7.08 (d, J=3.5 Hz, 2H), 7.14 (td, J=8.0, 5.3 Hz, 1H), 7.21 (s, 1H), 7.46 (d, J=8.2 Hz, 1H).

(4) The above 3-(4-ethoxyphenylmethyl)-4-fluoro-1-(2,3,4,6-tetra-O-acetyl-β-D-glucopyranosyl)indole was treated in a manner similar to Example 2-(7) to give the titled compound, 3-(4-ethoxyphenylmethyl)-4-fluoro-1-(β-D-glucopyranosyl)indole as a colorless powder. APCI-Mass m/Z 449 (M+NH$_4$). $^1$H-NMR (DMSO-d6) δ 1.29 (t, J=7.0 Hz, 3H), 3.21-3.27 (m, 1H), 3.35-3.48 (m, 3H), 3.65 (td, J=9.2, 5.5 Hz, 2H), 3.96 (q, J=7.0 Hz, 2H), 4.01 (s, 2H), 4.53 (t, J=5.6 Hz, 1H), 5.10 (d, J=5.3 Hz, 1H), 5.17 (d, J=5.1 Hz, 1H), 5.21 (d, J=5.7 Hz, 1H), 5.36 (d, J=9.0 Hz, 1H), 6.74 (dd, J=11.2, 7.7 Hz, 1H), 6.81 (d, J=8.8 Hz, 2H), 7.06 (td, J=8.1, 5.2 Hz, 1H), 7.15 (d, J=8.6 Hz, 2H), 7.19 (s, 1H), 7.35 (d, J=8.4 Hz, 1H).

Example 9

4-Fluoro-3-(4-methoxyphenylmethyl)-1-(β-D-glucopyranosyl)-indole

4-Fluoro-1-(2,3,4,6-tetra-O-acetyl-β-D-glucopyranosyl) indole obtained in Example 2-(3) and 4-methoxybenzoyl chloride were treated in a manner similar to Example 3 to give the titled compound as a colorless powder. APCI-Mass m/Z 435 (M+NH$_4$)H. $^1$H-NMR (DMSO-d6) δ 3.21-3.26 (m, 1H), 3.37-3.46 (m, 3H), 3.63-3.68 (m, 2H), 3.70 (s, 3H), 4.02 (s, 2H), 4.53 (t, J=5.4 Hz, 1H), 5.09 (d. J=5.3 Hz, 1H), 5.15 (d. J=5.0 Hz, 1H), 5.20 (d, J=5.9 Hz, 1H), 5.37 (d, J=9.2 Hz, 1H), 6.74 (dd, J=11.2, 7.9 Hz, 1H), 6.83 (d, J=8.5 Hz, 2H), 7.07 (td, J=8.0, 5.2 Hz, 1H), 7.17 (d, J=8.7 Hz, 2H), 7.19 (s, 1H), 7.35 (d, J=8.4 Hz, 1H).

Example 10

4-Fluoro-3-(4-(methylthio)phenylmethyl)-1-(β-D-gluco-pyranosyl)indole

4-Fluoro-1-(2,3,4,6-tetra-O-acetyl-β-D-glucopyranosyl) indole obtained in Example 2-(3) and 4-(methylthio)benzoyl chloride were treated in a manner similar to Example 3 to give the titled compound as a colorless powder. APCI-Mass m/Z 451 (M+NH$_4$) $^1$H-NMR (DMSO-d6) δ 2.42 (s, 3H), 3.23-3.31 (m, 1H), 3.37-3.48 (m, 3H), 3.62-3.70 (m, 2H), 4.04 (s, 2H), 4.54 (t, J=5.7 Hz, 1H), 5.10 (d, J=5.3 Hz, 1H), 5.17 (d, J=5.0 Hz, 1H), 5.21 (d, J=5.7 Hz, 1H), 5.37 (d, J=9.2 Hz, 1H), 6.74 (dd, J=11.3, 8.0 Hz, 1H), 7.07 (td, J=8.0, 5.2 Hz, 1H), 7.15-7.22 (m, 4H), 7.24 (s, 1H), 7.36 (d, J=8.2 Hz, 1H).

Example 11

4-Chloro-3-(4-methylphenylmethyl)-1-(β-D-glucopyranosyl)-indole

4-Chloro-1-(2,3,4,6-tetra-O-acetyl-β-D-glucopyranosyl) indole obtained in Example 1-(3) and 4-methylbenzoyl chloride were treated in a manner similar to Example 2-(4), (5), (6) and (7) to give the titled compound as a colorless powder. APCI-Mass m/Z 418/420 (M+H). $^1$H-NMR (DMSO-d6) δ 2.25 (s, 3H), 3.21-3.25 (m, 1H), 3.32-3.39 (m, 1H), 3.43-3.47 (m, 2H), 3.61-3.69 (m, 2H), 4.22 (s, 2H), 4.53 (t, J=5.5 Hz, 1H), 5.01 (d, J=5.3 Hz, 1H), 5.15 (d, J=5.0 Hz, 1H), 5.20 (d, J=5.8 Hz, 1H), 5.39 (d, J=9.2 Hz, 1H), 7.06-7.12 (m, 5H), 7.21 (s, 1H), 7.53 (d, J=8.2 Hz, 1H).

Example 12

4-Fluoro-3-(4-(2-fluoroethyloxy)phenylmethyl)-1-(β-D-gluco-pyranosyl)indole

4-Fluoro-1-(2,3,4,6-tetra-O-acetyl-β-D-glucopyranosyl) indole obtained in Example 2-(3) and 4-(2-fluoroethyloxy) benzoyl chloride were treated in a manner similar to Example 2-(4), (5), (6) and (7) to give the titled compound as a colorless powder. APCI-Mass m/Z 467 (M+NH$_4$). $^1$H-NMR (DMSO-d6) δ 3.15-3.41 (m, 4H), 3.65 (m, 2H), 4.01 (s, 2H), 4.12 (m, 1H), 4.22 (dd, J=4.7, 3.2 Hz, 1H), 4.53 (t, J=5.5 Hz, 1H), 4.63 (m, 1H), 4.78 (m, 1H), 5.09 (d, J=5.3 Hz, 1H), 5.16 (d, J=5.0 Hz, 1H), 5.21 (d, J=5.9 Hz, 1H), 5.36 (d, J=9.1 Hz, 1H), 6.74 (dd, J=11.4, 7.8 Hz, 1H), 6.87 (d, J=8.6 Hz, 2H), 7.06 (dt, J=8.1, 5.2 Hz, 1H), 7.18 (d, J=8.6 Hz, 2H), 7.20 (s, 1H), 7.35 (d, J=8.4 Hz, 1H).

Example 13

3-(4-(2-Chloroethyloxy)phenylmethyl)-4-fluoro-1-(β-D-gluco-pyranosyl)indole

4-Fluoro-1-(2,3,4,6-tetra-O-acetyl-β-D-glucopyranosyl) indole obtained in Example 2-(3) and 4-(2-chloroethyloxy) benzoyl chloride were treated in a manner similar to Example 3 to give the titled compound as a colorless powder. APCI-Mass m/Z 483/485 (M+NH$_4$). $^1$H-NMR (DMSO-d6) δ 3.20-3.50 (m, 4H), 3.63-3.70 (m, 2H), 3.91 (t, J=5.1 Hz, 2H), 4.02 (s, 2H), 4.20 (t, J=5.0 Hz, 2H), 4.53 (t, J=5.5 Hz, 1H), 5.09 (d, J=5.3 Hz, 1H), 5.16 (d, J=5.0 Hz, 1H), 5.20 (d, J=5.8 Hz, 1H), 5.37 (d, J=9.2 Hz, 1H), 6.74 (dd, J=11.2, 7.9 Hz, 1H), 6.86 (d, J=8.7 Hz, 2H), 7.07 (m, 1H), 7.18 (d, J=8.5 Hz, 2H), 7.21 (s, 1H), 7.36 (d, J=8.3 Hz, 1H).

Example 14

3-(4-Bromophenylmethyl)-4-chloro-1-(β-D-glucopyranosyl)-indole (1) 4-Chloro-1-(2,3,4,6-tetra-O-acetyl-β-D-glucopyranosyl)-indole obtained in Example 1-(3) and 4-bromobenzoyl chloride were treated in a manner similar to Example 2-(4) to give 4-bromophenyl 4-chloro-1-(2,3,4,6-tetra-O-acetyl-β-D-glucopyranosyl)-indol-3-yl ketone as a colorless powder. APCI-Mass m/Z 664/666 (M+H). $^1$H-NMR (DMSO-d6) δ 1.69 (s, 3H), 1.97 (s, 3H), 1.98 (s, 3H), 2.04 (s, 3H), 4.11 (d, J=4.2 Hz, 2H), 4.30 (ddd, J=10.0, 4.3 and 4.2 Hz, 1H), 5.28 (t, J=9.8 Hz, 1H), 5.58 (t, J=9.6 Hz, 1H), 5.93 (t, J=9.4 Hz, 1H), 6.33 (d, J=9.0 Hz, 1H), 7.29 (d, J=7.5 Hz, 1H), 7.38 (t, J=8.0 Hz, 1H), 7.73-7.77 (m, 4H), 7.80 (d, J=8.2 Hz, 1H), 8.17 (s, 1H).

(2) The above 4-bromophenyl 4-chloro-1-(2,3,4,6-tetra-O-acetyl-β-D-glucopyranosyl)indol-3-yl ketone was treated in a manner similar to Example 2-(5) to give crude 4-bromophenyl 4-chloro-1-(2,3,4,6-tetra-O-acetyl-β-D-glucopyranosyl)-indol-3-yl methanol, which was used in the subsequent step without further purification.

(3) The above compound was treated in a manner similar to Example 3-(3) to give 3-(4-bromophenylmethyl)-4-chloro-1-(2,3,4,6-tetra-O-acetyl-β-D-glucopyranosyl)indole as colorless crystals. mp 223-225° C. APCI-Mass m/Z 667/669 (M+NH$_4$). $^1$H-NMR (DMSO-d6) δ 1.65 (s, 3H), 1.96 (s, 3H), 1.99 (s, 3H), 2.04 (s, 3H), 4.10 (A part of ABX, J=12.4, 2.7 Hz, 1H), 4.14 (B part of ABX, J=12.6, 5.2 Hz, 1H), 4.18 and 4.24 (ABq, J=16.3 Hz, 2H), 4.28 (ddd, J=10.1, 5.3 and 2.7 Hz, 1H), 5.24 (t, J=9.6 Hz, 1H), 5.51 (t, J=9.4 Hz, 1H), 5.55 (t, J=9.2 Hz, 1H), 6.18 (d, J=8.7 Hz, 1H), 7.06 (d, J=7.5 Hz, 1H), 7.10 (d, J=8.3 Hz, 2H), 7.17 (t, J=7.9 Hz, 1H), 7.33 (s, 1H), 7.44 (d, J=8.3 Hz, 2H), 7.65 (d, J=8.3 Hz, 1H).

(4) The above 3-(4-bromophenylmethyl)-4-chloro-1-(2,3,4,6-tetra-O-acetyl-β-D-glucopyranosyl)indole was treated in a manner similar to Example 2-(7) to give the titled compound, 3-(4-bromophenylmethyl)-4-chloro-1-(β-D-glucopyranosyl)-indole as a colorless powder. APCI-Mass m/Z 482/484 (M–H). $^1$H-NMR (DMSO-d6) δ 3.22-3.26 (m, 1H, 3.37-3.48 (m, 3H), 3.64-3.69 (m, 2H), 4.24 (s, 2H), 4.54 (t, J=5.4 Hz, 1H), 5.10 (d, J=5.0 Hz, 1H), 5.17 (d, J=5.3 Hz, 1H), 5.22 (d, J=5.8 Hz, 1H), 5.40 (d, J=9.0 Hz, 1H), 7.02 (d, J=7.5 Hz, 1H), 7.10 (t, J=7.9 Hz, 1H), 7.17 (d, J=8.3 Hz, 2H), 7.33 (s, 1H), 1.45 (d, J=8.3 Hz, 2H), 7.55 (d, J=8.2 Hz, 1H).

Example 15

3-(Benzo[b]furan-5-yl-methyl)-4-chloro-1-(β-D-glucopyranosyl)indole (1) 4-Chloro-1-(2,3,4,6-tetra-O-acetyl-β-D-glucopyranosyl)-indole obtained in Example 1-(3) and benzo[b]furan-5-carbonyl chloride were treated in a manner similar to Example 2-(4) to give benzo[b]furan-5-yl 4-chloro-1-(2,3,4, 6-tetra-O-acetyl-β-D-glucopyranosyl)indol-3-yl ketone as a colorless powder. APCI-Mass m/Z 626/628 (M+H). $^1$H-NMR (DMSO-d6) δ 1.74 (s, 3H), 1.97 (s, 3H), 1.98 (s, 3H), 2.03 (s, 3H), 4.10-4.11 (m, 2H), 4.30 (dt, J=9.9, 4.2 Hz, 1H), 5.27 (t, J=9.9 Hz, 1H), 5.54 (t, J=9.6 Hz, 1H), 5.74 (t, J=9.3 Hz, 1H), 6.34 (d, J=9.0 Hz, 1H), 7.06 (d, J=1.3 Hz, 1H), 7.28 (d, J=7.5 Hz, 1H), 7.37 (t, J=8.0 Hz, 1H), 7.75 (d, J=8.7

Hz, 1H), 7.81 (d, J=8.3 Hz, 1H), 7.85 (dd, J=8.6, 1.7 Hz, 1H), 8.12 (d, J=1.4 Hz, 1H), 8.13 (s, 2H).

(2) The above benzo[b]furan-5-yl 4-chloro-1-(2,3,4,6-tetra-O-acetyl-β-D-glucopyranosyl)indol-3-yl ketone was treated in a manner similar to Example 2-(5) to give crude benzo[b]furan-5-yl 4-chloro-1-(2,3,4,6-tetra-O-acetyl-β-D-glucopyranosyl)indol-3-yl methanol, which was used in the subsequent step without further purification.

(3) The above compound was treated in a manner similar to Example 3-(3) to give 3-(benzo[b]furan-5-yl-methyl)-4-chloro-1-(2,3,4,6-tetra-O-acetyl-β-D-glucopyranosyl)indole as colorless crystals. mp 186-188° C. APCI-Mass m/Z 629/631 (M+NH$_4$). $^1$H-NMR (DMSO-d6) δ 1.66 (s, 3H), 1.96 (s, 3H), 1.98 (s, 3H), 2.03 (s, 3H), 4.09 (A part of ABX, J=12.4, 2.8 Hz, 1H), 4.13 (B part of ABX, J=12.4, 5.5 Hz, 1H), 4.28 (ddd, J=9.9, 5.0 and 3.0 Hz, 1H), 4.31 and 4.35 (ABq, J=14.2 Hz, 2H), 5.23 (t, J=9.7 Hz, 1H), 5.50 (t, J=9.4 Hz, 1H), 5.55 (t, J=9.2 Hz, 1H), 6.17 (d, J=8.7 Hz, 1H), 6.84 (d, J=1.4 Hz, 1H), 7.06 (d, J=7.5 Hz, 1H), 7.14-7.19 (m, 2H), 7.28 (s, 1H), 7.36 (s, 1H), 7.47 (d, J=8.3 Hz, 1H), 7.65 (d, J=8.2 Hz, 1H), 7.92 (d, J=2.1 Hz, 1H).

(4) The above 3-(benzo[b]furan-5-yl-methyl)-4-chloro-1-(2,3,4,6-tetra-O-acetyl-β-D-glucopyranosyl)indole was treated in a manner similar to Example 2-(7) to give the titled compound, 3-(benzo[b]furan-5-yl-methyl)-4-chloro-1-(β-D-glucopyranosyl)indole as a colorless powder. APCI-Mass m/Z 444/446 (M+H). $^1$H-NMR (DMSO-d6) δ 3.23 (td, J=9.1, 5.6 Hz, 1H), 3.39 (td, J=8.9, 5.5 Hz, 1H), 3.43-3.48 (m, 2H), 3.63-3.69 (m, 2H), 4.36 (s, 2H), 4.53 (t, J=5.5 Hz, 1H), 5.09 (d, J=5.3 Hz, 1H), 5.15 (d, J=5.0 Hz, 1H), 5.22 (d, J=5.8 Hz, 1H), 5.40 (d, J=9.2 Hz, 1H), 6.87 (d, J=1.3 Hz, 1H), 7.02 (d, J=7.5 Hz, 1H), 7.10 (t, J=7.9 Hz, 1H), 7.21 (dd, J=8.4, 1.5 Hz, 1H), 7.26 (s, 1H), 7.44 (s, 1H), 7.48 (d, J=8.3 Hz, 1H), 7.55 (d, J=8.2 Hz, 1H), 7.92 (d, J=2.1 Hz, 1H).

Example 16

4-Chloro-3-(5-ethylthiophen-2-yl-methyl)-1-(β-D-gluco-pyranosyl)indole

4-Chloro-1-(2,3,4,6-tetra-O-acetyl-β-D-glucopyranosyl)indole obtained in Example 1-(3) and 5-ethylthiophen-2-carbonyl chloride were treated in a manner similar to Example 2-(4), (5), (6) and (7) to give the titled compound as a pink powder. APCI-Mass m/Z 455/457 (M+NH$_4$). $^1$H-NMR (DMSO-d6) δ 1.17 (t, J=7.4 Hz, 3H), 2.71 (q, J=7.4 Hz, 2H), 3.15-3.43 (m, 4H), 3.67 (m, 2H), 4.36 (s, 2H), 4.54 (t, J=5.5 Hz, 1H), 5.10 (d, J=5.3 Hz, 1H), 5.16 (d, J=5.0 Hz, 1H), 5.20 (d, J=5.9 Hz, 1H), 5.40 (d, J=9.1 Hz, 1H), 6.62 (m, 2H), 7.04 (m, 1H), 7.11 (t, J=7.9 Hz, 1H), 7.38 (s, 1H), 7.54 (d, J=8.2 Hz, 1H).

Example 17

4-Chloro-3-(4-(2-Fluoroethyloxy)phenylmethyl)-1-(β-D-glucopyranosyl)indole

4-Chloro-1-(2,3,4,6-tetra-O-acetyl-β-D-glucopyranosyl)indole obtained in Example 1-(3) and 4-(2-fluoroethyloxy)benzoyl chloride were treated in a manner similar to Example 3 to give the titled compound as a colorless powder. APCI-Mass m/Z 466/468 (M+H). $^1$H-NMR (DMSO-d6) δ 3.24 (td, J=8.8, 5.7 Hz, 1H), 3.38-3.47 (m, 3H), 3.62-3.69 (m, 2H), 4.14-4.16 (m, 1H), 4.20 (s, 2H), 4.20-4.22 (m, 1H), 4.53 (t, J=5.5 Hz, 1H), 4.66-4.67 (m, 1H), 4.76-4.77 (m, 1H), 5.09 (d, J=5.31 Hz, 1H), 5.15 (d, J=5.0 Hz, 1H), 5.21 (d, J=5.8 Hz, 1H), 5.39 (d, J=9.0 Hz, 1H), 6.87 (d, J=8.7 Hz, 2H), 7.02 (d, J=7.5 Hz, 1H), 7.09 (t, J=7.9 Hz, 1H), 7.15 (d, J=8.5 Hz, 2H), 7.22 (s, 1H), 7.53 (d, J=8.2 Hz, 1H).

Example 18

3-(5-Ethylthiophen-2-yl-methyl)-4-fluoro-1-(β-D-gluco-pyranosyl)indole

4-Fluoro-1-(2,3,4,6-tetra-O-acetyl-β-D-glucopyranosyl)indole obtained in Example 2-(3) and 5-ethylthiophen-2-carbonyl chloride were treated in a manner similar to Example 2-(4), (5), (6) and (7) to give the titled compound as a colorless powder. APCI-Mass m/Z 439 (M+NH$_4$). $^1$H-NMR (DMSO-d6) δ 1.17 (t, J=7.5 Hz, 3H), 2.69 (q, J=7.5 Hz, 2H), 3.20-3.48 (m, 4H), 3.67 (m, 2H), 4.20 (s, 2H), 4.53 (br, 1H), 5.08 (br, 1H), 5.20 (br, 2H), 5.38 (d, J=9.2 Hz, 1H), 6.60 (d, J=3.3 Hz, 1H), 6.65 (d, J=3.2 Hz, 1H), 6.77 (dd, J=11.1, 7.8 Hz, 1H), 7.09 (m, 1H), 7.31 (s, 1H), 7.39 (d, J=8.3 Hz, 1H).

Example 19

4-Chloro-3-(4-(2-chloroethyloxy)phenylmethyl)-1-(β-D-gluco-pyranosyl)indole

4-Chloro-1-(2,3,4,6-tetra-O-acetyl-β-D-glucopyranosyl)indole obtained in Example 1-(3) and 4-(2-chloroethyloxy)benzoyl chloride were treated in a manner similar to Example 3 to give the titled compound as a colorless powder. APCI-Mass m/Z 499/501 (M+NH$_4$). $^1$H-NMR (DMSO-d6) δ 3.24 (td, J=9.2, 4.1 Hz, 1H), 3.39 (td, J=8.7, 5.2 Hz, 1H), 3.43-3.47 (m, 2H), 3.62-3.69 (m, 2H), 3.91-3.93 (m, 2H), 4.19-4.21 (m, 4H), 4.53 (t, J=4.9 Hz, 1H), 5.09 (d, J=4.8 Hz, 1H), 5.15 (d, J=4.7 Hz, 1H), 5.21 (d, J=5.3 Hz, 1H), 5.39 (d, J=9.2 Hz, 1H), 6.87 (d, J=8.5 Hz, 2H), 7.02 (d, J=7.5 Hz, 1H), 7.09 (t, J=7.9 Hz, 1H), 7.15 (d, J=8.7 Hz, 2H), 7.22 (s, 1H), 7.53 (d, J=8.2 Hz, 1H).

Example 20

3-(Benzo[b]furan-5-yl-methyl)-4-fluoro-1-(β-D-glucopyranosyl) indole (1) 4-Fluoro-1-(2,3,4,6-tetra-O-acetyl-β-D-glucopyranosyl)-indole obtained in Example 2-(3) and benzo[b]furan-5-carbonyl chloride were treated in a manner similar to Example 2-(4) to give benzo[b]furan-5-yl 4-fluoro-1-(2,3,4,6-tetra-O-acetyl-β-D-glucopyranosyl)indol-3-yl ketone as a colorless powder. APCI-Mass m/Z 627 (M+NH$_4$), 610 (M+H). $^1$H-NMR (DMSO-d6) δ 1.73 (s, 3H), 1.96 (s, 3H), 1.98 (s, 3H), 2.03 (s, 3H), 4.10 (d, J=4.0 Hz, 2H), 4.28-4.31 (m, 1H), 5.28 (t, J=9.8 Hz, 1H), 5.54 (t, J=9.6 Hz, 1H), 5.77 (t, J=9.3 Hz, 1H), 6.35 (d, J=9.2 Hz, 1H), 7.04 (dd, J=10.8, 8.0 Hz, 1H), 7.09 (d, J=1.4 Hz, 1H), 7.39 (td, J=8.1, 4.7 Hz, 1H), 7.64 (d, J=8.3 Hz, 1H), 7.75-7.77 (m, 1H), 7.82-7.84 (m, 1H), 8.14-8.15 (m, 2H), 8.17 (s, 1H).

(2) The above benzo[b]furan-5-yl 4-fluoro-1-(2,3,4,6-tetra-O-acetyl-β-D-glucopyranosyl)indol-3-yl ketone was treated in a manner similar to Example 2-(5) to give crude benzo[b]furan-5-yl 4-fluoro-1-(2,3,4,6-tetra-O-acetyl-β-D-glucopyranosyl)-indol-3-yl methanol, which was used in the subsequent step without further purification.

(3) The above compound was treated in a manner similar to Example 3-(3) to give 3-(benzo[b]furan-5-yl-methyl)-4-fluoro-1-(2,3,4,6-tetra-O-acetyl-β-D-glucopyranosyl)indole as colorless needles. mp 184-185° C. APCI-Mass m/Z 613 (M+NH$_4$). $^1$H-NMR (DMSO-d6) δ 1.63 (s, 3H), 1.96 (s, 3H), 1.99 (s, 3H), 2.04 (s, 3H), 4.09 (A part of ABX, J=12.4, 2.7

Hz, 1H), 4.13 (m, 1H), 4.16 (s, 2H), 4.29 (ddd, J=9.8, 5.3 and 2.9 Hz, 1H), 5.22 (t, J=9.6 Hz, 1H), 5.51 (t, J=9.3 Hz, 1H), 5.55 (t, J=9.2 Hz, 1H), 6.16 (d, J=8.7 Hz, 1H), 6.77 (dd, J=11.1, 7.9 Hz, 1H), 6.85 (d, J=1.3 Hz, 1H), 7.12-7.17 (m, 2H), 7.26 (s, 1H), 7.42 (s, 1H), 7.47 (d, J=8.3 Hz, 2H), 7.92 (d, J=2.1 Hz, 1H).

(4) The above 3-(benzo[b]furan-5-yl-methyl)-4-fluoro-1-(2,3,4,6-tetra-O-acetyl-β-D-glucopyranosyl)indole was treated in a manner similar to Example 2-(7) to give the titled compound, 3-(benzo[b]furan-5-yl-methyl)-4-fluoro-1-(β-D-glucopyranosyl)indole as a colorless powder. APCI-Mass m/Z 445 (M+NH$_4$). $^1$H-NMR (DMSO-d6) δ 3.24 (td, J=8.8, 5.2 Hz, 1H), 3.39 (m, 1H), 3.43-3.47 (m, 2H), 3.65-3.69 (m, 2H), 4.18 (s, 2H), 4.53 (t, J=5.2 Hz, 1H), 5.09 (d, J=5.1 Hz, 1H), 5.15 (d, J=4.8 Hz, 1H), 5.21 (d, J=5.3 Hz, 1H), 5.37 (d, J=9.2 Hz, 1H), 6.74 (dd, J=11.1, 7.7 Hz, 1H), 6.88 (d, J=1.4 Hz, 1H), 7.07 (td, J=8.0, 5.0 Hz, 1H), 7.23 (dd, J=8.6, 1.4 Hz, 1H), 7.25 (s, 1H), 7.36 (d, J=8.3 Hz, 1H), 7.48 (d, J=8.3 Hz, 1H), 7.50 (s, 1H), 7.92 (d, J=2.1 Hz, 1H).

Example 21

4-Chloro-3-(2,3-dihydrobenzo[b]furan-5-yl-methyl)-1-(β-D-glucopyranosyl)indole (1) 4-Chloro-1-(2,3,4,6-tetra-O-acetyl-β-D-glucopyranosyl)-indole (300 mg) obtained in Example 1-(3) and 2,3-dihydro-benzo[b]furan-5-carbonyl chloride (171 mg) were dissolved in dichloromethane (9 ml), and thereto was added aluminum chloride (166 mg) at 0° C. After being stirred at same temperature for 2.5 hours, the mixture was poured into ice-water (50 ml), and extracted with chloroform (30 ml) twice. The combined organic layer was washed with a saturated aqueous sodium hydrogen carbonate solution (10 ml) and dried over magnesium sulfate. The insoluble materials were filtered off, and the filtrate was evaporated under reduced pressure to give crude 4-chloro-1-(2,3,4,6-tetra-O-acetyl-β-D-glucopyranosyl)indol-3-yl 2,3-dihydrobenzo[b]furan-5-yl ketone (477 mg), which was partially deacetylated. This crude compound was dissolved in chloroform (9 ml), and thereto were added successively pyridine (0.151 ml), acetic anhydride (0.177 ml) and 4-(dimethyl-amino)pyridine (7.6 mg). After being stirred at room temperature for 16 hours, the solvent was evaporated under reduced pressure. The residue was dissolved in ethyl acetate (100 ml), and the mixture was washed with a 10% aqueous copper (II) sulfate solution (10 ml) twice and a saturated aqueous sodium hydrogen carbonate solution (10 ml), and dried over magnesium sulfate. The insoluble materials were filtered off, and the filtrate was evaporated under reduced pressure. The residue was purified by silica gel column chromatography (hexane: ethyl acetate=90:10-60:40) to give 4-chloro-1-(2,3,4,6-tetra-O-acetyl-β-D-glucopyranosyl)-indol-3-yl 2,3-dihydrobenzo[b]furan-5-yl ketone (346 mg) as a colorless powder. APCI-Mass m/Z 628/630 (M+H). $^1$H-NMR (DMSO-d6) δ 1.71 (s, 3H), 1.97 (s, 3H), 1.98 (s, 3H), 2.04 (s, 3H), 3.25 (td, J=8.8, 2.2 Hz, 2H), 4.08-4.14 (m, 2H), 4.30 (ddd, J=9.9, 5.3 and 3.0 Hz, 1H), 4.66 (t, J=8.8 Hz, 2H), 5.28 (t, J=9.8 Hz, 1H), 5.54 (t, J=9.6 Hz, 1H), 5.72 (t, J=9.4 Hz, 1H), 6.32 (d, J=9.0 Hz, 1H), 6.87 (d, J=8.3 Hz, 1H), 7.25 (d, J=7.7 Hz, 1H), 7.35 (t, J=8.0 Hz, 1H), 7.64 (dd, J=8.3, 1.6 Hz, 1H), 7.72 (br, 1H), 7.78 (d, J=8.3 Hz, 1H), 8.03 (s, 1H).

(2) The above 4-chloro-1-(2,3,4,6-tetra-O-acetyl-β-D-gluco-pyranosyl)-indol-3-yl 2,3-dihydrobenzo[b]furan-5-yl ketone was treated in a manner similar to Example 2-(5), (6) and (7) to give the titled compound, 4-chloro-3-(2,3-dihydrobenzo[b]furan-5-yl-methyl)-1-(β-D-glucopyranosyl)indole as a colorless powder. APCI-Mass m/Z 463/465 (M+NH$_4$). $^1$H-NMR (DMSO-d6) δ 3.11 (t, J=8.6 Hz, 2H), 3.22-3.26 (m, 1H), 3.36-3.41 (m, 1H), 3.43-3.47 (m, 2H), 3.63-3.68 (m, 2H), 4.18 (s, 2H), 4.47 (t, J=8.8 Hz, 2H), 4.53 (t, J=5.4 Hz, 1H), 5.09 (d, J=5.3 Hz, 1H), 5.16 (d, J=4.8 Hz, 1H), 5.21 (d, J=5.5 Hz, 1H), 5.39 (d, J=9.2 Hz, 1H), 6.65 (d, J=8.0 Hz, 1H), 6.94 (d, J=8.2 Hz, 1H), 7.03 (d, J=7.5 Hz, 1H), 7.08-7.11 (m, 2H), 7.22 (s, 1H), 7.53 (d, J=8.0 Hz, 1H).

Example 22

4-Bromo-3-(4-ethylphenylmethyl)-1-(β-D-glucopyranosyl)indole (1) 4-Bromo-1-(2,3,4,6-tetra-O-acetyl-β-D-glucopyranosyl)-indole was prepared from 4-bromoindoline in a manner similar to Example 2-(1), (2) and (3) as colorless needles. mp 166-167° C. APCI-Mass m/Z 543/545 (M+NH$_4$), 526/528 (M+H). $^1$H-NMR (DMSO-d6) δ 1.65 (s, 3H), 1.97 (s, 3H), 1.99 (s, 3H), 2.04 (s, 3H), 2.45 (s, 3H), 4.09 (A part of ABX, J=12.4, 2.5 Hz, 1H), 4.13 (B part of ABX, J=12.4, 5.4 Hz, 1H), 4.30 (ddd, J=10.0, 5.3 and 2.5 Hz, 1H), 5.26 (t, J=9.7 Hz, 1H), 5.53 (t, J=9.5 Hz, 1H), 5.62 (t, J=9.3 Hz, 1H), 6.22 (d, J=9.2 Hz, 1H), 6.48 (d, J=3.4 Hz, 1H), 7.16 (t, J=8.0 Hz, 1H), 7.32 (d, J=7.5 Hz, 1H), 7.62 (d, J=3.4 Hz, 1H), 7.71 (d, J=8.3 Hz, 1H).

(2) The above 4-bromo-1-(2,3,4,6-tetra-O-acetyl-β-D-gluco-pyranosyl)indole and 4-ethylbenzoyl chloride were treated in a manner similar to Example 3 to give the titled compound, 4-bromo-3-(4-ethylphenylmethyl)-1-(β-D-glucopyranosyl)indole as a colorless powder. APCI-Mass m/Z 476/478 (M+H). $^1$H-NMR (DMSO-d6) δ 1.15 (t, J=7.6 Hz, 3H), 2.56 (q, J=7.5 Hz, 2H), 3.23 (td, J=9.0, 5.5 Hz, 1H), 3.39 (td, J=8.8, 5.1 Hz, 1H), 3.43-3.47 (m, 2H), 3.61-3.69 (m, 2H), 4.26 (s, 2H), 4.53 (t, J=5.3 Hz, 1H), 5.09 (d, J=5.3 Hz, 1H), 5.16 (d, J=5.1 Hz, 1H), 5.20 (d, J=5.8 Hz, 1H), 5.40 (d, J=9.0 Hz, 1H), 7.03 (t, J=7.9 Hz, 1H), 7.09-7.14 (m, 4H), 7.21 (d, J=7.5 Hz, 1H), 7.23 (s, 1H), 7.59 (d, J=8.3 Hz, 1H).

Example 23

3-(4-Ethylphenylmethyl)-4-methyl-1-(β-D-glucopyranosyl)-indole (1) 4-Methyl-1-(2,3,4,6-tetra-O-acetyl-β-D-glucopyranosyl)-indole was prepared from 4-methylindoline in a manner similar to Example 2-(1), (2) and (3) as colorless needles. mp 156-157° C. APCI-Mass m/Z 479 (M+NH$_4$). $^1$H-NMR (DMSO-d6) δ 1.64 (s, 3H), 1.97 (s, 3H), 1.98 (s, 3H), 2.04 (s, 3H), 2.45 (s, 3H), 4.07 (A part of ABX, J=12.4, 2.4 Hz, 1H), 4.12 (B part of ABX, J=12.4, 5.4 Hz, 1H), 4.30 (ddd, J=10.0, 5.4 and 2.4 Hz, 1H), 5.21 (t, J=9.7 Hz, 1H), 5.54 (t, J=9.5 Hz, 1H), 5.61 (t, J=9.3 Hz, 1H), 6.19 (d, J=9.0 Hz, 1H), 6.53 (d, J=3.4 Hz, 1H), 6.88 (d, J=7.2 Hz, 1H), 7.09 (t, J=7.7 Hz, 1H), 7.43 (d, J=3.4 Hz, 1H), 7.45 (d, J=8.3 Hz, 1H).

(2) The above 4-methyl-1-(2,3,4,6-tetra-O-acetyl-β-D-gluco-pyranosyl)indole and 4-ethylbenzoyl chloride were treated in a manner similar to Example 3 to give the titled compound, 3-(4-ethylphenylmethyl)-4-methyl-1-(β-D-glucopyranosyl)-indole as a colorless powder. APCI-Mass m/Z 412 (M+H). $^1$H-NMR (DMSO-d6) δ 1.15 (t, J=−1.6 Hz, 3H), 2.41 (s, 3H), 2.56 (q, J=7.5 Hz, 2H), 3.23 (td, J=8.9, 5.2 Hz, 1H), 3.37-3.47 (m, 3H), 3.64-3.69 (m, 2H), 4.16 (s, 2H), 4.51 (t, J=5.3 Hz, 1H), 5.06 (d, J=5.1 Hz, 1H), 5.13-5.15 (m, 2H), 5.34 (d, J=9.0 Hz, 1H), 6.70 (d, J=7.1 Hz, 1H), 6.97 (t, J=7.7 Hz, 1H), 7.07-7.12 (m, 5H), 7.34 (d, J=8.3 Hz, 1H).

Example 24

4-Fluoro-3-(4-methylphenylmethyl)-1-(β-D-glucopyranosyl)-indole

4-Fluoro-1-(2,3,4,6-tetra-O-acetyl-β-D-glucopyranosyl) indole obtained in Example 2-(3) and 4-methylbenzoyl chloride were treated in a manner similar to Example 2-(4), (5), (6) and (7) to give the titled compound as a colorless powder. APCI-Mass m/Z 419 (M+NH$_4$). $^1$H-NMR (DMSO-d6) δ 2.24 (3, 3H), 3.21-3.25 (m, 2H), 3.37-3.46 (m, 2H), 3.63-3.67 (m, 2H), 4.04 (s, 2H), 4.53 (t, J=5.5 Hz, 1H), 5.09 (d, J=5.1 Hz, 1H), 5.16 (d, J=5.0 Hz, 1H), 5.21 (d, J=5.1 Hz, 1H), 5.37 (d, J=9.0 Hz, 1H), 6.74 (dd, J=11.1, 7.9 Hz, 1H), 7.05-7.07 (m, 3H), 7.13-7.15 (m, 2H), 7.20 (s, 1H), 7.35 (d, J=8.3 Hz, 1H).

Example 25

3-(4-(Difluoromethyl)phenylmethyl)-4-fluoro-1-(β-D-gluco-pyranosyl)indole (1) 4-Fluoro-1-(2,3,4,6-tetra-O-acetyl-β-D-glucopyranosyl)-indole (3.50 g) obtained in Example 2-(3) and N,N-dimethyl-formamide (3.49 ml) were dissolved in 1,2-dichloroethane (70 ml), and thereto was added dropwise phosphorus(III) oxychloride (2.10 ml). The mixture was stirred at 70° C. for 1 hour, and thereto was added water (100 ml) at 0° C. The resultant mixture was extracted with ethyl acetate (200 ml) twice, and the combined organic layer was washed with brine (40 ml) and dried over magnesium sulfate. The insoluble materials were filtered off, and the filtrate was evaporated under reduced pressure. The residue was purified by silica gel column chromatography (hexane:ethyl acetate=90:10-50:50) followed by recrystallization from ethyl alcohol (20 ml) to give 4-fluoro-1-(2,3,4,6-tetra-O-acetyl-β-D-glucopyranosyl)indole-3-carboxaldehyde (2.93 g) as colorless crystals. mp 190-192° C. APCI-Mass m/Z 511 (M+NH$_4$) $^1$H-NMR (DMSO-d6) δ 1.64 (s, 3H), 1.98 (s, 3H), 2.00 (s, 3H), 2.05 (s, 3H), 4.12 (A part of ABX, J=12.4, 2.5 Hz, 1H), 4.17 (B part of ABX, J=12.4, 5.5 Hz, 1H), 4.33 (ddd, J=10.0, 5.5 and 2.5 Hz, 1H), 5.32 (t, J=9.8 Hz, 1H), 5.56 (t, J=9.6 Hz, 1H), 5.66 (t, J=9.3 Hz, 1H), 6.36 (d, J=9.0 Hz, 1H), 7.11 (dd, J=10.6, 8.0 Hz, 1H), 7.38 (td, J=8.1, 5.1 Hz, 1H), 7.65 (d, J=8.3 Hz, 1H), 8.53 (s, 1H), 10.0 (d, J=2.9 Hz, 1H).

(2) To a mixture of magnesium turnings (71 mg) in tetrahydrofuran (2 ml) was added dropwise a solution of 1-bromo-4-difluoromethylbenzene (587 mg) in tetrahydrofuran (1.5 ml) under being stirred vigorously. The mixture was warmed with a dryer, and thereto was added 1,2-dibromoethane (4 drops). The resultant mixture was vigorously stirred at room temperature till a disappearance of magnesium turnings, and then dropwise added to a solution of the above 4-fluoro-1-(2,3,4,6-tetra-O-acetyl-β-D-glucopyranosyl)indole-3-carboxaldehyde (350 mg) in tetrahydrofuran (4 ml) over 10 minutes at –78° C. under argon atmosphere. The mixture was stirred at same temperature for 1 hour, and thereto was added a saturated aqueous ammonium chloride solution (20 ml). The resultant mixture was extracted with ethyl acetate (50 ml) 3 times, and the combined organic layer was dried over magnesium sulfate. The insoluble materials were filtered off, and the filtrate was evaporated under reduced pressure to give crude 4-(difluoromethyl)phenyl 4-fluoro-1-(2,3,4,6-tetra-O-acetyl-β-D-glucopyranosyl)indol-3-yl methanol, which was used in the subsequent step without further purification.

(3) To a stirred suspension of the above compound and tri-ethylsilane (0.57 ml) in dichloromethane (4 ml)-acetonitrile (8 ml) was added boron trifluoride-diethyl ether complex (0.50 ml) at –10° C. under argon atmosphere. The mixture was stirred at same temperature for 30 minutes, and thereto was added a saturated aqueous sodium hydrogen carbonate solution (40 ml). The organic solvent was evaporated under reduced pressure, and the residue was extracted with ethyl acetate (40 ml) twice. The combined organic layer was dried over magnesium sulfate followed by being filtered through an aminosilane-treated silica gel pad, and the filtrate was evaporated under reduced pressure. The residue was purified by silica gel column chromatography (hexane:ethyl acetate=95:5-60:40) to give 3-(4-(difluoromethyl)-phenylmethyl)-4-fluoro-1-(2,3,4,6-tetra-O-acetyl-β-D-gluco-pyranosyl)indole (183 mg) as a pale yellow solid. APCI-Mass m/Z 623 (M+NH$_4$). $^1$H-NMR (DMSO-d6) δ 1.63 (s, 3H), 1.96 (s, 3H), 1.99 (s, 3H), 2.04 (s, 3H), 4.08-4.16 (m, 4H), 4.29 (ddd, J=10.0, 5.2 and 2.7 Hz, 1H), 5.23 (t, J=9.6 Hz, 1H), 5.50-5.57 (m, 2H), 6.16 (d, J=8.5 Hz, 1H), 6.78 (dd, J=11.0, 7.9 Hz, 1H), 6.97 (t, J=56.0 Hz, 1H), 7.15 (td, J=8.0, 5.3 Hz, 1H), 7.31-7.32 (m, 3H), 7.45-7.48 (m, 3H).

(4) The above 3-(4-(difluoromethyl)phenylmethyl)-4-fluoro-1-(2,3,4,6-tetra-O-acetyl-β-D-glucopyranosyl)indole was treated in a manner similar to Example 2-(7) to give the titled compound, 3-(4-(d-difluoromethyl)phenylmethyl)-4-fluoro-1-(β-D-glucopyranosyl)indole as a colorless powder. APCI-Mass m/Z 455 (M+NH$_4$). $^1$H-NMR (DMSO-d6) δ 3.20-3.28 (m, 1H), 3.36-3.49 (m, 3H), 3.64-3.71 (m, 2H), 4.15 (s, 2H), 4.54 (t, J=5.6 Hz, 1H), 5.11 (d, J=5.3 Hz, 1H), 5.19 (, J=4.9 Hz, 1H), 5.23 (d, J=5.9 Hz, 1H), 5.38 (d, J=9.0 Hz, 1H), 6.74 (dd, J=11.3, 7.8 Hz, 1H), 6.97 (t, J=56.0 Hz, 1H), 7.08 (td, J=8.1, 5.4 Hz, 1H), 7.31-7.48 (m, 6H).

Example 26

3-(4-(Difluoromethoxy)phenylmethyl)-4-fluoro-1-(β-D-gluco-pyranosyl)indole (1) A mixture solution of 4-fluoro-1-(2,3,4,6-tetra-O-acetyl-β-D-glucopyranosyl)indole-3-carboxaldehyde (350 mg) obtained in Example 25-(1), 4-(difluoromethoxy)benzeneboronic acid (399 mg), (acetylacetonato)dicarbonylrhodium(I) (37 mg) and 1,1'-bis-(diphenylphosphino)ferrocene (79 mg) in H$_2$O (3.6 ml)-1,2-dimethoxyethane (3.6 ml) was stirred at 80° C. under argon atmosphere for 18 hours. The reaction mixture was cooled to room temperature, and thereto was added water (10 ml). The mixture was extracted with ethyl acetate (20 ml) 3 times, and the combined organic layer was dried over magnesium sulfate followed by being filtered through an aminosilane-treated silica gel pad. The filtrate was evaporated under reduced pressure to give crude 4-(difluoromethoxy)phenyl 4-fluoro-1-(2,3,4,6-tetra-O-acetyl-β-D-glucopyranosyl)indol-3-yl methanol, which was used in the subsequent step without further purification.

(2) The above compound was treated in a manner similar to Example 25-(3) to give 3-(4-(difluoromethoxy)phenylmethyl)-4-fluoro-1-(2,3,4,6-tetra-O-acetyl-β-D-glucopyranosyl)indole (40 mg) as a colorless solid. APCI-Mass m/Z 639 (M+NH$_4$).

(3) The above 3-(4-(difluoromethoxy)phenylmethyl)-4-fluoro-1-(2,3,4,6-tetra-O-acetyl-β-D-glucopyranosyl)indole was treated in a manner similar to Example 2-(7) to give the titled compound, 3-(4-(difluoromethoxy)phenylmethyl)-4-fluoro-1-(β-D-glucopyranosyl)indole as a colorless powder. APCI-Mass m/Z 471 (M+NH$_4$). $^1$H-NMR (DMSO-d6) δ 3.24 (td, J=8.9, 5.5 Hz, 1H), 3.40 (td, J=8.8, 5.3 Hz, 1H), 3.43-3.47

(m, 2H), 3.65-3.69 (m, 2H), 4.08 (s, 2H), 4.53 (t, J=5.5 Hz, 1H), 5.09 (d, J=5.3 Hz, 1H), 5.17 (d, J=5 Hz, 1H), 5.21 (d, J=5.9 Hz, 1H), 5.38 (d, J=9.0 Hz, 1H), 6.75 (dd, J=11.2, 7.9 Hz, 1H), 7.06-7.10 (m, 3H), 7.15 (t, J=74.5 Hz, 1H) 7.28-7.30 (m, 3H), 7.37 (d, J=8.3 Hz, 1H).

Example 27

4-Chloro-3-(4-fluorophenylmethyl)-1-(β-D-glucopyranosyl)-indole (1) 4-Chloro-1-(2,3,4,6-tetra-O-acetyl-β-D-glucopyranosyl)-indole obtained in Example 1-(3) and 4-fluorobenzoyl chloride were treated in a manner similar to Example 2-(4) to give 4-chloro-1-(2,3,4,6-tetra-O-acetyl-β-D-glucopyranosyl)-indol-3-yl 4-fluorophenyl ketone as a colorless powder. APCI-Mass m/Z 604/606 (M+H). $^1$H-NMR (DMSO-d6) δ 1.69 (s, 3H), 1.79 (s, 3H), 1.98 (s, 3H), 2.04 (s, 3H), 4.11 (d, J=3.9 Hz, 2H), 4.27-4.33 (m, 1H), 5.29 (t, J=9.8 Hz, 1H), 5.54 (t, J=9.6 Hz, 1H), 5.72 (t, J=9.4 Hz, 1H), 6.33 (d, J=9.0 Hz, 1H), 7.28 (d, J=7.3 Hz, 1H), 7.35-7.42 (m, 3H), 7.80 (d, J=8.3 Hz, 1H), 7.89 (dd, J=8.4, 5.7 Hz, 2H), 8.16 (s, 1H).

(2) The above compound (520 mg) was treated in a manner similar to Example 2-(5) to give crude 4-chloro-1-(2,3,4,6-tetra-O-acetyl-β-D-glucopyranosyl)indol-3-yl 4-fluorophenyl methanol, which was used in the subsequent step without further purification.

(3) The above compound was dissolved in dichloromethane (10 ml)-acetonitrile (20 ml), and thereto were added successively triethylsilane (0.688 ml) and boron trifluoride-diethyl ether complex (0.546 ml) at −10° C. under argon atmosphere. After being stirred at same temperature for 30 minutes, thereto was added a saturated aqueous sodium hydrogen carbonate solution. The mixture was extracted with ethyl acetate, and the organic layer was washed with brine and dried over sodium sulfate. The insoluble materials were filtered off, and the filtrate was evaporated under reduced pressure. The residue was purified by silica gel column chromatography (hexane:ethyl acetate=2:1-3:2) to give 4-chloro-3-(4-fluorophenylmethyl)-1-(2,3,4,6-tetra-O-acetyl-β-D-glucopyranosyl)indole (454 mg) as colorless crystals. APCI-Mass m/Z 607/609 (M+NH$_4$). $^1$H-NMR (DMSO-d6) δ 1.65 (s, 3H), 1.96 (s, 3H), 1.99 (s, 3H), 2.04 (s, 3H), 4.07-4.32 (m, 5H), 5.23 (t, J=0.6 Hz, 1H), 5.51 (t, J=9.5 Hz, 1H), 5.55 (t, J=9.5 Hz, 1H), 6.17 (d, J=8.7 Hz, 1H), 7.05-7.10 (m, 3H), 7.15-7.20 (m, 3H), 7.29 (s, 1H), 7.64 (d, J=8.3 Hz, 1H).

(4) The above compound was treated in a manner similar to Example 2-(7) to give the titled compound, 4-chloro-3-(4-fluoro-phenylmethyl)-1-(β-D-glucopyranosyl)indole as a colorless powder. APCI-Mass m/Z 422/424 (M+H). $^1$H-NMR (DMSO-d6) δ 3.22-3.50 (m, 4H), 3.63-3.72 (m, 2H), 4.25 (s, 2H), 4.53 (t, J=5.3 Hz, 1H), 5.09 (d, J=5.3 Hz, 1H), 5.16 (d, J=−5.0 Hz, 1H), 5.21 (d, J=5.9 Hz, 1H), 5.40 (d, J=9.2 Hz, 1H), 7.02 (d, J=7.5 Hz, 1H), 7.05-7.14 (m, 3H), 7.24 (dd, J=8.1, 5.9 Hz, 2H), 7.29 (s, 1H), 7.54 (d, J=8.2 Hz, 1H).

Example 28

4,6-Dichloro-3-(4-ethoxyphenylmethyl)-1-(β-D-glucopyranosyl)-indole (1) A mixture of 4,6-dichloroindoline (6.57 g) and D-glucose (10.70 g) in H$_2$O (25 ml)-ethyl alcohol (160 ml) was refluxed for 3 days. The organic solvent was evaporated under reduced pressure, and thereto were added brine and ammonium sulfate. The mixture was extracted with ethyl acetate 5 times, and the combined organic layer was dried over sodium sulfate. The insoluble materials were filtered off, and the filtrate was evaporated under reduced pressure to give crude 4,6-dichloro-1-(β-D-gluco-pyranosyl)indoline, which was used in the subsequent step without further purification.

(2) The above compound was suspended in chloroform (150 ml), and thereto were added successively pyridine (27.57 ml), acetic anhydride (32.23 ml) and 4-(dimethylamino)pyridine (a catalytic amount). After being stirred overnight at room temperature, the reaction solvent was evaporated under reduced pressure. The residue was dissolved in ethyl acetate, and the solution was washed with a 10% aqueous copper(II) sulfate solution 3 times, a saturated aqueous sodium hydrogen carbonate solution and brine, and dried over sodium sulfate. The insoluble materials were filtered off, and the filtrate was evaporated under reduced pressure. The residue was purified by crystallization from ethyl alcohol to give 4,6-dichloro-1-(2,3,4,6-tetra-O-acetyl-β-D-glucopyranosyl)indoline (5.362 g) as colorless crystals. APCI-Mass m/Z 518/520 (M+H). $^1$H-NMR (DMSO-d6) 1.96 (s, 6H), 1.97 (s, 3H), 2.00 (s, 3H), 2.86 (m, —H), 3.00 (m, 1H), 3.56 (m, 2H), 4.01 (m, 1H), 4.08 (m, 2H), 4.96 (t, J=9.8 Hz, 1H), 5.14 (t, J=9.4 Hz, 1H), 5.36 (t, J=9.5 Hz, 1H), 5.50 (d, J=9.3 Hz, 1H), 6.80 (s, 1H), 6.84 (s, 1H).

(3) The above compound (5.36 g) was dissolved in 1,4-dioxane (70 ml)-H$_2$O (4 ml), and thereto was added 2,3-dichloro-5,6-dicyano-1,4-benzoquinone (5.19 g). After being stirred at room temperature for 5 days, thereto was added a saturated aqueous sodium hydrogen carbonate solution, and the organic solvent was evaporated under reduced pressure. The residue was extracted with ethyl acetate twice, and the combined organic layer was washed with brine, dried over sodium sulfate. The insoluble materials were filtered off, and the filtrate was evaporated under reduced pressure. The residue was purified by aminosilane-treated silica gel column chromatography (hexane:ethyl acetate=3:1-3:2) to give 4,6-dichloro-1-(2,3,4,6-tetra-O-acetyl-β-D-gluco-pyranosyl)indole (4.08 g) as a colorless solid. APCI-Mass m/Z 533/535 (M+NH$_4$). $^1$H-NMR (DMSO-d6) 1.67 (s, 3H), 1.97 (s, 3H), 2.00 (s, 3H), 2.05 (s, 3H), 4.10-4.20 (m, 2H), 4.25 (m, 1H), 5.31 (t, J=9.7 Hz, 1H), 5.48 (t, J=9.5 Hz, 1H), 5.62 (t, J=9.4 Hz, 1H), 6.22 (d, J=9.2 Hz, 1H), 6.58 (d, J=3.4 Hz, 1H), 7.29 (d, J=1.1 Hz, 1H), 7.66 (d, J=3.5 Hz, 1H), 7.87 (s, 1H).

(4) The above 4,6-dichloro-1-(2,3,4,6-tetra-O-acetyl-β-D-glucopyranosyl)-indole and 4-ethoxybenzoyl chloride were treated in a manner similar to Example 3 to give the titled compound, 4,6-dichloro-3-(4-ethoxyphenylmethyl)-1-(β-D-glucopyranosyl)-indole as a colorless powder. APCI-Mass m/Z 499/501 (M+NH$_4$). $^1$H-NMR (DMSO-d6) δ 1.29 (t, J=7.0 Hz, 3H), 3.15-3.52 (m, 4H), 3.58 (m, 1H), 3.67 (m, 1H), 3.97 (q, J=6.9 Hz, 2H), 4.17 (s, 2H), 4.54 (t, J=5.6 Hz, 1H), 5.10 (d, J=5.3 Hz, 1H), 5.15 (d, J=5.1 Hz, 1H), 5.21 (d, J=5.8 Hz, 1H), 5.45 (d, J=9.0 Hz, 1H), 6.81 (d, J=8.5 Hz, 2H), 7.11 (m, 3H), 7.26 (s, 1H), 7.71 (d, J=1.1 Hz, 1H).

Example 29

4-Chloro-3-(4-(trifluoromethoxy)phenylmethyl)-1-(β-D-gluco-pyranosyl)indole (1) 4-Chloro-1-(2,3,4,6-tetra-O-acetyl-β-D-glucopyranosyl)-indole obtained in Example 1-(3) was treated in a manner similar to Example 25-(1) to give 4-chloro-1-(2,3,4,6-tetra-O-acetyl-β-D-glucopyranosyl)indole-3-carboxaldehyde as a colorless powder. APCI-Mass m/Z 527/529 (M+NH$_4$). $^1$H-NMR (DMSO-d6) δ 1.64 (s, 3H), 1.98 (s, 3H), 1.99 (s, 3H), 2.05 (s, 3H), 4.09-4.19 (m, 2H), 4.30 (m, 1H), 5.34 (t, J=9.8 Hz, 1H), 5.54 (t, J=9.5 Hz, 1H), 5.70 (t, J=9.3 Hz, 1H), 6.37 (d, J=9.0 Hz, 1H), 7.35-7.42 (m, 2H), 7.82 (d, J=7.5 Hz, 1H), 8.54 (s, 1H), 10.51 (s, 1H).

(2) The above 4-chloro-1-(2,3,4,6-tetra-O-acetyl-β-D-gluco-pyranosyl)indole-3-carboxaldehyde and 1-bromo-4-(trifluoro-methoxy)benzene were treated in a manner similar to Example 25-(2) to give crude 4-chloro-1-(2,3,4,6-tetra-O-acetyl-β-D-gluco-pyranosyl)indol-3-yl 4-(trifluoromethoxy) phenyl methanol, which was used in the subsequent step without further purification.

(3) The above compound was treated in a manner similar to Example 25-(3) to give 4-chloro-3-(4-(trifluoromethoxy) phenylmethyl)-1-(2,3,4,6-tetra-O-acetyl-β-D-glucopyranosyl)indole as colorless needles. mp 193-194° C. APCI-Mass m/Z 673/675 (M+NH$_4$). $^1$H-NMR (DMSO-d6) δ 1.64 (s, 3H), 1.96 (s, 3H), 1.99 (s, 3H), 2.04 (s, 3H), 4.10 (A part of ABX, J=12.4, 2.5 Hz, 1H), 4.14 (B part of ABX, J=12.4, 5.4 Hz, 1H), 4.23-4.31 (m, 3H), 5.24 (t, J=9.5 Hz, 1H), 5.51 (t, J=9.2 Hz, 1H), 5.56 (t, J=9.2 Hz, 1H), 6.18 (d, J=8.5 Hz, 1H), 7.06 (d, J=7.5 Hz, 1H), 7.18 (t, J=7.9 Hz, 1H), 7.25 (s, 4H), 7.37 (s, 1H), 7.65 (d, J=8.3 Hz, 1H).

(4) The above 4-chloro-3-(4-(trifluoromethoxy)phenylmethyl)-1-(2,3,4,6-tetra-O-acetyl-β-D-glucopyranosyl)indole was treated in a manner similar to Example 2-(7) to give the titled compound, 4-chloro-3-(4-(trifluoromethoxy)phenylmethyl)-1-(β-D-glucopyranosyl)indole as a colorless powder. APCI-Mass m/Z 488/490 (M+NH$_4$). $^1$H-NMR (DMSO-d6) δ 3.23-3.27 (m, 1H), 3.40 (td, J=8.8, 5.2 Hz, 1H), 3.44-3.49 (m, 2H), 3.65-3.70 (m, 2H), 4.30 (s, 2H), 4.53 (t, J=5.4 Hz, 1H), 5.10 (d, J=5.3 Hz, 1H), 5.17 (d, J=5.0 Hz, 1H), 5.22 (d, J=5.8 Hz, 1H), 5.41 (d, J=9.0 Hz, 1H), 7.03 (d, J=7.5 Hz, 1H), 7.11 (t, J=7.9 Hz, 1H), 7.25 (d, J=8.2 Hz, 1H), 7.33 (d, J=8.5 Hz, 1H), 7.38 (s, 1H), 7.55 (d, J=8.2 Hz, 1H).

Example 30

4-Chloro-3-(4-(difluoromethyl)phenylmethyl)-1-(β-D-gluco-pyranosyl)indole (1) 4-Chloro-1-(2,3,4,6-tetra-O-acetyl-β-D-glucopyranosyl)-indole-3-carboxaldehyde obtained in Example 29-(1) and 1-bromo-4-difluoromethylbenzene were treated in a manner similar to Example 25-(2) to give crude 4-chloro-1-(2,3,4,6-tetra-O-acetyl-β-D-glucopyranosyl)indol-3-yl 4-(difluoromethyl)phenyl methanol, which was used in the subsequent step without further purification.

(2) The above compound was treated in a manner similar to Example 25-(3) to give 4-chloro-3-(4-(difluoromethyl)phenylmethyl)-1-(2,3,4,6-tetra-O-acetyl-β-D-glucopyranosyl)indole as a pale yellow solid. APCI-Mass m/Z 639/641 (M+NH$_4$). $^1$H-NMR (DMSO-d6) δ 1.65 (s, 3H), 1.96 (s, 3H), 1.99 (s, 3H), 2.04 (s, 3H), 4.10 (A part of ABX, J=12.3, 2.5 Hz, 1H), 4.14 (B part of ABX, J=12.5, 5.3 Hz, 1H), 4.26-4.34 (m, 3H), 5.24 (t, J=9.6 Hz, 1H), 5.51 (t, J=9.3 Hz, 1H), 5.56 (t, J=9.2 Hz, 1H), 6.19 (d, J=8.8 Hz, 1H), 6.97 (t, J=56.0 Hz, 1H), 7.06 (d, J=7.5 Hz, 1H), 7.18 (t, J=7.9 Hz, 1H), 7.27 (d, J=7.9 Hz, 2H), 7.36 (s, 1H), 7.46 (d, J=7.9 Hz, 2H), 7.65 (d, J=8.4 Hz, 1H).

(3) The above 4-chloro-3-(4-(difluoromethyl)phenylmethyl)-1-(2,3,4,6-tetra-O-acetyl-β-D-glucopyranosyl)indole was treated in a manner similar to Example 2-(7) to give the titled compound, 4-chloro-3-(4-(difluoromethyl)phenylmethyl)-1-(β-D-glucopyranosyl)indole as a colorless powder. APCI-Mass m/Z 454/456 (M+H). $^1$H-NMR (DMSO-d6) δ 3.25 (td, J=9.0, 5.5 Hz, 1H), 3.40 (td, J=8.8, 5.2 Hz, 1H), 3.44-3.49 (m, 2H), 3.64-3.70 (m, 2H), 4.33 (s, 2H), 4.54 (t, J=5.5 Hz, 1H), 5.10 (d, J=5.3 Hz, 1H), 5.18 (d, J=5.0 Hz, 1H), 5.23 (d, J=5.8 Hz, 1H), 5.41 (d, J=9.0 Hz, 1H), 6.98 (t, J=56.5 Hz, 1H), 7.02 (d, J=7.5 Hz, 1H), 7.11 (t, J=8.0 Hz, 1H), 7.35 (d, J=8.0 Hz, 2H), 7.36 (s, 1H), 7.47 (d, J=8.0 Hz, 2H), 7.56 (d, J=8.0 Hz, 1H).

Example 31

4-Chloro-3-(4-(difluoromethoxy)phenylmethyl)-1-(β-D-gluco-pyranosyl)indole (1) A mixture solution of 4-chloro-1-(2,3,4,6-tetra-O-acetyl-β-D-glucopyranosyl)indole-3-carboxaldehyde (50 mg) obtained in Example 29-(1), 4-(difluoromethoxy)benzeneboronic acid (55 mg), hydroxyl(1,5-cyclooctadiene) rhodium(I) dimer (1.3 mg) and tri-tert-butylphosphine (0.6 mg) in H$_2$O (1.0 ml)-1,2-dimethoxy-ethane (2.0 ml) was stirred at 80° C. under argon atmosphere for 19 hours. The reaction mixture was cooled to room temperature, and extracted with ethyl acetate (20 ml). The organic layer was filtered through an aminosilane-treated silica gel pad, and the filtrate was evaporated under reduced pressure to give crude 4-chloro-1-(2,3,4,6-tetra-O-acetyl-β-D-glucopyranosyl)-indol-3-yl 4-(difluoromethoxy)phenyl methanol, which was used in the subsequent step without further purification.

(2) The above compound was treated in a manner similar to Example 25-(3) to give 4-chloro-3-(4-(difluoromethoxy)phenylmethyl-1-(2,3,4,6-tetra-O-acetyl-β-D-glucopyranosyl) indole (28 mg) as a colorless solid. APCI-Mass m/Z 655/657 (M+NH$_4$). $^1$H-NMR (DMSO-d6) δ 1.65 (s, 3H), 1.96 (s, 3H), 1.99 (s, 3H), 2.04 (s, 3H), 4.11-4.13 (m, 2H), 4.23 (d, J=9.3 Hz, 2H), 4.27-4.30 (m, 1H), 5.24 (t, J=9.6 Hz, 1H), 5.51 (t, J=9.3 Hz, 1H), 5.56 (t, J=9.2 Hz, 1H), 6.18 (d, J=8.7 Hz, 1H), 7.05-7.07 (m, 1H), 7.06 (d, J=7.5 Hz, 2H), 7.16 (t, J=74.4 Hz, 1H), 7.17 (t, J=8.0 Hz, 1H), 7.19 (d, J=8.5 Hz, 2H), 7.33 (s, 1H), 7.64 (d, J=8.2 Hz, 1H).

(3) The above 4-chloro-3-(4-(difluoromethoxy)phenylmethyl)-1-(2,3,4,6-tetra-O-acetyl-β-D-glucopyranosyl)indole was treated in a manner similar to Example 2-(7) to give the titled compound, 4-chloro-3-(4-(difluoromethoxy)phenylmethyl)-1-(β-D-glucopyranosyl)indole as a colorless powder. APCI-Mass m/Z 470/472 (M+H). $^1$H-NMR (DMSO-d6) δ 3.24 (td, J=9.0, 5.4 Hz, 1H), 3.40 (td, J=8.9, 5.4 Hz, 1H), 3.42-3.48 (m, 2H), 3.64-3.69 (m, 2H), 4.26 (s, 2H), 4.54 (t, J=5.5 Hz, 1H), 5.10 (d, J=5.3 Hz, 1H), 5.18 (d, J=5.0 Hz, 1H), 5.22 (d, J=5.8 Hz, 1H), 5.40 (d, J=9.2 Hz, 1H), 7.03 (d, J=7.5 Hz, 1H), 7.07 (d, J=8.2 Hz, 2H), 7.11 (t, J=7.9 Hz, 1H), 7.15 (t, J=74.5 Hz, 1H), 7.26 (d, J=8.3 Hz, 2H), 7.32 (s, 1H), 7.54 (d, J=8.3 Hz, 1H).

Example 32

3-(Benzo[b]furan-5-yl-methyl)-4,6-dichloro-1-(β-D-gluco-pyranosyl)indole 4,6-Dichloro-1-(2,3,4,6-tetra-O-acetyl-β-D-glucopyranosyl)-indole obtained in Example 28-(3) and benzo[b]furan-5-carbonyl chloride were treated in a manner similar to Example 3 to give the titled compound as a colorless powder. APCI-Mass m/Z 478/480 (M+H). $^1$H-NMR (DMSO-d6) δ 3.20-3.50 (m, 4H), 3.59 (m, 1H), 3.67 (m, 1H), 4.34 (s, 2H), 4.55 (t, J=5.7 Hz, 1H), 5.11 (d, J=5.1 Hz, 1H), 5.16 (d, J=5.1 Hz, 1H), 5.24 (d, J=5.8 Hz, 1H), 5.46 (d, J=9.0 Hz, 1H), 6.87 (d, J=1.4 Hz, 1H), 7.11 (d, J=1.6 Hz, 1H), 7.19 (dd, J=8.5, 1.4 Hz, 1H), 7.33 (s, 1H), 7.42 (s, 1H), 7.49 (d, J=8.3 Hz, 1H), 7.73 (d, J=1.6 Hz, 1H), 7.93 (d, J=2.1H, z, 1H).

Example 33

4-Chloro-3-(4-iodophenylmethyl)-1-(β-D-glucopyranosyl)-indole (1) 4-Chloro-1-(2,3,4,6-tetra-O-acetyl-β-D-glucopyranosyl)-indole obtained in Example 1-(3) and 4-iodobenzoyl chloride were treated in a manner similar to Example 2-(4) to give 4-chloro-1-(2,3,4,6-tetra-O-acetyl-β-D-glucopyranosyl)-indol-3-yl 4-iodophenyl ketone as a colorless powder. APCI-Mass m/Z 711/713 (M+H). $^1$H-NMR (DMSO-d6) δ 1.69 (s, 3H), 1.97 (s, 3H), 1.98 (s, 3H), 2.04 (s, 3H), 4.10 (d, J=4.0 Hz, 2H), 4.29 (m, 1H), 5.28 (t, J=9.8 Hz, 1H), 5.53 (t, J=9.6 Hz, 1H), 5.73 (t, J=9.2 Hz, 1H), 6.33 (d, J=9.0 Hz, 1H), 7.29 (d, J=7.7 Hz, 1H), 7.38 (t, J=8.0 Hz, 1H), 7.57 (d, J=8.3 Hz, 2H), 7.79 (d, J=8.4 Hz, 1H), 7.94 (d, J=8.3 Hz, 2H), 8.17 (s, 1H).

(2) The above 4-chloro-1-(2,3,4,6-tetra-O-acetyl-β-D-gluco-pyranosyl)indol-3-yl 4-iodophenyl ketone was treated in a manner similar to Example 2-(5) to give crude 4-chloro-1-(2,3,4,6-tetra-O-acetyl-β-D-glucopyranosyl)indol-3-yl 4-iodophenyl methanol, which was used in the subsequent step without further purification.

(3) The above compound was treated in a manner similar to Example 27-(3) to give 4-chloro-3-(4-iodophenylmethyl)-1-(2,3,4,6-tetra-O-acetyl-β-D-glucopyranosyl)indole as a colorless solid. APCI-Mass m/Z 715/717 (M+NH$_4$). $^1$H-NMR (DMSO-d6) δ 1.65 (s, 3H), 1.96 (s, 3H), 1.99 (s, 3H), 2.04 (s, 3H), 4.08-4.16 (m, 2H), 4.17 (d, J=16.2 Hz, 1H), 4.22 (d, J=16.4 Hz, 1H), 4.28 (m, 1H), 5.24 (t, J=9.6 Hz, 1H), 5.51 (t, J=9.4 Hz, 1H), 5.56 (t, J=9.2 Hz, 1H), 6.18 (d, J=8.8 Hz, 1H), 6.96 (d, J=8.2 Hz, 2H), 7.05 (d, J=7.7 Hz, 2H), 7.17 (t, J=8.0 Hz, 1H), 7.33 (s, 1H), 7.60 (d, J=8.2 Hz, 2H), 7.65 (d, J=8.8 Hz, 1H).

(4) The above 4-chloro-3-(4-iodophenylmethyl)-1-(2,3,4,6-tetra-O-acetyl-β-D-glucopyranosyl)indole was treated in a manner similar to Example 2-(7) to give the titled compound, 4-chloro-3-(4-iodophenylmethyl)-1-(β-D-glucopyranosyl)-indole as a colorless powder. APCI-Mass m/Z 530/532 (M+H). $^1$H-NMR (DMSO-d6) δ 3.23-3.49 (m, 4H), 3.64-3.71 (m, 2H), 4.22 (s, 2H), 4.54 (t, J=5.5 Hz, 1H), 5.11 (d, J=5.3 Hz, 1H), 5.18 (d, J=5.0 Hz, 1H), 5.23 (d, J=5.8 Hz, 1H), 5.40 (d, J=9.2 Hz, 1H), 7.02 (d, J=8.0 Hz, 2H), 7.02 (d, J=7. Hz, 1H), 7.10 (t, J=7.9 Hz, 1H), 7.32 (s, 1H), 7.55 (d, J=8.3 Hz, 1H), 7.61 (d, J=8.2 Hz, 2H).

Example 34

3-(Benzo[b]furan-5-yl-methyl)-4-chloro-5-fluoro-1-(β-D-gluco-pyranosyl)indole (1) A mixture of 4-chloro-5-fluoroindoline (584 mg) and D-glucose (1.04 g) in ethyl alcohol (20 ml)-H$_2$O (3 ml) was refluxed for 1.5 days. The solvent was evaporated under reduced pressure and the residue was purified by silica gel column chromatography (chloroform:methanol=100:0-85:15) to give 4-chloro-5-fluoro-1-(β-D-glucopyranosyl)indoline (1.07 g) as a colorless foam. APCI-Mass m/Z 334/336 (M+H). $^1$H-NMR (DMSO-d6) δ 3.02 (m, 3H), 3.20-3.45 (m, 4H), 3.57 (m, 2H), 3.71 (m, 1H), 4.35 (t, J=5.8 Hz, —H), 4.60 (d, J=8.3 Hz, 1H), 4.93 (d, J=5.1 Hz, 1H), 5.04 (d, J=4.0 Hz, 1H), 5.07 (d, J=4.3 Hz, 1H), 6.51 (dd, J=8.6, 3.6 Hz, 1H), 7.00 (t, J=9.1 Hz, 1H).

(2) The above compound (1.06 g) was dissolved in 1,4-dioxane (40 ml), and thereto was added 2,3-dichloro-5,6-dicyano-1,4-benzoquinone (865 mg). The mixture was stirred at room temperature for 6 hours. To the reaction mixture was added a saturated aqueous sodium hydrogen carbonate solution, the organic solvent was evaporated under reduced pressure. The residue was extracted with ethyl acetate, and the organic layer was dried over sodium sulfate. The insoluble materials were filtered off, and the filtrate was evaporated under reduced pressure to give crude 4-chloro-5-fluoro-1-(β-D-glucopyranosyl)indole, which was used in the subsequent step without further purification.

(3) The above compound was suspended in dichloromethane (50 ml), and thereto were added successively acetic anhydride (2.99 ml), pyridine (2.57 ml) and 4-(dimethylamino)pyridine (a catalytic amount). After being stirred at room temperature overnight, the organic solvent was evaporated under reduced pressure. The residue was diluted with ethyl acetate, and the mixture was washed successively with a 10% aqueous citric acid solution, a saturated aqueous sodium hydrogen carbonate solution and brine. The organic layer was dried over sodium sulfate. The insoluble materials were filtered off, and the filtrate was evaporated under reduced pressure. The residue was purified by silica gel column chromatography (hexane:ethyl acetate=2:1-1:1) to give 4-chloro-5-fluoro-1-(2,3,4,6-tetra-O-acetyl-β-D-glucopyranosyl)indole (1.24 g) as a colorless solid. APCI-Mass m/Z 517/519 (M+NH$_4$). $^1$H-NMR (DMSO-d6) δ 1.66 (s, 3H), 1.97 (s, 3H), 1.99 (s, 3H), 2.04 (s, 3H), 4.12 (m, 2H), 4.28 (m, 1H), 5.28 (t, J=9.8 Hz, 1H), 5.51 (t, J=9.5 Hz, 1H), 5.60 (t, J=9.3 Hz, 1H), 6.21 (d, J=9.1 Hz, 1H), 6.59 (d, J=3.4 Hz, 1H), 7.26 (t, J=9.4 Hz, 1H), 7.68 (d, J=3.4 Hz, 1H), 7.70 (dd, J=9.0, 3.7 Hz, 1H).

(4) The above 4-chloro-5-fluoro-1-(2,3,4,6-tetra-O-acetyl-β-D-glucopyranosyl)indole and benzo[b]furan-5-carbonyl chloride were treated in a manner similar to Example 27 to give the titled compound, 3-(benzo[b]furan-5-yl-methyl)-4-chloro-5-fluoro-1-(β-D-glucopyranosyl)indole as a colorless powder. APCI-Mass m/Z 462/464 (M+H). $^1$H-NMR (DMSO-d6) δ 3.15-3.45 (m, 4H), 3.65 (m, 2H), 4.35 (s, 2H), 4.54 (t, J=5.5 Hz, 1H), 5.11 (d, J=5.3 Hz, 1H), 5.17 (d, J=5.0 Hz, 1H), 5.24 (d, J=5.8 Hz, 1H), 5.40 (d, J=9.0 Hz, 1H), 6.87 (d, J=1.4 Hz, 1H), 7.16 (t, J=9.2 Hz, 1H), 7.21 (dd, J=8.4, 1.0 Hz, 1H), 7.37 (s, 1H), 7.44 (s, 1H), 7.49 (d, J=8.5 Hz, 1H), 7.57 (dd, J=9.0, 4.0 Hz, 1H), 7.93 (d, J=1.9 Hz, 1H).

Example 35

4-Chloro-3-(4-ethoxyphenylmethyl)-5-fluoro-1-(β-D-gluco-pyranosyl)indole

4-Chloro-5-fluoro-1-(2,3,4,6-tetra-O-acetyl-β-D-glucopyranosyl)indole obtained in Example 34-(3) and 4-ethoxybenzoyl chloride were treated in a manner similar to Example 27 to give the titled compound as a colorless powder. APCI-Mass m/Z 483/485 (M+NH$_4$). $^1$H-NMR (DMSO-d6) δ 1.30 (t, J=6.9 Hz, 3H), 3.15-3.50 (m, 4H), 3.64 (m, 2H), 3.96 (q, J=6.9 Hz, 2H), 4.18 (s, 2H), 4.54 (t, J=5.4 Hz, 1H), 5.11 (t, J=5.3 Hz, 1H), 5.17 (d, J=5.0 Hz, 1H), 5.23 (d, J=5.8 Hz, 1H), 5.39 (d, J=9.1 Hz, 1H), 6.82 (d, J=8.5 Hz, 2H), 7.12 (d, J=8.5 Hz, 2H), 7.16 (t, J=9.4 Hz, 1H), 7.30 (s, 1H), 7.56 (dd, J=8.9, 3.9 Hz, 1H).

Example 36

4,6-Dichloro-3-(4-iodophenylmethyl)-1-(β-D-glucopyranosyl)-indole 4,6-Dichloro-3-(2,3,4,6-tetra-O-acetyl-β-D-glucopyranosyl)-indole obtained Example 28-(3) and 4-iodobenzoyl chloride were treated in a manner similar to Example 3 to give the titled compound as a colorless powder. APCI-Mass m/Z 564/566 (M+H). $^1$H-NMR (DMSO-d6) δ 3.20-3.54 (m, 4H), 3.57-3.71 (m, 2H), 4.20 (s, 2H), 4.53-4.63 (br, 1H), 5.10-5.16 (br, 1H), 5.18-5.30 (br, 2H), 5.46 (d, J=9.1 Hz, 1H), 7.01 (d, J=8.2 Hz, 2H), 7.11 (d, J=1.4 Hz, 1H), 7.38 (s, 1H), 7.61 (d, J=8.2 Hz, 2H), 7.73 (d, J=1.4 Hz, 1H).

Example 37

4-Chloro-5-fluoro-3-(4-iodophenylmethyl)-1-(β-D-gluco-pyranosyl)indole

4-Chloro-5-fluoro-1-(2,3,4,6-tetra-O-acetyl-β-D-glucopyranosyl)indole obtained in Example 34-(3) and 4-Iodobenzoyl chloride were treated in a manner similar to Example 3 to give the titled compound as a colorless powder. APCI-Mass m/Z 548/550 (M+H). $^1$H-NMR (DMSO-d6) δ 3.15-3.45 (m, 4H), 3.62 (m, 2H), 4.21 (s, 2H), 4.52-4.58 (br, 1H), 5.10-5.17 (br, 1H), 5.18-5.30 (br, 2H), 5.40 (d, J=9.0 Hz, 1H), 7.02 (d, J=8.2 Hz, 2H), 7.16 (t, J=9.3 Hz, 1H), 7.42 (s, 1H), 7.57 (dd, J=9.0, 4.0 Hz, 1H), 7.62 (d, J=8.3 Hz, 2H).

Example 38

3-(4-Bromophenylmethyl)-4-methyl-1-(β-D-glucopyranosyl)-indole

4-Methyl-1-(2,3,4,6-tetra-O-acetyl-β-D-glucopyranosyl) indole obtained in Example 23-(1) and 4-bromobenzoyl chloride were treated in a manner similar to Example 27 to give the titled compound as a colorless powder. APCI-Mass m/Z 462/464 (M−H). $^1$H-NMR (DMSO-d6) δ 2.38 (s, 3H), 3.24 (m, 1H), 3.30-3.47 (m, 4H), 3.68 (m, 1H), 4.18 (s, 2H), 4.52 (t, J=5.5 Hz, 1H), 5.08 (d, J=5.3 Hz, 1H), 5.15 (d, J=5.0 Hz, 1H), 5.17 (d, J=5.8 Hz, 1H), 5.34 (d, J=9.2 Hz, 1H), 6.71 (d, J=7.1 Hz, 1H), 6.98 (t, J=7.7 Hz, 1H), 7.13 (d, J=8.3 Hz, 2H), 7.15 (s, 1H), 7.35 (d, J=8.3 Hz, 1H), 7.46 (d, J=8.3 Hz, 2H).

Example 39

3-(4-Iodophenylmethyl)-4-methyl-1-(β-D-glucopyranosyl)indole

4-Methyl-1-(2,3,4,6-tetra-O-acetyl-β-D-glucopyranosyl) indole obtained in Example 23-(1) and 4-iodobenzoyl chloride were treated in a manner similar to Example 27 to give the titled compound as a colorless powder. APCI-Mass m/Z 510 (M+H). $^1$H-NMR (DMSO-d6) δ 2.38 (s, 3H), 3.24 (m, 1H), 3.30-3.47 (m, 4H), 3.68 (m, 1H), 4.16 (s, 2H), 4.52 (t, J=5.6 Hz, 1H), 5.08 (d, J=5.3 Hz, 1H), 5.14 (d, J=5.0 Hz, 1H), 5.16 (d, J=5.9 Hz, 1H), 5.34 (d, J=9.0 Hz, 1H), 6.71 (d, J=7.1 Hz, 1H), 6.98 (dd, J=8.3, 6.9 Hz, 1H), 6.99 (d, J=8.2 Hz, 2H), 7.15 (s, 1H), 7.35 (d, J=8.3 Hz, 1H), 7.46 (d, J=8.2 Hz, 2H).

Example 40

3-(Benzo[b]furan-5-yl-methyl)-4-methyl-1-(β-D-glucopyranosyl)indole

The titled compound was prepared from 4-methyl-1-(2,3,4,6-tetra-O-acetyl-β-D-glucopyranosyl)indole obtained in Example 23-(1) and benzo[b]furan-5-carbonyl chloride in a manner similar to Example 3 as a colorless powder. APCI-Mass m/Z 424 (M−H). $^1$H-NMR (DMSO-d6) δ 2.40 (s, 3H), 3.23 (td, J=8.9, 5.5 Hz, 1H), 3.39 (td, J=8.8, 5.1 Hz, 1H), 3.42-3.47 (m, 2H), 3.65-3.70 (m, 2H), 4.30 (s, 2H), 4.52 (t, J=5.5 Hz, 1H), 5.07 (d, J=5.3 Hz, 1H), 5.13 (d, J=5.0 Hz, 1H), 5.17 (d, J=5.8 Hz, 1H), 5.35 (d, J=9.0 Hz, 1H), 6.70 (d, J=7.1 Hz, 1H), 6.87 (d, J=1.4 Hz, 1H), 6.98 (m, 1H), 7.14 (s, 1H), 7.17 (dd, J=8.6, 1.4 Hz, 1H), 7.35 (d, J=8.3 Hz, 1H), 7.38 (s, 1H), 7.50 (d, J=8.3 Hz, 1H), 7.93 (d, J=2.1 Hz, 1H).

Example 41

4-Bromo-3-(4-bromophenylmethyl)-1-(β-D-glucopyranosyl)indole

The titled compound was prepared from 4-bromo-1-(2,3,4,6-tetra-O-acetyl-β-D-glucopyranosyl)indole obtained in Example 22-(1) and 4-bromobenzoyl chloride in a manner similar to Example 3 as a colorless powder. APCI-Mass m/Z 526/528/530 (M+H). $^1$H-NMR (DMSO-d6) δ 3.20-3.48 (m, 4H), 3.66 (m, 2H), 4.27 (s, 2H), 4.54 (t, J=5.4 Hz, 1H), 5.10 (d, J=5.3 Hz, 1H), 5.17 (d, J=5.0 Hz, 1H), 5.23 (d, J=5.8 Hz, 1H), 5.41 (d, J=9.0 Hz, 1H), 7.04 (t, J=7.9 Hz, 1H), 7.16 (d, J=8.3 Hz, 2H), 7.21 (d, J=7.5 Hz, 1H), 7.33 (s, 1H), 7.45 (d, J=8.3 Hz, 2H), 7.60 (d, J=8.2 Hz, 1H).

Example 42

4-Bromo-3-(4-iodophenylmethyl)-1-(β-D-glucopyranosyl)indole

The titled compound was prepared from 4-bromo-1-(2,3,4,6-tetra-O-acetyl-β-D-glucopyranosyl)indole obtained in Example 22-(1) and 4-iodobenzoyl chloride in a manner similar to Example 27 as a colorless powder. APCI-Mass m/Z 574/576 (M−+H). $^1$H-NMR (DMSO-d6) δ 3.20-3.50 (m, 4H), 3.62-3.71 (m, 2H), 4.25 (s, 2H), 4.54 (t, J=5.5 Hz, 1H), 5.10 (d, J=5.3 Hz, 1H), 5.17 (d, J=5.0 Hz, 1H), 5.22 (d, J=5.8 Hz, 1H), 5.41 (d, J=9.2 Hz, 1H), 7.02 (d, J=8.2 Hz, 2H), 7.04 (t, J=8.2 Hz, 1H), 7.21 (d, J=7.4 Hz, 1H), 7.32 (s, 1H), 7.60 (d, J=8.2 Hz, 1H), 7:61 (d, J=8.2 Hz, 2H).

Example 43

3-(Benzo[b]furan-5-yl-methyl)-4-bromo-1-(β-D-glucopyranosyl)-indole

The titled compound was prepared from 4-bromo-1-(2,3,4,6-tetra-O-acetyl-β-D-glucopyranosyl)indole obtained in Example 22-(1) and benzo[b]furan-5-carbonyl chloride in a manner similar to Example 27 as a colorless powder. APCI-Mass m/Z 488/490 (M+H). $^1$H-NMR (DMSO-d6) δ 3.23 (td, J=9.1, 5.5 Hz, 1H), 3.37-3.47 (m, 3H), 3.61-3.69 (m, 2H), 4.39 (s, 2H), 4.53 (t, J=5.5 Hz, 1H), 5.09 (d, J=5.3 Hz, 1H), 5.15 (d, J=5.0 Hz, 1H), 5.22 (d, J=5.9 Hz, 1H), 5.40 (d, J=9.2 Hz, 1H), 6.87 (d, J=1.4 Hz, 1H), 7.04 (t, J=7.9 Hz, 1H), 7.21 (m, 2H), 7.25 (s, 1H), 7.43 (s, 1H), 7.49 (d, J=8.5 Hz, 1H), 7.60 (d, J=8.2 Hz, 1H), 7.93 (d, J=2.1 Hz, 1H).

Example 44

4-Bromo-3-(4-chlorophenylmethyl)-1-(β-D-glucopyranosyl)indole

The titled compound was prepared from 4-bromo-1-(2,3,4,6-tetra-O-acetyl-β-D-glucopyranosyl)indole obtained in Example 22-(1) and 4-chlorobenzoyl chloride in a manner similar to Example 27 as a colorless powder. APCI-Mass m/Z 482/484 (M+H). $^1$H-NMR (DMSO-d6) δ 3.21-3.28 (m, 1H), 3.33-3.39 (m, 3H), 3.62-3.71 (m, 2H), 4.28 (s, 2H), 4.54 (t, J=5.5 Hz, 1H), 5.11 (d, J=5.3 Hz, 1H), 5.17 (d, J=5.1 Hz, 1H), 5.23 (d, J=5.8 Hz, 1H), 5.41 (d, J=9.0 Hz, 1H), 7.04 (t, J=7.9 Hz, 1H), 7.19-7.24 (m, 3H), 7.30-7.35 (m, 2H), 7.33 (brs, 1H), 7.60 (d, J=8.3 Hz, 1H).

Example 45

3-(5-(3-Cyanophenyl)-thiophen-2-yl-methyl)-4-methyl-1-(β-D-glucopyranosyl)indole (1) 4-Methyl-1-(2,3,4,6-tetra-O-acetyl-β-D-glucopyranosyl)-indole obtained in Example 23-(1) and 5-bromothiophene-2-carbonyl chloride were treated in a manner similar to Example 21-(1) to give 5-bromo-2-thienyl 4-methyl-1-(2,3,4,6-tetra-O-acetyl-β-D-glucopyranosyl)indol-3-yl ketone as a yellow powder. APCI-Mass m/Z 650/652 (M+H).

(2) The above compound (978 mg) was treated in a manner similar to Example 2-(5) to give crude 5-bromo-2-thienyl 4-methyl-1-(2,3,4,6-tetra-O-acetyl-β-D-glucopyranosyl)indol-3-yl methanol, which was used in the subsequent step without further purification.

(3) To a stirred solution of the above compound in acetonitrile (20 ml)-dichloromethane (10 ml) were added triethylsilane (1.20 ml) and boron trifluoride.diethyl ether complex (0.953 ml) at 0° C. under argon atmosphere. After being stirred at same temperature for 40 minutes, thereto was added a saturated aqueous sodium hydrogen carbonate solution (30 ml), and the organic solvent was evaporated under reduced pressure. The residue was extracted with ethyl acetate (100 ml) twice, and the combined organic layer was dried over magnesium sulfate. The insoluble materials were filtered off, and the filtrate was evaporated under reduced pressure to give crude 3-(5-bromothiophen-2-yl-methyl)-4-methyl-1-(2,3,4,6-tetra-O-acetyl-β-D-glucopyranosyl)indole, which was partially deacetylated. This crude compound was dissolved in chloroform (30 ml), and thereto were added successively pyridine (0.365 ml), acetic anhydride (0.426 ml) and 4-(dimethylamino)pyridine (18.4 mg). After being stirred at room temperature for 4 hour, the solvent was evaporated under reduced pressure. The residue was dissolved in ethyl acetate (250 ml), and the mixture was washed with a 10% aqueous copper(II) sulfate solution (20 ml) twice, $H_2O$ (20 ml) and a saturated aqueous sodium hydrogen carbonate solution (20 ml), and dried over magnesium sulfate. The insoluble materials were filtered off, and the filtrate was evaporated under reduced pressure. The residue was purified by silica gel column chromatography (hexane:ethyl acetate=90:10-60:40) and recrystallized from ethyl alcohol to give 3-(5-bromothiophen-2-yl-methyl)-4-methyl-1-(2,3,4,6-tetra-O-acetyl-β-D-glucopyranosyl)indole (347 mg) as pale yellow crystals. APCI-Mass m/Z 636/638 (M+H).

(4) A mixture of the above compound (150 mg), 3-cyanobenzene-boronic acid (52 mg), cesium fluoride (215 mg) and tetrakis-(triphenylphosphine)palladium(0) (27.2 mg) in 1,2-dimethoxy-ethane (5 ml) was stirred at 100° C. for 2 hours under argon atmosphere. The reaction mixture was diluted with ethyl acetate, and the resultant mixture was filtered through an aminosilane-treated silica gel pad. The filtrate was evaporated under reduced pressure, and the residue was purified by silica gel column chromatography (hexane ethyl acetate=80:20-50:50) to give 3-(5-(3-cyanophenyl) thiophen-2-yl-methyl)-4-methyl-1-(2,3,4,6-tetra-O-acetyl-β-D-glucopyranosyl)indole (120 mg) as a colorless powder. APCI-Mass m/Z 676 (M+$NH_4$).

(5) The above compound was treated in a manner similar to Example 2-(7) to give the titled compound, 3-(5-(3-cyanophenyl)-thiophen-2-yl-methyl)-4-methyl-1-(β-D-glucopyranosyl)indole as a colorless powder. APCI-Mass m/Z 491 (M+H). ¹H-NMR (DMSO-d6) δ 2.50 (s, 3H), 3.23-3.48 (m, 4H), 3.69 (m, 2H), 4.40 (s, 2H), 4.54 (m, 1H), 5.09 (d, J=5.3 Hz, 1H), 5.16 (d, J=5.0 Hz, 1H), 5.18 (d, J=5.9 Hz, 1H), 5.37 (d, J=9.2 Hz, 1H), 6.75 (d, J=7.1 Hz, 1H), 6.87 (d, J=3.5 Hz, 1H), 7.00 (t, J=7.4 Hz, 1H), 7.34 (s, 1H), 7.37 (d, J=8.3 Hz, 1H), 7.53 (d, J=3.7 Hz, 1H), 7.55 (d, J=8.0 Hz, 1H), 7.68 (d, J=7.7 Hz, 1H), 7.87 (d, J=8.0 Hz, 1H), 8.07 (s, 1H).

Example 46

4-Chloro-3-(4-hydroxyphenylmethyl)-1-(β-D-glucopyranosyl)-indole (1) 4-Chloro-1-(2,3,4,6-tetra-O-acetyl-β-D-glucopyranosyl)-indole obtained in Example 1-(3) and 4-pivaloyloxybenzoyl chloride were treated in a manner similar to Example 2-(4), (5) and 27-(3) to give 4-chloro-3-(4-pivaloyloxyphenylmethyl)-1-(2,3,4,6-tetra-O-acetyl-β-D-glucopyranosyl) indole as a colorless powder. APCI-Mass m/Z 689/691 (M+$NH_4$).

(2) The above compound (915 mg) was dissolved in tetrahydrofuran (5 ml)-methanol (5 ml), and the mixture was cooled to an ice-water temperature. Thereto was added a 10 M aqueous sodium hydroxide solution (1.09 ml), and the mixture was stirred at room temperature for 4 hours. The resultant mixture was again cooled to an ice-water temperature, and acidified with a 2 N aqueous hydrochloric acid solution. The mixture was extracted with ethyl acetate twice, and the combined organic layer was washed with a saturated aqueous sodium hydrogen carbonate solution and dried over magnesium sulfate. The insoluble materials were filtered off, and the filtrate was evaporated under reduced pressure. The residue was purified by silica gel column chromatography (chloroform:methanol=9:1-5:1) to give the titled compound, 4-chloro-3-(4-hydroxyphenylmethyl)-1-(β-D-glucopyranosyl)-indole (568 mg) as a colorless powder. APCI-Mass m/Z 420/422 (M+H). ¹H-NMR (DMSO-d6) δ 3.23 (m, 1H), 3.33-3.47 (m, 3H), 3.60-3.70 (m, 2H), 4.15 (s, 1H), 4.53 (t, J=5.5 Hz, 1H), 5.09 (d, J=5.3 Hz, 1H), 5.19 (d, J=5.1 Hz, 1H), 5.20 (d, J=5.9 Hz, 1H), 5.38 (d, J=9.2 Hz, 1H), 6.66 (d, J=8.3 Hz, 2H), 7.02 (d, J=8.2 Hz, 3H), 7.09 (t, J=7.9 Hz, 1H), 7.16 (s, 1H), 7.52 (d, J=8.2 Hz, 1H), 9.12 (s, 1H).

Example 47

3-(4-Cyclopropylphenylmethyl)-4-methyl-1-(β-D-gluco-pyranosyl)indole (1) 4-Methyl-1-(2,3,4,6-tetra-O-acetyl-β-D-glucopyranosyl)-indole obtained in Example 23-(1) and 4-bromobenzoyl chloride were treated in a manner similar to Example 2-(4), (5) and 3-(3) to give 3-(4-bromophenylmethyl)-4-methyl-1-(2,3,4,6-tetra-O-acetyl-β-D-glucopyranosyl)indole as pale pink crystals. mp 190-192° C. APCI-Mass m/Z 630/632 (M+H).

(2) A mixture of the above compound (300 mg), cyclopropylboronic acid (123 mg), palladium(II) acetate (5.3 mg), potassium phosphate tribasic (354 mg) and tricyclohexylphosphine (13 mg) in toluene (15 ml)-$H_2O$ (0.75 ml) was stirred at 90° C. overnight under argon atmosphere. The reaction mixture was diluted with ethyl acetate, and the resultant mixture was washed with $H_2O$ and brine, and dried over sodium sulfate. The insoluble materials were filtered off, and the filtrate was evaporated under reduced pressure. The residue was purified by silica gel column chromatography (hexane:ethyl acetate=80:20-50:50) to give 3-(4-cyclopropylphenylmethyl)-4-methyl-1-(2,3,4,6-tetra-O-acetyl-β-D-glucopyranosyl)indole (214 mg) as a colorless solid. APCI-Mass m/Z 592 (M+H).

(2) The above compound (182 mg) was dissolved in tetrahydrofuran (5 ml)-methanol (10 ml), and thereto was added sodium methoxide (28% methanol solution, one drop). After being stirred at room temperature for 2 hours, the organic solvent was evaporated under reduced pressure. The residue was purified by silica gel column chromatography (chloroform:methanol 100:0-85:15) and HPLC (DAICEL CHIRALPAK IA, hexane:ethyl alcohol=90:10) to give the titled compound, 3-(4-cyclopropylphenylmethyl)-4-methyl-1-(β-D-glucopyranosyl)indole (73 mg) as a colorless powder. APCI-Mass m/Z 424 (M+H). $^1$H-NMR (DMSO-d6) δ 0.59-0.63 (m, 2H), 0.87-0.92 (m, 2H), 1.85 (m, 1H), 2.40 (s, 3H), 3.20-3.45 (m, 5H), 3.66 (m, 1H), 4.14 (s, 2H), 4.52 (t, J=5.5 Hz, 1H), 5.07 (d, J=5.3 Hz, 1H), 5.14 (d, J=5.1 Hz, 1H), 5.15 (d, J=6.0 Hz, 1H), 5.33 (d, J=9.2 Hz, 1H), 6.70 (d, J=7.0 Hz, 1H), 6.96 (m, 1H), 6.97 (d, J=8.0 Hz, 2H), 7.04 (d, J=8.0 Hz, 2H), 7.09 (s, 1H), 7.33 (d, J=8.3 Hz, 1H).

Example 48

3-(5-(4-Fluorophenyl)thiophen-2-yl-methyl)-4-methyl-1-(β-D-glucopyranosyl)indole 3-(5-Bromothiophen-2-yl-methyl)-4-methyl-1-(2,3,4,6-tetra-O-acetyl-β-D-glucopyranosyl)indole obtained in Example 45-(3) and 4-fluorobenzeneboronic acid were treated in a manner similar to Example 45-(4) and 2-(7) to give the titled compound as a yellow powder. APCI-Mass m/Z 484 (M+H). $^1$H-NMR (DMSO-d6) δ 2.50 (s, 3H), 3.25 (td, J=8.8, 5.4 Hz, 1H), 3.40 (td, J=9.0, 5.4 Hz, 1H), 3.43-3.48 (m, 2H), 3.67-3.71 (m, 2H), 4.37 (s, 2H), 4.54 (t, J=5.5 Hz, 1H), 5.09 (d, J=5.1 Hz, 1H), 5.15 (d, J=5.1 Hz, 1H), 5.17 (d, J=6.1 Hz, 1H), 5.36 (d, J=9.2 Hz, 1H), 6.75 (d, J=7.1 Hz, 1H), 6.80 (d, J=3.5 Hz, 1H), 7.00 (t, J=7.7 Hz, 1H), 7.19 (t, J=8.8 Hz, 2H), 7.30 (d, J=3.5 Hz, 1H), 7.32 (s, 1H), 7.36 (d, J=8.3 Hz, 1H), 7.59 (dd, J=8.7, 5.3 Hz, 2H).

Example 49

3-(5-(6-Fluoro-3-pyridyl)thiophen-2-yl-methyl)-4-methyl-1-(β-D-glucopyranosyl)indole 3-(5-Bromothiophen-2-yl-methyl)-4-methyl-1-(2,3,4,6-tetra-O-acetyl-β-D-glucopyranosyl)indole obtained in Example 45-(3) and 6-fluoropyridine-3-boronic acid were treated in a manner similar to Example 45-(4) and 2-(7) to give the titled compound as a colorless powder. APCI-Mass m/Z 485 (M+H). $^1$H-NMR (DMSO-d6) δ 2.50 (s, 3H), 3.20-3.50 (m, 4H), 3.70 (m, 2H), 4.40 (s, 2H), 4.54 (t, J=5.4 Hz, 1H), 5.09 (d, J=5.3 Hz, 1H), 5.16 (d, J=5.7 Hz, 1H), 5.17 (d, J=5.7 Hz, 1H), 5.36 (d, J=9.0 Hz, 1H), 6.75 (d, J=7.1 Hz, 1H), 6.87 (d, J=3.4 Hz, 1H), 7.00 (t, J=7.7 Hz, 1H), 7.19 (dd, J=8.6, 2.7 Hz, 1H), 7.33 (s, 1H), 7.37 (d, J=8.2 Hz, 1H), 7.44 (d, J=3.4 Hz, 1H), 8.16 (dt, J=8.2, 2.4 Hz, 1H), 8.45 (d, J=2.3 Hz, 1H).

Example 50

4-Methyl-3-(5-phenylthiophen-2-yl-methyl)-1-(β-D-gluco-pyranosyl)indole 3-(5-Bromothiophen-2-yl-methyl)-4-methyl-1-(2,3,4,6-tetra-O-acetyl-β-D-glucopyranosyl)indole obtained in Example 45-(3) and benzeneboronic acid were treated in a manner similar to Example 45-(4) and 2-(7) to give the titled compound as a pale yellow powder. APCI-Mass m/Z 466 (M+H). $^1$H-NMR (DMSO-d6) δ 2.50 (s, 3H), 3.25 (m, 1H), 3.35-3.49 (m, 2H), 3.66-3.73 (m, 2H), 4.38 (s, 2H), 4.54 (t, J=5.5 Hz, 1H), 5.09 (d, J=5.3 Hz, 1H), 5.15 (d, J=5.0 Hz, 1H), 5.17 (d, J=5.9 Hz, 1H), 5.37 (d, J=9.2 Hz, 1H), 6.75 (d, J=7.1 Hz, 1H), 6.80 (d, J=3.5 Hz, 1H), 7.00 (t, J=7.6 Hz, 1H), 7.24 (t, J=7.3 Hz, 1H), 7.31-7.38 (m, 5H), 7.56 (d, J=7.4 Hz, 2H).

Example 51

4-Methyl-3-(5-(2-thienyl)thiophen-2-yl-methyl)-1-(β-D-gluco-pyranosyl)indole (1) A mixture of 3-(5-bromothiophen-2-yl-methyl)-4-methyl-1-(2,3,4,6-tetra-O-acetyl-β-D-glucopyranosyl)indole obtained in Example 45-(3) (190 mg), thiophene-2-boronic acid (229 mg), cesium fluoride (272 mg) and tetrakis(triphenylphosphine)-palladium(0) (34.5 mg) in 1,2-dimethoxyethane (6 ml) was refluxed for 6 hours under argon atmosphere. The reaction mixture was diluted with ethyl acetate and a saturated aqueous sodium hydrogen carbonate solution, and the organic layer was filtered through an aminosilane-treated silica gel pad. The filtrate was evaporated under reduced pressure to give crude 4-methyl-3-(5-(2-thienyl)-thiophen-2-yl-methyl)-1-(2,3,4,6-tetra-O-acetyl-β-D-glucopyranosyl)indole, which was partially deacetylated. This crude compound was dissolved in chloroform (6 ml), and thereto were added successively pyridine (0.121 ml), acetic anhydride (0.141 ml) and 4-(dimethylamino)pyridine (3.7 mg). After being stirred at room temperature for 4 hour, the solvent was evaporated under reduced pressure. The residue was dissolved in ethyl acetate (80 ml), and the mixture was washed with a 10% aqueous copper (II) sulfate solution (5 ml) twice and a saturated aqueous sodium hydrogen carbonate solution (5 ml), and dried over magnesium sulfate. The insoluble materials were filtered off, and the filtrate was evaporated under reduced pressure. The residue was purified by silica gel column chromatography (hexane:ethyl acetate=90:10-50:50) to give 4-methyl-3-(5-(2-thienyl)thiophen-2-yl-methyl)-1-(2,3,4,6-tetra-O-acetyl-β-D-glucopyranosyl)indole (134 mg) as a yellow powder. APCI-Mass m/Z 657 (M+NH$_4$).

(2) The above compound was treated in a manner similar to Example 2-(7) to give the titled compound, 4-methyl-3-(5-(2-thienyl)-thiophen-2-yl-methyl)-1-(β-D-glucopyranosyl) indole as a pale yellow powder. APCI-Mass m/Z 489 (M+NH$_4$). $^1$H-NMR (DMSO-d6) δ 2.50 (s, 3H), 3.25 (td, J=8.9, 5.2 Hz, 1H), 3.40 (td, J=8.9, 5.2 Hz, 1H), 3.44-3.49 (m, 2H), 3.67-3.72 (m, 2H), 4.35 (s, 2H), 4.54 (t, J=5.5 Hz, 1H), 5.09 (d, J=5.1 Hz, 1H), 5.15 (d, J=5.0 Hz, 1H), 5.17 (d, J=5.9 Hz, 1H), 5.36 (d, J=9.2 Hz, 1H), 6.74-6.76 (m, 2H), 7.00 (m, 1H), 7.03 (dd, J=5.1, 3.7 Hz, 1H), 7.11 (d, J=3.5 Hz, 1H), 7.18 (dd, J=3.5, 0.9 Hz, 1H), 7.33 (s, 1H), 7.36 (d, J=8.2 Hz, 1H), 7.43 (dd, J=5.0, 0.8 Hz, 1H).

Example 52

4-Methyl-3-(5-(2-pyridyl)thiophen-2-yl-methyl)-1-(β-D-gluco-pyranosyl)indole (1) A mixture of 3-(5-bromothiophen-2-yl-methyl)-4-methyl-1-(2,3,4,6-tetra-O-acetyl-β-D-glucopyranosyl)indole obtained in Example 45-(3) (345 mg), 2-(tri-n-butylstannyl) pyridine (997 mg), copper(I) iodide (20 mg) and tetrakis (triphenylphosphine)-palladium(0) (63 mg) in toluene (10 ml) was refluxed for 3 hours under argon atmosphere. The reaction mixture was diluted with ethyl acetate, and thereto was added a 10% aqueous potassium fluoride solution. The resultant mixture was stirred vigorously, and the insoluble materials were filtered off. The filtrate was separated, and the organic layer was washed with brine and dried over sodium sulfate. The insoluble materials were filtered off, and the filtrate was evaporated under reduced pressure. The residue was purified by silica gel column chromatography (hexane ethyl acetate=90:10-50:50) to give 4-methyl-3-(5-(2-pyridyl)thiophen-2-yl-methyl)-1-(2,3,4,6-tetra-O-acetyl-β-D-glucopyranosyl)indole (122 mg) as a pale yellow solid. APCI-Mass m/Z 635 (M+H).

(2) The above compound was treated in a manner similar to Example 2-(7) to give the titled compound, 4-methyl-3-(5-(2-pyridyl)-thiophen-2-yl-methyl)-1-(β-D-glucopyranosyl)indole as a colorless solid. mp 195-200° C. APCI-Mass m/Z 467 (M+H). $^1$H-NMR (DMSO-d6) δ 2.50 (s, 3H), 3.20-3.50 (m, 4H), 3.71 (m, 2H), 4.38 (s, 2H), 4.56 (t, J=5.5 Hz, 1H), 5.08 (d, J=5.3 Hz, 1H), 5.15 (d, J=5.1 Hz, 1H), 5.17 (d, J=5.9 Hz, 1H), 5.37 (d, J=9.2 Hz, 1H), 6.74 (d, J=7.1 Hz, 1H), 6.84 (d, J=3.5 Hz, 1H), 6.99 (t, J=8.0 Hz, 1H), 7.19 (td, J=6.1, 0.7 Hz, 1H), 7.33 (s, 1H), 7.37 (d, J=8.5 Hz, 1H), 7.61 (d, J=3.7 Hz, 1H), 7.76 (td, J=7.7, 1.6 Hz, 1H), 7.80 (m, 1H), 8.42 (d, J=4.6 Hz, 1H).

The chemical structures of the above Examples are shown in Table 1 below:

TABLE 1

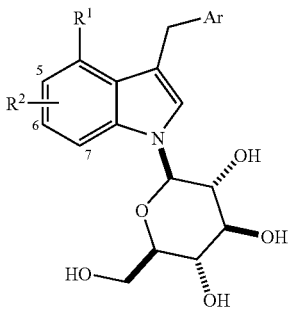

| Example No. | R$^1$ | R$^2$ | Ar |
|---|---|---|---|
| 1 | Cl | H | 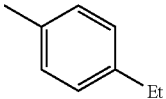 4-Et-phenyl |
| 2 | F | H | 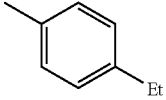 4-Et-phenyl |
| 3 | Cl | H | 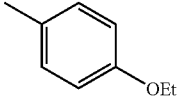 4-OEt-phenyl |
| 4 | Cl | H | 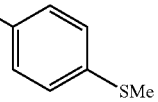 4-SMe-phenyl |
| 5 | Cl | H | 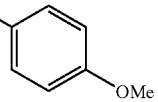 4-OMe-phenyl |
| 6 | Cl | H | 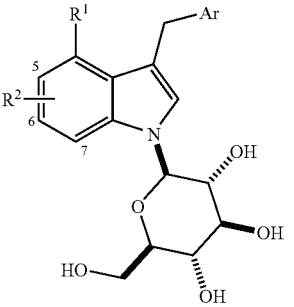 4-Cl-phenyl |
| 7 | Cl | H |  5-Br-thiophen-2-yl |
| 8 | F | H | 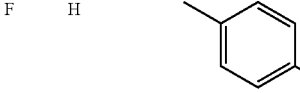 4-OEt-phenyl |
| 9 | F | H |  4-OMe-phenyl |
| 10 | F | H | 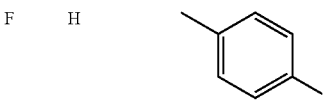 4-SMe-phenyl |
| 11 | Cl | H |  4-Me-phenyl |
| 12 | F | H | 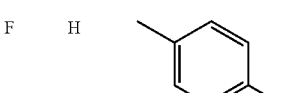 4-(2-fluoroethoxy)-phenyl |
| 13 | F | H | 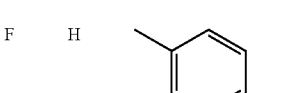 4-(2-chloroethoxy)-phenyl |
| 14 | Cl | H |  4-Br-phenyl |
| 15 | Cl | H | 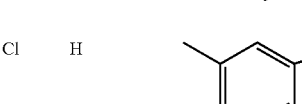 benzofuran-5-yl |
| 16 | Cl | H |  5-Et-thiophen-2-yl |

TABLE 1-continued

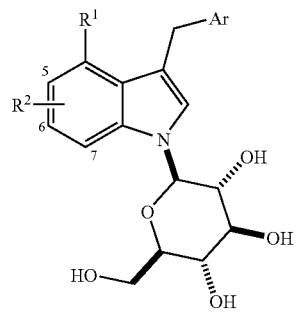

| Example No. | R¹ | R² | Ar |
|---|---|---|---|
| 17 | Cl | H | 4-(2-fluoroethoxy)phenyl |
| 18 | F | H | 5-ethylthiophen-2-yl |
| 19 | Cl | H | 4-(2-chloroethoxy)phenyl |
| 20 | F | H | benzofuran-5-yl |
| 21 | Cl | H | 2,3-dihydrobenzofuran-5-yl |
| 22 | Br | H | 4-ethylphenyl |
| 23 | Me | H | 4-ethylphenyl |
| 24 | F | H | 4-methylphenyl |
| 25 | F | H | 4-(difluoromethyl)phenyl |
| 26 | F | H | 4-(difluoromethoxy)phenyl |
| 27 | Cl | H | 4-fluorophenyl |

TABLE 1-continued

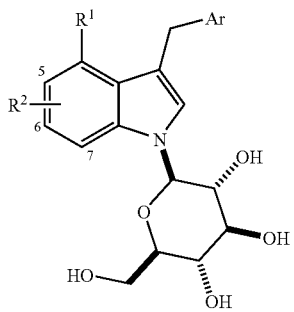

| Example No. | R¹ | R² | Ar |
|---|---|---|---|
| 28 | Cl | 6-Cl | 4-ethoxyphenyl |
| 29 | Cl | H | 4-(trifluoromethoxy)phenyl |
| 30 | Cl | H | 4-(difluoromethyl)phenyl |
| 31 | Cl | H | 4-(difluoromethoxy)phenyl |
| 32 | Cl | 6-Cl | benzofuran-5-yl |
| 33 | Cl | H | 4-iodophenyl |
| 34 | Cl | 5-F | benzofuran-5-yl |
| 35 | Cl | 5-F | 4-ethoxyphenyl |
| 36 | Cl | 6-Cl | 4-iodophenyl |
| 37 | Cl | 5-F | 4-iodophenyl |
| 38 | Me | H | 4-bromophenyl |

TABLE 1-continued

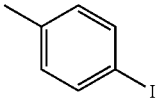

| Example No. | R¹ | R² | Ar |
|---|---|---|---|
| 39 | Me | H | 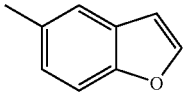 |
| 40 | Me | H | 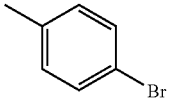 |
| 41 | Br | H | 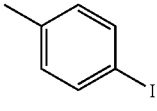 |
| 42 | Br | H | 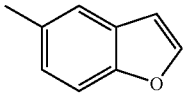 |
| 43 | Br | H | 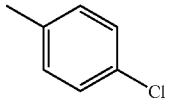 |
| 44 | Br | H | 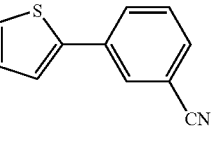 |
| 45 | Me | H | 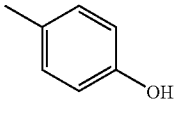 |
| 46 | Cl | H | 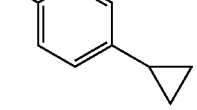 |
| 47 | Me | H | 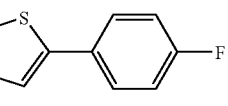 |
| 48 | Me | H | 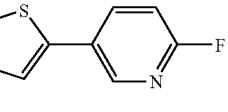 |
| 49 | Me | H | 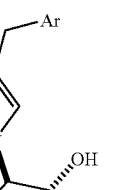 |
| 50 | Me | H | 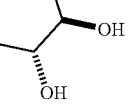 |
| 51 | Me | H | 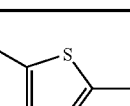 |
| 52 | Me | H | 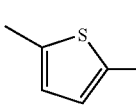 |

In the above table, Me is methyl, and Et is ethyl.

Reference Example 1

4-Chloroindoline

A solution of 4-chloroindole (3.15 g) and triethylsilane (8.30 ml) in trifluoroacetic acid (32 ml) was stirred at 50° C. for 30 minutes. The solvent was evaporated under reduced pressure, and the residue was basified with a saturated aqueous sodium hydrogen carbonate solution. The mixture was extracted with ethyl acetate twice, and the combined organic layer was dried over magnesium sulfate. The insoluble materials were filtered off, and the filtrate was evaporated under reduced pressure. The residue was purified by silica gel column chromatography (hexane:ethyl acetate=100:0-80:20) to give the titled compound (2.89 g) as colorless oil. APCI-Mass m/Z 154/156 (M+H). ¹H-NMR (DMSO-d6) δ 2.94 (t, J=8.7 Hz, 2H), 3.46 (t, J=8.7 Hz, 2H), 5.83 (s, 1H), 6.40 (d, J=7.7 Hz, 1H), 6.50 (d, J=8.0 Hz, 1H), 6.90 (t, J=7.9 Hz, 1H).

Reference Example 2

4-Fluoroindoline

To a stirred suspension of sodium borohydride (560 mg) in diethyl ether (6 ml) was added dropwise zinc chloride (1.0 M solution in diethyl ether, 7.4 ml). The mixture was stirred at room temperature under argon atmosphere for 1 day. To the resultant mixture was added dropwise a solution of 4-fluoroindole (500 mg) in diethyl ether (5 ml). After being stirred at room temperature under argon atmosphere for 12 days, thereto was added a cold 0.5 N aqueous hydrochloric acid solution (30 ml) at 0° C. After that, the mixture was basified with a cold 2 N aqueous sodium hydroxide solution at 0° C., and extracted with ethyl acetate 3 times. The combined organic layer was dried over magnesium sulfate, and the insoluble materials were filtered off, and the filtrate was evaporated under reduced pressure. The residue was purified by silica gel column chromatography (hexane:ethyl acetate=100:0-80:20) to give the titled compound (351 mg) as pale yellow oil. APCI-Mass m/Z 138 (M+H). $^1$H-NMR (DMSO-d6) δ 2.93 (t, J=8.6 Hz, 2H), 3.46 (t, J=8.6 Hz, 2H), 5.78 (br-s, 1H), 6.24-6.31 (m, 2H), 6.87-6.94 (m, 1H).

Reference Example 3

5-Bromothiophene-2-carbonyl chloride

To a stirred suspension of t-bromothiophene-2-carboxylic acid (875 mg) in dichloromethane (9 ml) were added oxalyl chloride (0.567 ml) and N,N-dimethylformamide (one drop) at 0° C., and then the mixture was warmed to room temperature. After being stirred at same temperature for 2 hour, the resultant solvent was evaporated under reduced pressure to give the titled compound, which was used in the subsequent step without further purification.

Reference Example 4

4-(2-Fluoroethyloxy)benzoyl chloride (1) A mixture of methyl 4-hydroxybenzoate (4.03 g), 1-bromo-2-fluoroethane (5.05 g) and potassium carbonate (10.98 g) in N,N-dimethylformamide (68 ml) was stirred at 70° C. for 1 hour. The reaction mixture was cooled to room temperature, and thereto was added water. The mixture was extracted with ethyl acetate, and the organic layer was washed successively with water and brine, and then dried over magnesium sulfate. The insoluble materials were filtered off, and the filtrate was evaporated under reduced pressure to give methyl 4-(2-fluoroethyloxy)benzoate, which was used in the subsequent step without further purification.

(2) The above compound was dissolved in methanol (50 ml)-tetrahydrofuran (20 ml), and thereto was added a 2 N aqueous sodium hydroxide solution (20 ml). The mixture was stirred at room temperature for 1 hour, and then refluxed for 2 hours. The reaction solvent was evaporated under reduced pressure, and the residue was dissolved in H$_2$O. The aqueous solution was washed with diethyl ether, and acidified with a 36% aqueous hydrochloric acid solution at 0° C. The mixture was extracted with ethyl acetate, and the organic layer was washed with brine, and dried over magnesium sulfate. The insoluble materials were filtered off, and the filtrate was evaporated under reduced pressure. The residual solid was triturated with hexane to give 4-(2-fluoroethyl-oxy)benzoic acid (4.8 g) as colorless fine needles. mp 202-203° C. ESI-Mass m/Z 183 (M−H). $^1$H-NMR (DMSO-d6) δ 4.31 (dt, J=30.1, 3.7 Hz, 2H), 4.76 (dt, J=47.8, 3.8 Hz, 2H), 7.05 (d, J=8.7 Hz, 2H), 7.90 (d, J=8.8 Hz, 2H).

(3) In a manner similar to the methods disclosed in Reference Example 3, the titled compound was prepared from the above compound.

Reference Example 5

4-(2-Chloroethyloxy)benzoyl chloride

In a manner similar to the methods disclosed in Reference Example 4, the titled compound was prepared from methyl 4-hydroxybenzoate and 1-bromo-2-chloroethane.

Reference Example 6

5-Ethylthiophene-2-carbonyl chloride

In a manner similar to the methods disclosed in Reference Example 3, the titled compound was prepared from 5-ethyl-thiophene-2-carboxylic acid.

Reference Example 7

4-Bromoindoline

A solution of 4-bromoindole (881 mg) in acetonitrile (18 ml) was cooled to 0° C. under argon atmosphere, and thereto were added dropwise successively triethylsilane (2.15 ml), and boron trifluoride diethyl ether complex (1.71 ml). The mixture was stirred at the same temperature for 4 hours, and then further stirred at room temperature for 1.5 hours. To the resultant mixture was added a saturated aqueous sodium hydrogen carbonate solution, and the organic solvent was evaporated under reduced pressure. The residual mixture was extracted with ethyl acetate (60 ml) twice, and the combined organic layer was dried over magnesium sulfate. The insoluble materials were filtered off, and the filtrate was evaporated under reduced pressure. The residue was purified by silica gel column chromatography (chloroform:ethyl acetate=100:0-90:10) to give the titled compound (463 mg) as a yellow oil. APCI-Mass m/Z 198/200 (M+H). $^1$H-NMR (DMSO-d6) δ 2.90 (t, J=8.6 Hz, 2H), 3.45 (td, J=8.7, 1.4 Hz, 2H), 5.86 (br-s, 1H), 6.43 (d, J=7.7 Hz, 1H), 6.63 (d, J=7.9 Hz, 1H), 6.83 (t, J=7.9 Hz, 1H).

Reference Example 8

4-Methylindoline

In a manner similar to the methods disclosed in Reference Example 7, the titled compound was prepared from 4-methylindole. APCI-Mass m/Z 134 (M+H). $^1$H-NMR (DMSO-d6) δ 2.11 (s, 3H), 2.81 (t, J=8.5 Hz, 2H), 3.39 (td, J=8.6, 1.9 Hz, 2H), 5.37 (br-t, 1H), 6.30 (d, J=7.7 Hz, 1H), 6.33 (d, J=7.5 Hz, 1H), 6.78 (t, J=7.6 Hz, 1H).

Reference Example 9

4-(Difluoromethoxy)benzeneboronic acid

To a stirred solution of 1-bromo-4-(difluoromethoxy)-benzene (1.18 g) and triisopropyl borate (1.34 ml) in tetra-hydrofuran (6 ml) was added dropwise n-butyl lithium (1.58 M hexane solution, 3.68 ml) at −78° C. over 10 minutes under argon atmosphere, then the reaction mixture was allowed to warm to room temperature. After being starred at room temperature for 3 hours, the mixture was cooled to 0° C., and thereto were added a 6 N aqueous hydrochloric acid solution and water. The resultant mixture was extracted with ethyl acetate (30 ml) twice, and the combined organic layer was washed with brine (10 ml), dried over sodium sulfate. The insoluble materials were filtered off, and the filtrate was evaporated under reduced pressure. The residual solid was triturated with cold hexane to give the titled compound as a colorless solid. $^1$H-NMR (DMSO-d6) δ 7.12 (d, J=8.4 Hz, 2H), 7.27 (t, J=74.1 Hz, 1H), 7.83 (d, J=8.6 Hz, 2H), 8.08 (br-s, 2H).

Reference Example 10

4,6-Dichloroindoline (1) A mixture of 3,5-dichlorophenylhydrazine hydrochloride (5.07 g) and ethyl pyruvate (3.96 ml) in ethyl alcohol (30 ml) was refluxed for 2 hours, and the solvent was evaporated under reduced pressure. The residual solid was triturated with hexane to give ethyl 2-(3,5-dichlorophenylhydrazino)propionate (5.60 g). APCI-Mass m/Z 275/277 (M+H).

(2) A mixture of the above compound (8.16 g) and polyphosphoric acid (140 g) was stirred at 120° C. for 2 hours. Thereto was added water, and the mixture was extracted with ethyl acetate. The organic layer was washed with a saturated aqueous sodium hydrogen carbonate solution and brine, and dried over sodium sulfate. The insoluble materials were filtered off, and the filtrate was evaporated under reduced pressure. The residue was purified by silica gel column chromatography (chloroform only) to give ethyl 4,6-dichloroindole-2-carboxylate (6.22 g) as a colorless solid. APCI-Mass m/Z 258/260 (M+H).

(3) A mixture of the above compound (7.20 g) and potassium hydroxide (4.70 g) in ethyl alcohol (100 ml)-$H_2O$ (100 ml) was refluxed for 2 hours, and the organic solvent was evaporated under reduced pressure. Thereto was added water, and the mixture was washed with ethyl ether followed by being acidified with a 6 N aqueous hydrochloric acid solution. The resultant mixture was extracted with ethyl acetate, and the organic layer was washed with brine, dried over sodium sulfate. The insoluble materials were filtered off, and the filtrate was evaporated under reduced pressure to give crude 4,6-dichloroindole-2-carboxylic acid, which was used in the subsequent step without further purification.

(4) A suspension of the above compound and copper powder (800 ma) in quinoline (100 ml) was stirred at 190° C. for 2.5 hours under argon atmosphere. The reaction mixture was cooled to room temperature, and diluted with diethyl ether. The insoluble materials were filtered off, and the filtrate was successively washed with a 6 N aqueous hydrochloric acid solution 3 times, a saturated aqueous sodium hydrogen carbonate solution and brine followed by being dried over sodium sulfate. The insoluble materials were filtered off, and the filtrate was evaporated under reduced pressure. The residual oil was purified by silica gel column chromatography (hexane:ethyl acetate=9:1-3:1) to give 4,6-dichloroindole (5.36 g) as a brown oil. ESI-Mass m/Z 184/186 (M−H).

(5) The above compound was treated in a manner similar to Reference Example 1 to give the titled compound, 4,6-dichloroindoline as a pale brown oil. ESI-Mass m/Z 186/188 (M−H). $^1$H-NMR (DMSO-d6) δ 2.92 (t, J=8.7 Hz, 2H), 3.51 (t, J=8.7 Hz, 2H), 6.15 (s, 1H), 6.39 (d, J=1.4 Hz, 1H), 6.55 (d, J=1.4 Hz, 1H).

Reference Example 11

4-Chloro-5-fluoroindoline (1) A mixture of 3-chloro-4-fluoroaniline (10.0 g) in a 6 N aqueous hydrochloric acid solution (35 ml) was cooled to 0° C., and thereto was added dropwise a solution of sodium nitrite (4.80 g) in $H_2O$ (6.3 ml). After being stirred at same temperature for 25 minutes, the mixture was added to a solution of ethyl 2-methylacetoacetate (11.0 g), potassium hydroxide (21.2 g) and sodium acetate (21.2 g) in ethyl alcohol (80 ml)-$H_2O$ (100 ml) in one portion at 0° C. The resultant mixture was stirred at same temperature for 2 hours, and extracted with diethyl ether. The organic layer was washed with water twice and brine followed by being dried over sodium sulfate. The insoluble materials were filtered off, and the filtrate was evaporated under reduced pressure. The residue was purified by silica gel column chromatography (hexane:ethyl acetate=5:1-3:1) to give ethyl 2-(3-chloro-4-fluorophenylhydrazino)propionate (6.16 g) as a reddish solid. APCI-Mass m/Z 259/261 (M+H).

(2) The above compound (4.66 g) was dissolved in trifluoroacetic acid (150 ml), and the mixture was refluxed for 4 hours. The solvent was evaporated under reduced pressure, and the residue was dissolved in ethyl acetate. The solution was washed with a saturated aqueous sodium hydrogen carbonate solution 3 times and brine followed by being dried over sodium sulfate. The insoluble materials were filtered off, and the filtrate was evaporated under reduced pressure. The residue was purified by silica gel column chromatography (hexane:ethyl acetate=9:1) to give ethyl 4-chloro-5-fluoroindole-2-carboxylate (1.28 g) as a solid. mp 180-182° C. ESI-Mass m/Z 240/242 (M−H). $^1$H-NMR (DMSO-d6) δ 1.35 (t, J=7.1 Hz, 3H), 4.36 (q, J=7.1 Hz, 2H), 7.14 (d, J=1.4 Hz, 1H), 7.32 (t, J=9.4 Hz, 1H), 7.45 (dd, J=9.1, 3.9 Hz, 1H), 12.39 (s, 1H).

(3) The above ethyl 4-chloro-5-fluoroindole-2-carboxylate was treated in a manner similar to Reference Example 10-(3), (4) and 1 to give the titled compound, 4-chloro-5-fluoroindoline as a brown oil. APCI-Mass m/Z 172/174 (M+H). $^1$H-NMR (DMSO-d6) δ 2.97 (t, J=8.7 Hz, 2H), 3.48 (td, J=8.7, 1.9 Hz, 2H), 5.67 (s, 1H), 6.37 (dd, J=8.5, 3.7 Hz, 1H), 6.90 (t, J=9.2 Hz, 1H).

Reference Example 12

4-Pivaloyloxybenzoyl chloride (1) A solution of 4-hydroxybenzoic acid (6.91 g) and pyridine (12.1 ml) in dichloromethane (100 ml) was cooled to an ice-water temperature, and hereto was added dropwise pivaloyl chloride (13.26 g). The mixture was stirred at same temperature for 1.5 hours, and thereto was added a 10% aqueous hydrochloric acid solution (50 ml). The organic layer was washed with $H_2O$ (100 ml) and brine, and dried over magnesium sulfate. The insoluble materials were filtered off, and the filtrate was evaporated under reduced pressure. The residue was dissolved in tetrahydrofuran (100 ml)-$H_2O$ (15 ml), and the mixture was stirred at 50° C. for 17.5 hours. After being cooled to an ice-water temperature, the mixture was basified with a saturated aqueous sodium hydrogen carbonate solution (about 100 ml). After being stirred at room temperature for 4 hours, the mixture was acidified with a 36% aqueous hydrochloric acid solution at an ice-water temperature. The resultant mixture was extracted with ethyl acetate (100 ml), and the organic layer was dried over magnesium sulfate. The insoluble materials were filtered off, and the filtrate was evaporated under reduced pressure. The residue was purified by silica gel column chromatography (chloroform:methanol=50:1-9:1) and triturated with diisopropyl ether to give 4-pivaloyloxybenzoic acid (7.10 g) as a colorless solid. ESI-Mass m/Z 221 (M−H). $^1$H-NMR (DMSO-d6) δ 1.31 (s, 9H), 7.23 (d, J=8.5 Hz, 2H), 7.99 (d, J=8.7 Hz, 2H), 10.03 (brs, 1H).

(2) The above compound was treated in a manner similar to Reference Example 3 to give the titled compound, 4-pivaloyloxybenzoyl chloride.

Pharmacological Experiments

1. Assay for SGLT2 Inhibition

Test Compounds:

Compounds described in the above examples were used for the SGLT2 inhibition assay.

Method:

CHOK1 cells expressing human SGLT2 were seeded in 24-well plates at a density of 400,000 cells/well in F-12 nutrient mixture (Ham's F-12) containing 10% fetal bovine serum, 400 μg/ml Geneticin, 50 units/ml sodium penicillin G (Gibco-BRL) and 50 μg/ml streptomycin sulfate. After 2 days of culture at 37° C. in a humidified atmosphere containing 5% $CO_2$, cells were washed once with the assay buffer (137 mM NaCl, 5 mM KCl, 1 mM $CaCl_2$, 1 mM $MgCl_2$, 50 mM Hepes, and 20 mM Tris, pH 7.4) and incubated with 250 μl of the buffer containing test compounds for 10 min at 37° C. Test compounds were dissolved in DMSO. The final concentration of DMSO was 0.5%. The transport reaction was initiated by addition of 50 μl [$^{14}$C]-methyl-α-D-glucopyranoside ($^{14}$C-AMG) solution (final concentration, 0.5 mM). After incubation for 2 hours at 37° C., the uptake was stopped by aspiration of the incubation mixture, the cells were washed three times with ice-cold PBS. Then, cells were solubilized with 0.3 N NaOH and aliquots were taken for determination of radioactivity by a liquid scintillation counter. Nonspecific AMG uptake was defined as that which occurred in the presence of 100 μM of phlorizin, a specific inhibitor of sodium-dependent glucose cotransporter. Specific uptake was normalized for the protein concentrations measured by the method of Bradford. The 50% inhibitory concentration ($IC_{50}$) values were calculated from dose-response curves by least square method.

Results:

Results are shown in the following table:

TABLE 2

| Test Compounds (Example No.) | $IC_{50}$ (nM) |
|---|---|
| 1 | 2.9 |
| 2 | 5.2 |
| 3 | 3.5 |
| 4 | 1.7 |
| 5 | 1.8 |
| 6 | 9.8 |
| 7 | 5.0 |
| 8 | 4.8 |
| 9 | 3.3 |
| 10 | 2.4 |
| 11 | 2.4 |
| 12 | 4.1 |
| 13 | 6.0 |
| 14 | 8.1 |
| 15 | 3.3 |
| 16 | 2.1 |
| 17 | 2.5 |
| 18 | 4.1 |
| 19 | 3.9 |
| 20 | 5.7 |
| 21 | 1.8 |
| 22 | 3.7 |
| 23 | 1.1 |
| 24 | 6.3 |
| 25 | 11 |

TABLE 2-continued

| Test Compounds (Example No.) | $IC_{50}$ (nM) |
|---|---|
| 26 | 11 |
| 27 | 16 |
| 28 | 3.2 |
| 29 | 9.6 |
| 30 | 3.2 |
| 31 | 2.6 |
| 32 | 7.5 |
| 33 | 4.1 |
| 34 | 11 |
| 35 | 9.1 |
| 36 | 14 |
| 37 | 14 |
| 38 | 12 |
| 39 | 3.6 |
| 40 | 6.2 |
| 41 | 12 |
| 42 | 6.1 |
| 43 | 8.4 |
| 44 | 20 |
| 45 | 2.5 |
| 46 | 2.4 |
| 47 | 1.6 |
| 48 | 19 |
| 49 | 8.8 |
| 50 | 11 |
| 51 | 6.1 |
| 52 | 2.8 |

2. Urinary Glucose Excretion Test in Rats

Test Compounds:

Compounds described in the above examples were used for the Urinary glucose excretion test in rats.

Methods:

6-week-old male Sprague-Dawley (SD) rats were housed in individual metabolic cages with free access to food and water from 2 days prior to the experiment. On the morning of the experiment, rats were administered vehicle (0.2% carboxymethyl cellulose solution containing 0.2% Tween80) or test compounds (30 mg/kg) by oral gavage at a volume of 10 ml/kg. Then, urine of the rat was collected for 24 hours, and the urine volume was measured. Subsequently, the glucose concentration in urine was quantified using the enzymatic assay kit and the daily amount of glucose excreted in urine per individual was calculated.

Results:

Urinary glucose amounts ranges are depicted by A and B. These ranges are as follows: A≧2400 mg; 2400 mg>B≧2000 mg.

TABLE 3

| Test compounds (Example No.) | Urinary glucose |
|---|---|
| 2 | A |
| 3 | B |
| 6 | A |
| 7 | B |
| 8 | A |
| 13 | B |
| 14 | A |
| 15 | A |
| 18 | B |
| 19 | A |
| 20 | A |
| 25 | B |
| 26 | A |
| 27 | B |
| 28 | B |
| 29 | B |

TABLE 3-continued

| Test compounds (Example No.) | Urinary glucose |
| --- | --- |
| 30 | A |
| 31 | A |
| 32 | B |
| 33 | A |
| 34 | B |
| 35 | A |
| 36 | B |
| 37 | B |
| 38 | B |
| 39 | B |
| 40 | B |
| 41 | B |
| 42 | A |
| 43 | A |
| 44 | B |
| 46 | A |
| 47 | A |

The invention claimed is:

1. A compound of formula (I), or a pharmaceutically acceptable salt thereof:

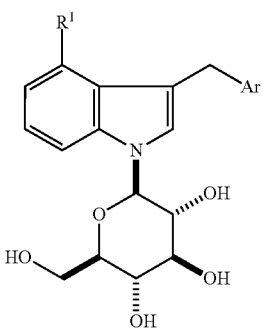

wherein $R^1$ is halogen, and

Ar is one of the following groups:

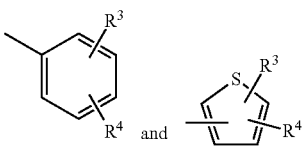

in which $R^3$ and $R^4$ are independently hydrogen, halogen, alkyl, haloalkyl, alkoxy, haloalkoxy, alkylthio, phenyl, halophenyl, cyanophenyl, pyridyl or halopyridyl, or $R^3$ and $R^4$ together with carbon atoms to which they are attached form a fused benzene, furan or dihydrofuran ring.

2. The compound according to claim 1, wherein $R^3$ and $R^4$ are independently hydrogen, halogen, alkyl, haloalkyl, alkoxy, haloalkoxy, or $R^3$ and $R^4$ together with carbon atoms to which they are attached form a fused furan or dihydrofuran ring.

3. The compound according to claim 1, wherein Ar is

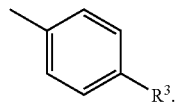

4. The compound according to claim 3, wherein $R^3$ is halogen, alkyl, haloalkyl, alkoxy, or haloalkoxy.

5. The compound according to claim 4, wherein $R^1$ is chlorine.

6. The compound according to claim 5, wherein $R^3$ is halogen, haloalkyl or haloalkoxy.

7. The compound according to claim 3, wherein $R^1$ is fluorine and $R^3$ is alkyl, alkoxy, haloalkyl or haloalkoxy.

8. The compound according to claim 1, wherein Ar is

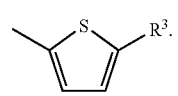

9. The compound according to claim 8, wherein $R^1$ is halogen, and $R^3$ is halogen or alkyl.

10. The compound according to claim 1, wherein Ar is

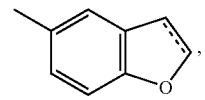

in which ==== represents a single bond or a double bond.

11. The compound according to claim 1, wherein the compound is selected from a group consisting of:
   4-chloro-3-(4-ethylphenylmethyl)-1-(β-D-glucopyranosyl)-indole;
   4-chloro-3-(4-ethoxyphenylmethyl)-1-(β-D-glucopyranosyl)-indole;
   3-(5-bromothiophen-2-yl-methyl)-4-chloro-1-(β-D-gluco-pyranosyl)indole;
   3-(4-ethylphenylmethyl)-4-fluoro-1-(β-D-glucopyranosyl)-indole; and
   a pharmaceutically acceptable salt thereof.

12. The compound according to claim 1, wherein the compound is selected from a group consisting of:
   4-chloro-3-(4-chlorophenylmethyl)-1-(β-D-glucopyranosyl)-indole;
   3-(4-ethoxyphenylmethyl)-4-fluoro-1-(β-D-glucopyranosyl)-indole;
   3-(4-bromophenylmethyl)-4-chloro-1-(β-D-glucopyranosyl)-indole;
   3-(benzo[b]furan-5-yl-methyl)-4-chloro-1-(β-D-gluco-pyranosyl)indole;
   4-chloro-3-(4-(difluoromethyl)phenylmethyl)-1-(β-D-glucopyranosyl)indole;
   4-chloro-3-(4-(difluoromethoxy)phenylmethyl)-1-(β-D-glucopyranosyl)indole;
   4-chloro-3-(4-iodophenylmethyl)-1-(β-D-glucopyranosyl)-indole;
   4-chloro-3-(4-(trifluoromethoxy)phenylmethyl)-1-(β-D-glucopyranosyl)indole; and
   a pharmaceutically acceptable salt thereof.

13. A pharmaceutical composition comprising the compound as set forth in claim 1 and a pharmaceutically acceptable carrier or diluent.

14. The pharmaceutical composition according to claim 13, which further comprises another antidiabetic agent.

15. A compound as set forth in claim 1 for use as an active therapeutic substance.

16. A method for treatment or delaying the progression or onset of diabetes mellitus, diabetic retinopathy, diabetic neuropathy, diabetic nephropathy, delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, diabetic complications, atherosclerosis, or hypertension, which comprises administering to a mammalian species in need of treatment a therapeutically effective amount of the compound as set forth in claim 1.

17. A method for treatment of type 1 or type 2 diabetes mellitus, which comprises administering to a mammalian species in need of treatment a therapeutically effective amount of the compound as set forth in claim 1 alone, or in combination with another antidiabetic agent, an agent for treating diabetic complications, an anti-obesity agent, an anti-hypertensive agent, an antiplatelet agent, an anti-atherosclerotic agent and/or a hypolipidemic agent.

18. A process for preparing a compound of formula:

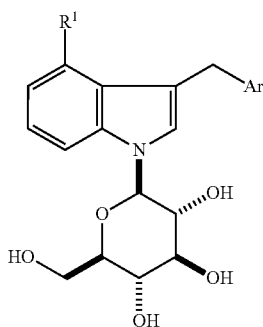

(I)

wherein the symbols are the same as defined in claim 1, or a pharmaceutically acceptable salt thereof, which comprises deprotecting a compound of formula (II)

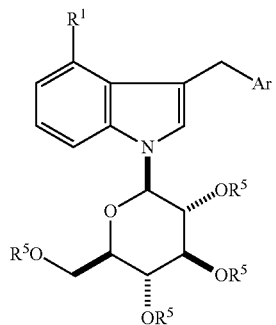

(II)

wherein $R^5$ is a protecting group for hydroxyl group and the other symbols are the same as defined above, followed by converting the resulting compound into a pharmaceutically acceptable salt thereof, if desired.

19. A compound of formula (II)

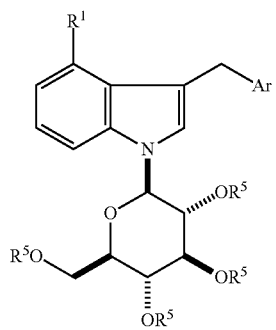

(II)

wherein $R^5$ is a protecting group for a hydroxy group and the other symbols are the same as defined in claim 1, or a salt thereof.

* * * * *